United States Patent
Wang et al.

(10) Patent No.: US 10,584,340 B2
(45) Date of Patent: Mar. 10, 2020

(54) TAU PROTEIN-BINDING DNA APTAMERS WITH CAPTURE/DETECTION AND THERAPEUTIC UTILITIES IN TAUOPATHY-RELATED NEURODEGENERATIVE DISORDERS

(71) Applicants: UNIVERSITY OF FLORIDA RESEARCH FOUNDATION, INC., Gainesville, FL (US); DEPARTMENT OF VETERAN'S AFFAIRS, Washington, DC (US)

(72) Inventors: Ka W. Wang, Gainesville, FL (US); Weihong Tan, Gainesville, FL (US); Xiaowei Li, Gainesville, FL (US); Hamad Yadikar, Gainesville, FL (US); I-Ting Teng, Gainesville, FL (US)

(73) Assignees: University of Florida Research Foundation, Inc., Gainesville, FL (US); Department of Veteran's Affairs, Washington, DC (US)

( * ) Notice: Subject to any disclaimer, the term of this patent is extended or adjusted under 35 U.S.C. 154(b) by 0 days.

(21) Appl. No.: 15/720,084

(22) Filed: Sep. 29, 2017

(65) Prior Publication Data

US 2019/0101529 A1    Apr. 4, 2019

(51) Int. Cl.
| | | |
|---|---|---|
| *C12N 15/11* | (2006.01) |
| *C12N 15/115* | (2010.01) |
| *G01N 33/68* | (2006.01) |
| *A61K 49/00* | (2006.01) |

(52) U.S. Cl.
CPC ........ *C12N 15/115* (2013.01); *A61K 49/0002* (2013.01); *G01N 33/6896* (2013.01); *C12N 2310/16* (2013.01); *G01N 2440/14* (2013.01); *G01N 2800/2821* (2013.01)

(58) Field of Classification Search
None
See application file for complete search history.

(56) References Cited

FOREIGN PATENT DOCUMENTS

DE    102010038842 A1    2/2012

OTHER PUBLICATIONS

Aslett et al, Pathogen Informatics, Wellcome Trust Genome Campus, Hinxton, Cambridge, Cambridgeshire., CB10 'ISA, United Kingdom, 2014, p. 1 (search result) (Year: 2014).*
Wang, Y. et al, "Tau in physiology and pathology", Nat Rev Neurosci, Jan. 2016, 17 (1), 22-35.
Hanger, D. P. et al., "Tau phosphorylation: the therapeutic challenge for neurodegenerative disease", Trends in Molecular Medicine, 2009, 15 (3), 112-119.
Krylova, S. M. et al., "Tau protein binds single-stranded DNA sequence specifically—the proof obtained in vitro with non-equilibrium capillary electrophoresis of equilibrium mixtures", FEBS Letters, 2005, 579 (6), 1371-1375.
Kim JH et al., "Inhibitory RNA Aptamers of Tau Oligomerization and Their Neuroprotective Roles against Proteotoxic Stress", Mol Pharm., Jun. 6, 2016; 13 (6), 2039-2048.

* cited by examiner

*Primary Examiner* — Ekaterina Poliakova-Georgantas
(74) *Attorney, Agent, or Firm* — Timothy H. Van Dyke; Beusse, Wolter, Sanks & Maire PLLC

(57) ABSTRACT

DNA aptamers that bind to tau protein at its phosphorylatable sites are identified. These disclosed DNA aptamers not only recognize tau at specific phosphorylatable sites, but also demonstrate inhibitory effects on phosphorylation and oligomer formation of tau protein. Molecular probes based on these disclosed DNA aptamers can be used as capture or detection agents to detect the levels of tau and phosphor-tau in cerebrospinal fluid as well as for cell-based or in vivo brain imaging in live animals or human. Compositions comprising these disclosed DNA aptamers can be used to arrest or treat the progression of tauopathy associated neurodegenerative disorders.

10 Claims, 40 Drawing Sheets

Specification includes a Sequence Listing.

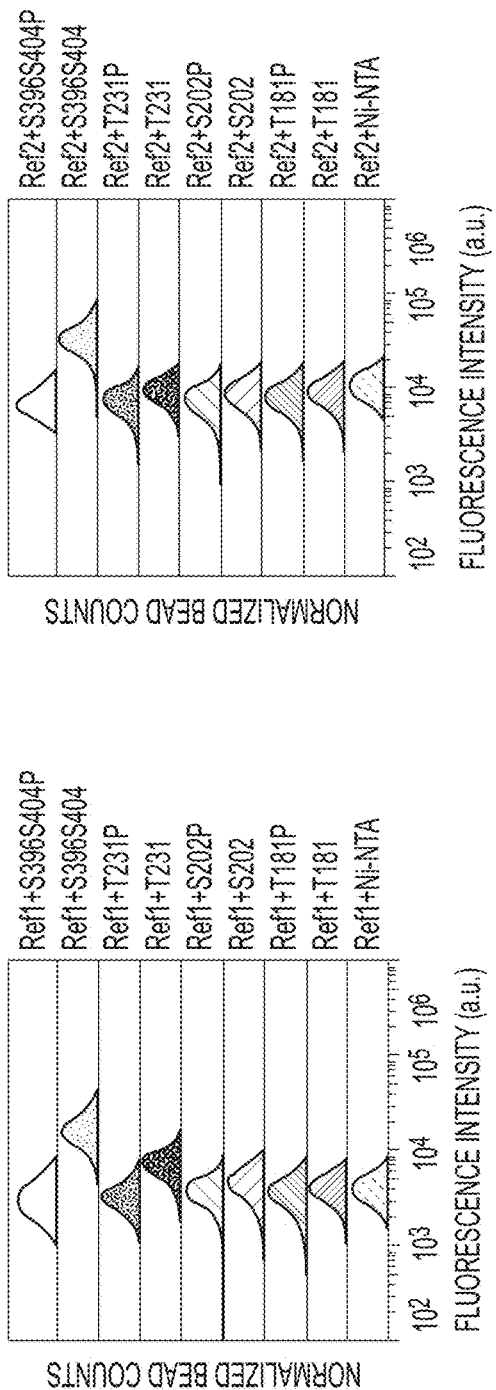
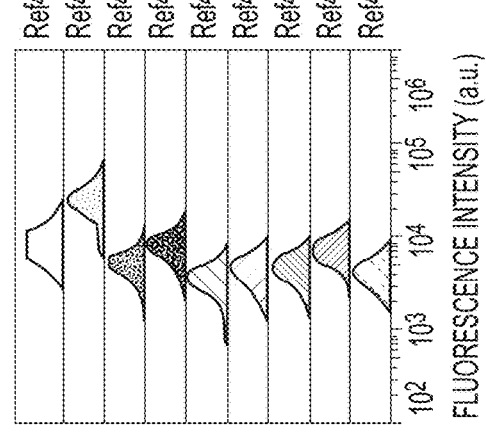
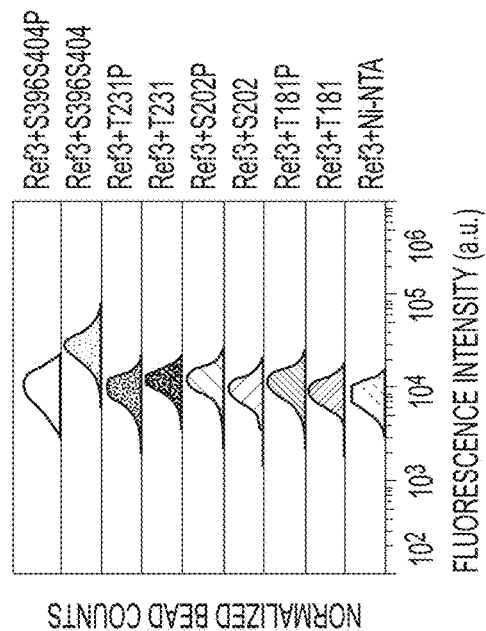
FIG. 7A, FIG. 7B, FIG. 7C, FIG. 7D

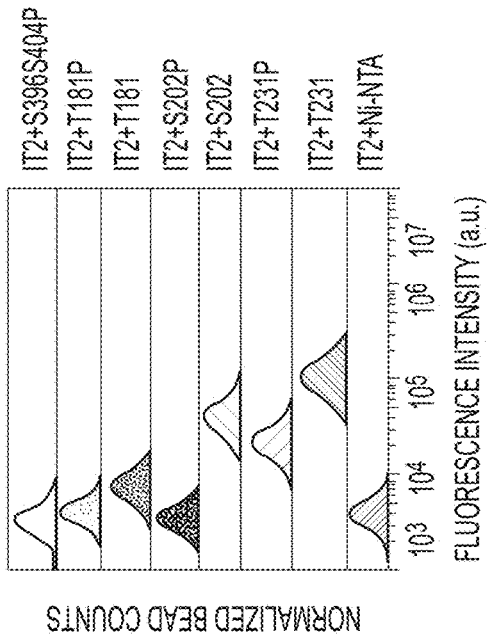
FIG. 12A
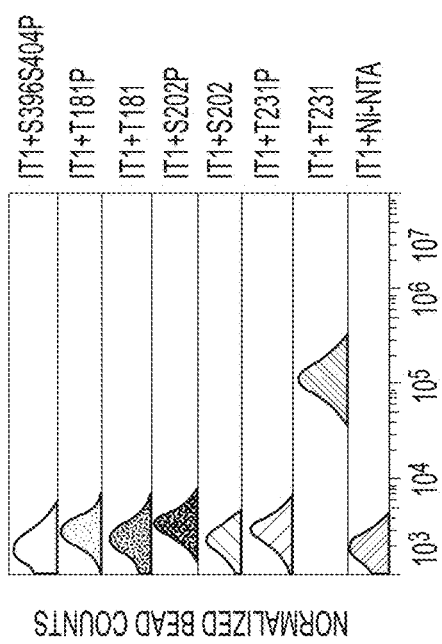
FIG. 12B (rotated label: this is FIG. 12A area) 
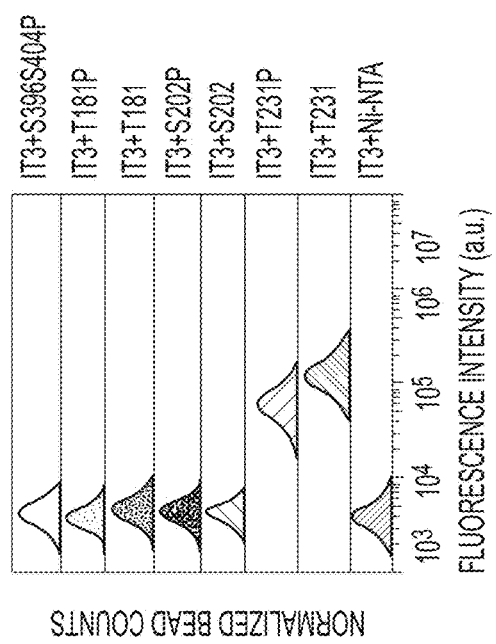
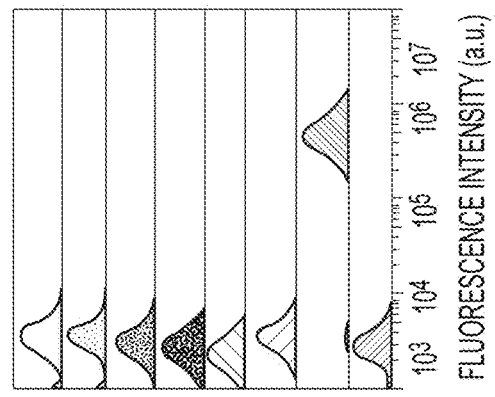

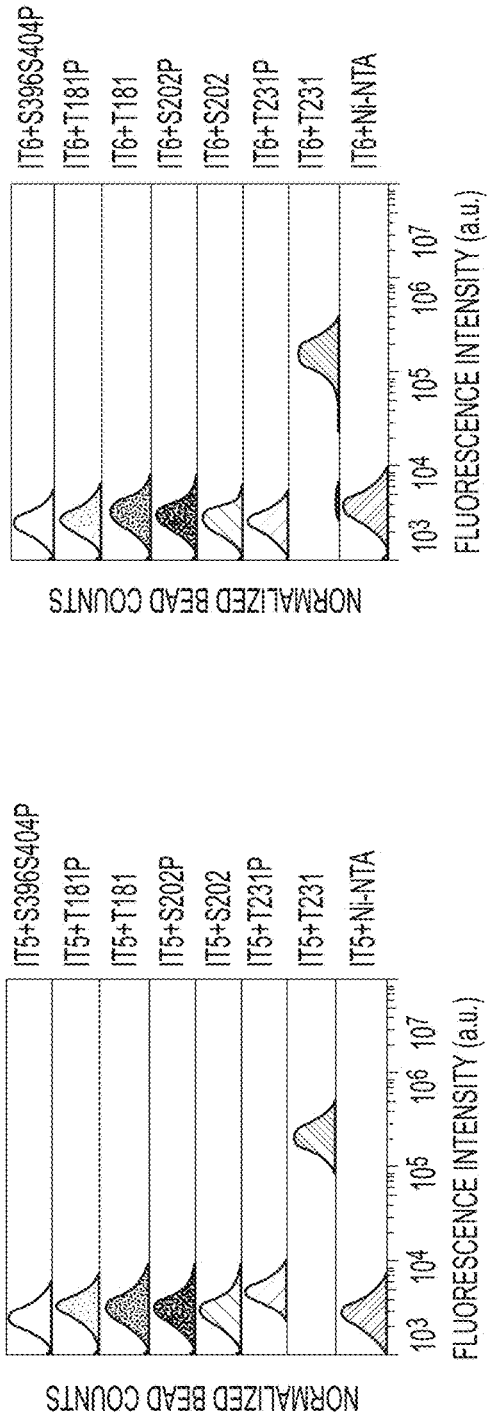
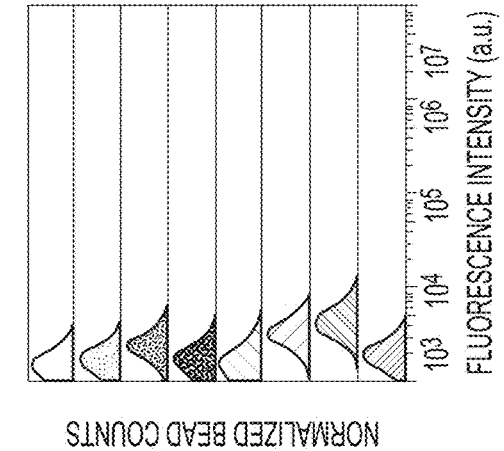
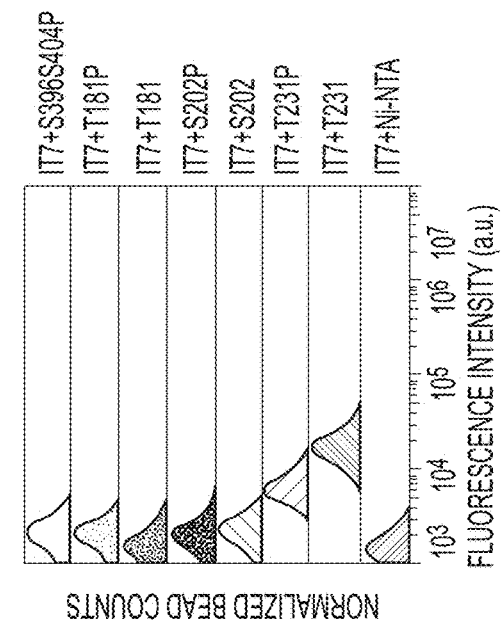
FIG. 12E
FIG. 12F
FIG. 12G
FIG. 12H $$\text{Since } \begin{cases} [Aptamer]_t = constant \\ [Target]_t = [Target]_{max} - [Aptamer \cdot Target]_t \end{cases}$$

$$\text{and } \begin{cases} [Aptamer \cdot Target] \propto R_t \\ [Target]_{max} \propto R_{max} \end{cases}$$

Equation 4 at any time point in the association phase $$\rightarrow \frac{d[Aptamer \cdot Target]}{dt} = k_{on}[Aptamer]_t[Target]_t - k_{off}[Aptamer \cdot Target]_t$$

$$\text{can be reformulated into } \rightarrow \frac{dR_t}{dt} = k_{on}[Aptamer](R_{max} - R_t) - k_{off}R_t$$

$$\Rightarrow R_t = \underbrace{\frac{R_{max}[Aptamer]}{K_d + [Aptamer]}}_{\text{Determines the equilibrium level}} \underbrace{\left[1 - e^{-(k_{on}[Aptamer]+k_{off})t}\right]}_{\text{Determines the time to reach equilibrium}}$$

*FIG. 21*

*As shown in Equation 3 − 5 and Equation 3 − 6* at equilibrium $\quad k_{on}[Aptamer][Target] = k_{off}[Aptamer \cdot Target]$ $$\rightarrow K_d = \frac{k_{off}}{k_{on}} = \frac{[Aptamer][Target]}{[Aptamer \cdot Target]}$$

$$\rightarrow [Target] = K_d \frac{[Aptamer \cdot Target]}{[Aptamer]}$$

$$\begin{cases} [Aptamer]_0 = [Aptamer] + [Aptamer \cdot Target] \\ [Target]_0 = [Target] + [Aptamer \cdot Target] \end{cases}$$

$$\rightarrow [Target]_0 = K_d \frac{[Aptamer \cdot Target]}{[Aptamer]} + [Aptamer \cdot Target]$$

$$= [Aptamer \cdot Target]\left(\frac{K_d}{[Aptamer]} + 1\right)$$

$$= [Aptamer \cdot Target]\left(\frac{K_d + [Aptamer]}{[Aptamer]}\right)$$

$$\Rightarrow [Aptamer \cdot Target] = \frac{[Target]_0[Aptamer]}{K_d + [Aptamer]}$$

$$\Rightarrow R_{eq} = \frac{R_{max}[Aptamer]}{K_d + [Aptamer]}$$

*FIG. 22*

$When\ [Aptamer] = 0$ $$\frac{d[Aptamer \cdot Target]}{dt} = k_{on}[Aptamer][Target] - k_{off}[Aptamer \cdot Target]$$

$$\frac{d[Aptamer \cdot Target]}{dt} = k_{on}[Aptamer][Target] - k_{off}[Aptamer \cdot Target]$$

$$= -k_{off}[Aptamer \cdot Target]$$

$$\rightarrow \frac{dR_t}{dt} = -k_{off}R_t$$

$$\Rightarrow R_t = R_0 e^{-k_{off}t}$$

*FIG. 23*

Lanes:
1 - Aptamer
2 - Aptamer + Tau441
3 - Aptamer + S100B
4 - Aptamer + UCH-L1
5: Aptamer + α casein
6: Aptamer + β casein
7: Aptamer + BSA
8: Aptamer + IgG 1: Tau
2: Tau + heparin
3: Tau + heparin + random sequence (20 μM)
4: Tau + heparin + IT3 (5 μM)
5: Tau + heparin + IT3 (10 μM)
6: Tau + heparin + IT3 (20 μM)

1: SH-SY5Y without any treatment
2: SH-SY5Y + okadaic acid
3: SH-SY5Y + random sequence + okadaic acid
4: SH-SY5Y + IT1c + okadaic acid
5: SH-SY5Y + IT2a + okadaic acid FIG. 27A
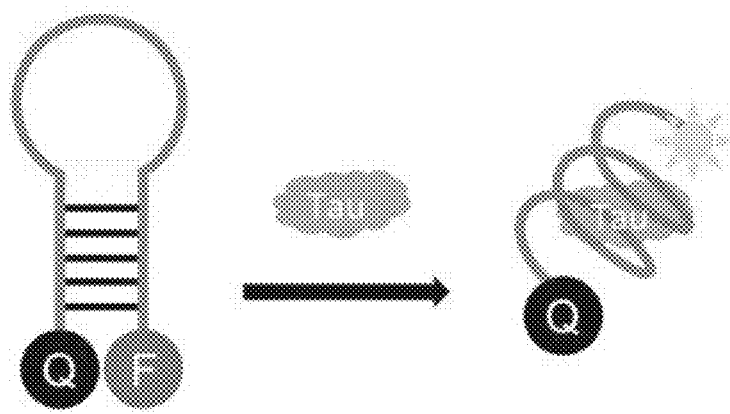
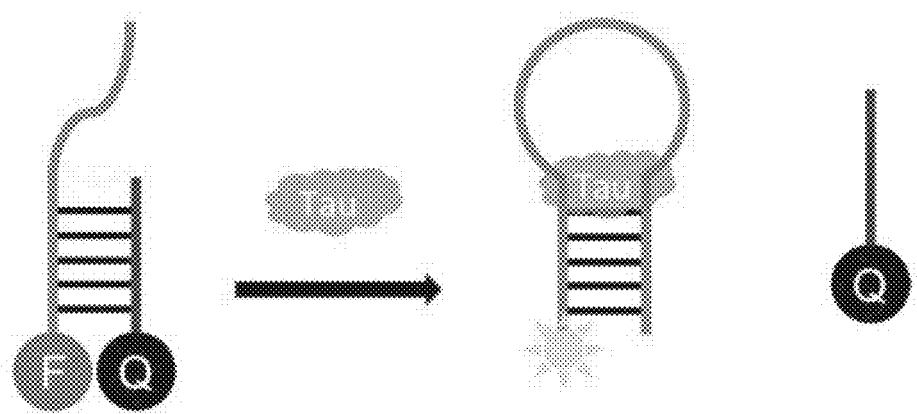
FIG. 27B

Sequence Truncation – Summary

| Sequence | # of truncations | Epitope |
|---|---|---|
| T1 | 66 | T231 |
| D1b | 55+3T (6-60) | T231 |
| D1b | 43+2T (6-48) | T231 |
| D1c | 29+3T (20-48) | T231 |
| D1d | 25 (22-46) | x |
| D2 | 66 | T231, T231P, S202 |
| D2a | 35+3T (13-47) | T231, T231P, S202 |
| D2b | 19+2T (19-37) | x |
| D2c | 33 (14-46) | T231, T231P, S202 |
| D2d | 31+3T (15-45) | T231, T231P |
| D2e | 29 (16-44) | Weak T231 |

| Sequence | # of truncations | Epitope |
|---|---|---|
| T3 | 66 | T231, T231P |
| D3a | 37+3T (1-37) | x |
| D3b | 56+3T (1-56) | x |
| D3c | 61+2T (1-61) | Weak T231 |
| T4 | 66 | T231 |
| D4a | 48+3T (4-51) | x |
| D4b | 56+3T (4-59) | x |
| D4c | 59+3T (1-59) | x |
| T5 | 66 | T231 |
| D5a | 31+3T (6-36) | x |
| D5b | 42 (4-45) | x |
| D5c | 53+3T (4-56) | x |
| T6 | 66 | T231 |
| D6a | 48+3T (4-51) | T231 |
| D6b | 39 (7-45) | x |

FIG. 31

TAU PROTEIN-BINDING DNA APTAMERS WITH CAPTURE/DETECTION AND THERAPEUTIC UTILITIES IN TAUOPATHY-RELATED NEURODEGENERATIVE DISORDERS

GOVERNMENT INTEREST STATEMENT

This invention was made with government support under Grant GM079359-08 awarded by The National Institutes of Health. The government has certain rights in the invention.

The research described here was support in part by the Department of Veteran's Affairs, Veterans Health Administration, Rehabilitation Research and Development Service. Award Number I01 RX001859 A02. Dr. Kevin Wang, Associate Professor. The government has certain rights in the invention.

CROSS-REFERENCE TO RELATED APPLICATIONS

This application makes reference to the following U.S. patents and U.S. patent applications.

U.S. Pat. No. 9,664,694, entitled "Neural Proteins as Biomarkers for Nervous System Injury and Other Neural Disorders," filed Nov. 19, 2010, issued May 30, 2017, which is a continuation of U.S. Ser. No. 12/822,560, filed Jun. 24, 2010, which is a continuation-in-part of U.S. Ser. No. 12/137,194, filed Jun. 11, 2008, now abandoned, which is a divisional of U.S. Ser. No. 11/107,248, filed Apr. 15, 2005, now U.S. Pat. No. 7,396,654, which claims the benefit of U.S. Provisional Application Ser. No. 60/562,944, filed Apr. 15, 2004.

U.S. Pat. No. 8,557,526, entitled "Synaptotagmin and collapsin response mediator protein as biomarkers for traumatic brain injury," issued Oct. 15, 2013, which is a continuation-in-part of International Application No. PCT/US2008/001644, filed Feb. 6, 2008, which claims priority from U.S. Provisional Application Ser. No. 60/888,432, filed Feb. 6, 2007.

U.S. Pat. No. 8,298,835, entitled "Proteolytic markers as diagnostic biomarkers for cancer, organ injury and muscle rehabilitation/exercise overtraining," issued Oct. 30, 2012, which is a divisional of U.S. Ser. No. 11/106,932, filed Apr. 15, 2005 now U.S. Pat. No. 7,456,027, which claims the priority of U.S. Provisional Patent application No. 60/562,819 filed Apr. 15, 2004.

U.S. Pat. No. 8,492,107, entitled "Neural Proteins as Biomarkers for Nervous System Injury and Other Neural Disorders," issued, Jul. 23, 2013, which is a continuation-in-part of U.S. Ser. No. 12/137,194, filed Jun. 11, 2008, which is a divisional of U.S. Ser. No. 11/107,248, filed Apr. 15, 2005, now U.S. Pat. No. 7,396,654, which claims the benefit of U.S. Provisional Application Ser. No. 60/562,944, filed Apr. 15, 2004.

U.S. Pat. No. 8,048,638, entitled "Biomarkers of liver injury," issued Nov. 1, 2011, which is a continuation-in-part of U.S. Ser. No. 11/396,406, filed Mar. 31, 2006, now U.S. Pat. No. 7,645,584, which claims the benefit of U.S. provisional Ser. No. 60/668,121, filed Apr. 1, 2005.

U.S. Pat. No. 7,645,584, entitled "Biomarkers of liver injury," issued Jan. 12, 2010, which claims the priority of U.S. provisional patent application No. 60/668,121, entitled "BIOMARKERS OF LIVER INJURY," filed Apr. 1, 2005.

U.S. Pat. No. 7,611,858, entitled "Detection of cannabinoid receptor biomarkers and uses thereof," issued Nov. 3, 2009, which is a continuation-in-part of International Application Serial No. PCT/US2005/038185, filed Oct. 21, 2005, which claims the benefit of U.S. Provisional Patent Application No. 60/620,790, filed Oct. 21, 2004.

U.S. Pat. No. 7,456,027, entitled "Proteolytic biomarkers for traumatic injury to the nervous system," issued Nov. 25, 2008, which claims the priority of U.S. Provisional Patent application No. 60/562,819 filed Apr. 15, 2004; and entitled "PROTEOLYTIC MARKERS AS DIAGNOSTIC BIOMARKERS FOR CANCER, ORGAN INJURY AND MUSCLE REHABILITATION/EXERCISE OVERTRAINING."

U.S. Pat. No. 7,396,654, entitled "Neural proteins as biomarkers for traumatic brain injury," issued Jul. 8, 2008, which claims the priority of U.S. Provisional Patent application No. 60/562,944 filed Apr. 15, 2004; and entitled "NEURAL PROTEINS AS BIOMARKERS FOR NERVOUS SYSTEM INJURY AND OTHER NEURAL DISORDERS."

U.S. Pat. No. 7,291,710, entitled "Detection of spectrin and spectrin proteolytic cleavage products in assessing nerve cell damage," issued Nov. 6, 2007, claims the priority of U.S. provisional patent application No. 60/409,920 entitled "Analyzing Central Nervous system Injuries," and filed Sep. 11, 2002.

U.S. Pat. No. 7,052,854, entitled "Application of nanotechnology and sensor technologies for ex-vivo diagnostics," issued May 30, 2006, which is a continuation-in-part of co-pending U.S. application Ser. No. 10/154,201, filed May 22, 2002; which claims the benefit of U.S. application Ser. No. 60/292,962, filed May 23, 2001. This application is also a continuation-in-part of co-pending U.S. application Ser. No. 10/274,829, filed Oct. 21, 2002; and a continuation-in-part of co-pending U.S. application Ser. No. 10/345,532, filed Jan. 16, 2003.

U.S. patent application Ser. No. 15/391,755, entitled "Micro-RNA, Autoantibody and Protein Markers for Diagnosis of Neuronal Injury," which is a continuation of U.S. patent application Ser. No. 13/395,931, filed Jul. 12, 2012, which is filed as PCT/US10/48789 on Sep. 14, 2010, which claims priority from U.S. Provisional Patent Application No. 61/242,123, entitled "Markers for Diagnosis of Neuronal Injury," filed Sep. 14, 2009; U.S. Provisional Patent Application No. 61/354,504, entitled "Glial Fibrillary Acidic Protein, Breakdown Products Thereof, and Autoantibodies Thereto as Biomarkers of Neurological Condition," filed Jun. 14, 2010; U.S. Provisional Patent Application No. 61/355,779, entitled "Glial Fibrillary Acidic Protein, Breakdown Products Thereof, and Autoantibodies Thereto as Biomarkers of Neurological Condition," filed Jun. 17, 2010, and U.S. Provisional Patent Application No. 61/380,158, entitled "Markers for Diagnosis of Neuronal Injury," filed Sep. 3, 2010.

U.S. patent application Ser. No. 14/120,992, entitled "Endothelial-Monocyte Activating Polypeptide II (Emap-II), a Biomarker for Use in Diagnosis and Treatment of Brain Injury," filed Sep. 26, 2014, which is a division of U.S. patent application Ser. No. 12/806,725, filed Aug. 19, 2010, which is a division of U.S. patent application Ser. No. 12/290,174, filed Oct. 28, 2008, now U.S. Pat. No. 7,799,536, which is a continuation of Application No. PCT/US2007/011613, filed May 15, 2007, which claims priority from U.S. Provisional Patent Application No. 60/809,986, filed May 18, 2006.

U.S. patent application Ser. No. 15/308,934, entitled "PROTEIN BIOMARKERS FOR ACUTE, SUBACUTE AND CHRONIC TRAUMATIC INJURIES OF THE CENTRAL NERVOUS SYSTEM," filed Apr. 8, 2015, which claims the benefit of U.S. Provisional Application Ser. No. 61/976,733, filed Apr. 8, 2014.

U.S. patent application Ser. No. 15/340,002, entitled "Neural Proteins as Biomarkers for Nervous System Injury and Other Neural Disorders," filed Nov. 1, 2016, which is a continuation of U.S. Ser. No. 12/950,142, filed Nov. 19, 2010, which is a continuation of U.S. Ser. No. 12/822,560, filed Jun. 24, 2010, now U.S. Pat. No. 8,492,107, which is a continuation-in-part of U.S. Ser. No. 12/137,194, filed Jun. 11, 2008, now abandoned, which is a divisional of U.S. Ser. No. 11/107,248, filed Apr. 15, 2005, now U.S. Pat. No. 7,396,654, which claims the benefit of U.S. Provisional Application Ser. No. 60/562,944, filed Apr. 15, 2004.

U.S. patent application Ser. No. 13/470,079, entitled "In Vitro Diagnostic Devices for Nervous System Injury and Other Neural Disorders," filed May 11, 2012, which is a continuation-in-part of application Ser. No. 12/950,142, filed on Nov. 19, 2010, which is a continuation of application Ser. No. 12/822,560, filed on Jun. 24, 2010, now U.S. Pat. No. 8,492,107, which is a continuation-in-part of application Ser. No. 12/137,194, filed on Jun. 11, 2008, now abandoned, which is a division of U.S. patent application Ser. No. 11/107,248, filed Apr. 15, 2005, now U.S. Pat. No. 7,396,654, which claims priority from U.S. Provisional Patent Application No. 61/484,945, filed May 11, 2011, and U.S. Provisional Patent Application No. 60/562,944, filed Apr. 15, 2004.

U.S. patent application Ser. No. 15/441,183, "Biomarker Assay of Neurological Condition," filed on Feb. 23, 2017, which is a continuation in part of U.S. patent application Ser. No. 13/395,931, filed Jul. 12, 2012, which is a continuation-in-art of U.S. patent application Ser. No. 13/379,164, filed Jun. 29, 2012, which is a continuation-in-art of International Patent Application No. PCT/US11/40998, filed Jun. 17, 2011, which claims priority from U.S. Provisional Patent Application No. 61/476,158, filed Apr. 15, 2011; this patent application is also a national stage entry of International Patent Application No. PCT/US10/48789, filed Sep. 14, 2010, which claims priority from U.S. Provisional Patent Application No. 61/380,158, filed Sep. 3, 2010; which is also a national stage entry of International Patent Application No. PCT/US2010/039335, filed Jun. 21, 2010, which claims priority from U.S. Provisional Patent Application No. 61/355,779, file Jun. 7, 2010, U.S. Provisional Patent Application No. 61/354,504, filed Jun. 14, 2010, U.S. Provisional Patent Application No. 61/345,188, filed May 17, 2010, U.S. Provisional Patent Application No. 61/242,123, filed Sep. 14, 2009, and U.S. Provisional Patent Application No. 61/218,727, filed Jun. 19, 2009.

U.S. patent application Ser. No. 13/717,405, entitled "Biomarker Assay of Neurological Condition," filed Dec. 17, 2012, which is a continuation-in-part of U.S. patent application Ser. No. 13/379,164, filed as application No. PCT/US2010/039335 on Jun. 21, 2010, which claims priority from U.S. Provisional Patent Application No. 61/218,727, filed Jun. 19, 2009, U.S. Provisional Patent Application No. 61/345,188, filed May 17, 2010; and U.S. Provisional Patent Application No. 61/355,779, entitled "Glial Fibrillary Acidic Protein, Breakdown Products Thereof, and Autoantibodies Thereto as Biomarkers of Neurological Condition," filed Jun. 17, 2010.

U.S. patent application Ser. No. 15/441,223, entitled "Processes and Kits to Detect and Monitor for Diagnostic Biomarkers for Post Traumatic Stress Disorder (Ptsd) and to Differentiate Between Suicidal and Non-Suicidal form of the Disorder," filed Feb. 23, 2017, which is a continuation of U.S. patent application Ser. No. 13/618,589, filed Sep. 14, 2012, which claims priority from U.S. Provisional Patent Application No. 61/569,047, filed Dec. 9, 2011, and U.S. Provisional Patent Application No. 61/534,560, filed Sep. 14, 2011.

U.S. patent application Ser. No. 13/337,588, entitled "Synaptotagmin and collapsin response mediator protein as biomarkers for traumatic brain injury," filed Dec. 27, 2011, which claims the priority of U.S. provisional application Ser. No. 61/427,343, filed Dec. 27, 2010. The present application is also a continuation-in-part of co-pending U.S. application Ser. No. 12/535,960, filed Aug. 5, 2009, which is a continuation-in-part of International Application No. PCT/US2008/001644, filed Feb. 6, 2008, which claims the benefit of U.S. provisional application Ser. No. 60/888,432, filed Feb. 6, 2007.

U.S. patent application Ser. No. 12/950,142, entitled "NEURAL PROTEINS AS BIOMARKERS FOR NERVOUS SYSTEM INJURY AND OTHER NEURAL DISORDERS," filed Nov. 19, 2010, which is a continuation of U.S. Ser. No. 12/822,560, filed Jun. 24, 2010, which is a continuation-in-part of U.S. Ser. No. 12/137,194, filed Jun. 11, 2008, now abandoned, which is a divisional of U.S. Ser. No. 11/107,248, filed Apr. 15, 2005, now U.S. Pat. No. 7,396,654, which claims the benefit of U.S. Provisional Application Ser. No. 60/562,944, filed Apr. 15, 2004.

U.S. patent application Ser. No. 12/685,822, entitled "Biomarkers of liver injury," filed Jan. 12, 2010, which is a continuation-in-part of U.S. Ser. No. 11/396,406, filed Mar. 31, 2006, now U.S. Pat. No. 7,645,584, which claims the benefit of U.S. provisional Ser. No. 60/668,121, filed Apr. 1, 2005.

U.S. patent application Ser. No. 12/535,960, entitled "Synaptotagmin And Collapsin Response Mediator Protein As Biomarkers For Traumatic Brain Injury," filed Aug. 5, 2009, which is a continuation-in-part of International Application No. PCT/US2008/001644, filed Feb. 6, 2008, which claims priority from U.S. Provisional Application Ser. No. 60/888,432, filed Feb. 6, 2007.

U.S. patent application Ser. No. 12/137,156, entitled "Proteolytic Markers as Diagnostic Biomarkers for Cancer, Organ Injury and Muscle Rehabilitation/Exercise Overtraining," filed Jun. 11, 2008, which is a divisional of U.S. Ser. No. 11/106,932, filed Apr. 15, 2005, which claims the priority of U.S. Provisional Patent application No. 60/562,819 filed Apr. 15, 2004.

U.S. patent application Ser. No. 11/914,003, entitled "Imaging of Neural and Organ Injury or Damage," filed Jun. 26, 2008, which is a national entry of International Application No. PCT/US2006/018222, filed May 11, 2006, which claims priority from U.S. Provisional Patent application No. 60/680,282, filed May 11, 2005.

U.S. patent application Ser. No. 11/666,397, entitled "Real-Time Assessment of Biomarkers for Disease," filed Oct. 27, 2005, which is a national entry of International Application No. PCT/US05/39037, filed Oct. 27, 2005, which claims priority from U.S. Provisional Patent application No. 60/622,381, filed Oct. 27, 2004.

U.S. patent application Ser. No. 11/551,141, entitled "Multidimensional Protein Separation," filed Oct. 19, 2006, which is a continuation-in-part of PCT application number PCT/US2005/013016, entitled "MULTIDIMENSIONAL PROTEIN SEPARATION" filed Apr. 19, 2005, which claims priority to U.S. provisional application No. 60/563,396, entitled "COMBINED CATIONIC ANIONIC EXCHANGE TANDEM GEL ELECTROPHORESIS PROTEIN SEPARATION," filed Apr. 19, 2004.

U.S. Pub. App. No. 2005/0260654, entitled "Neural proteins as biomarkers for nervous system injury and other neural disorders," published Nov. 24, 2005.

The entire contents and disclosures of these patent applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 29, 2017, is named T2315-22747US01_sequence listing_ST25.txt and is 12 kb in size.

BACKGROUND

Field of the Invention

The disclosed invention relates generally to products and methods for detecting and treating tauopathy-related neurodegenerative disorders.

Related Art

There are almost 1.9 million new cases of traumatic brain injury (TBI) incidents each year in the USA. In addition, over 5 million of the US population might be living with some forms of chronic issues due to traumatic brain injury (TBI). It is increasingly recognized that TBI is a complex, heterogeneous disorder. For example, repetitive concussion o mild TBI might result in brain protein (tau) aggregate accumulation over time, leading to neurodegenerative condition called chronic traumatic encephalopathy. There are other tauopathy human diseases—including Alzheimer's disease.

Tau protein is a microtubule associate protein enriched in the axons of neurons in the central nervous system. Tau is known to promote the assembly of microtubules (MT) and to maintain microtubule integrity in neurons. It is found that hyperphosphorylation of tau would cause it to dissociate form the MT and to form aggregate and filaments, which result in death of the neurons. Such phenomenon is termed tauopathy and is found to be pathologically involved in several neurodegenerative disorders, such as Alzheimer's disease and chronic traumatic encephalopathy.

It has been reported that the levels of total tau and phosphorylated tau in cerebrospinal fluid (CSF) highly correlate to the progression of Alzheimer's disease. However, current methods to detect total tau and phosphorylated tau, including mass spectrometry, positron emission tomography (PET) imaging, and western blotting in combination with immunoprecipitation or highperformance liquid chromatography (HPLC), usually require a sufficiently large amount of sample to overcome the detection limit and are either too costly or too tedious to operate. Currently, there have been no tau-binding agent such as DNA aptamar in market yet.

SUMMARY

According to a first broad aspect, the disclosed invention provides a DNA aptamer comprising a nucleic acid sequence that is capable of specifically binding to a tau protein at a phosphorylatable site of the tau protein; wherein the nucleic acid sequence comprises 66 nucleotides and is selected from the group consisting of SEQ ID NO: 1, SEQ ID NO: 2, SEQ ID NO: 3, SEQ ID NO: 4, SEQ ID NO: 5, SEQ ID NO: 6, and SEQ ID NO: 7.

According to a second broad aspect, the disclosed invention provides a DNA aptamer comprising a nucleic acid sequence that is capable of specifically binding to a tau protein at a phosphorylatable site of the tau protein; wherein the nucleic acid sequence is selected from the group consisting of SEQ ID NO: 8, SEQ ID NO: 9, SEQ ID NO: 10, and SEQ ID NO: 11; and wherein the nucleic acid sequence is a truncated fragment of a nucleic acid sequence set forth in SEQ ID NO: 1.

According to a third broad aspect, the disclosed invention provides a DNA aptamer comprising a nucleic acid sequence that is capable of specifically binding to a tau protein at a phosphorylatable site of the tau protein; wherein the nucleic acid sequence is selected from the group consisting of SEQ ID NO: 12, SEQ ID NO: 13, SEQ ID NO: 14, SEQ ID NO: 15, and SEQ ID NO: 16; and wherein the nucleic acid sequence is a truncated fragment of a nucleic acid sequence set forth in SEQ ID NO: 2.

According to a forth broad aspect, the disclosed invention provides a DNA aptamer comprising a nucleic acid sequence that is capable of specifically binding to a tau protein at a phosphorylatable site of the tau protein; wherein the nucleic acid sequence is selected from the group consisting of SEQ ID NO: 17, SEQ ID NO: 18, and SEQ ID NO: 19; and wherein the nucleic acid sequence is a truncated fragment of a nucleic acid sequence set forth in SEQ ID NO: 3.

According to a fifth broad aspect, the disclosed invention provides a DNA aptamer comprising a nucleic acid sequence that is capable of specifically binding to a tau protein at a phosphorylatable site of the tau protein; wherein the nucleic acid sequence is selected from the group consisting of SEQ ID NO: 20, SEQ ID NO: 21, and SEQ ID NO: 22; wherein the nucleic acid sequence is a truncated fragment of a nucleic acid sequence set forth in SEQ ID NO: 4.

According to a sixth broad aspect, the disclosed invention provides a DNA aptamer comprising a nucleic acid sequence that is capable of specifically binding to a tau protein at a phosphorylatable site of the tau protein; wherein the nucleic acid sequence is selected from the group consisting of SEQ ID NO: 23, SEQ ID NO: 24, and SEQ ID NO: 25; and wherein the nucleic acid sequence is a truncated fragment of a nucleic acid sequence set forth in SEQ ID NO: 5.

According to a seventh broad aspect, the disclosed invention provides a DNA aptamer comprising a nucleic acid sequence that is capable of specifically binding to a tau protein at a phosphorylatable site of the tau protein; wherein the nucleic acid sequence is selected from the group consisting of SEQ ID NO: 26 and SEQ ID NO: 27; and wherein the nucleic acid sequence is a truncated fragment of a nucleic acid sequence set forth in SEQ ID NO: 6.

According to an eighth broad aspect, the disclosed invention provides a composition comprising a DNA aptamer that is capable of specifically binding to a tau protein at a phosphorylatable site of the tau protein, wherein the DNA aptamer comprises a nucleic acid sequence comprising 66 nucleotides and is selected from the group consisting of SEQ ID NO: 1, SEQ ID NO: 2, SEQ ID NO: 3, SEQ ID NO: 4, SEQ ID NO: 5, SEQ ID NO: 6, and SEQ ID NO: 7.

According to a ninth broad aspect, the disclosed invention provides a composition comprising a DNA aptamer that is capable of specifically binding to a tau protein at a phosphorylatable site of the tau protein, wherein the DNA aptamer comprises a nucleic acid sequence selected from the group consisting of SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and SEQ ID NO: 27.

According to a tenth broad aspect, the disclosed invention provides a kit for testing the presence or progression of various tauopathy diseases comprising a DNA aptamer and a tau-binding antibody, wherein the DNA aptamer that is capable of specifically binding to a tau protein at a phosphorylatable site of the tau protein.

According to an eleventh broad aspect, the disclosed invention provides a DNA aptamer conjugate comprising: a signaling moiety conjugated a DNA aptamer that is capable of binding to a tau protein at a phosphorylatable site of the tau protein, wherein the DNA aptamer comprises a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and SEQ ID NO: 27.

According to a twelve broad aspect, the disclosed invention provides a DNA aptamer conjugate comprising: a DNA aptamer that is capable of binding to a tau protein at a phosphorylatable site of the tau protein, and an azido-containing cell penetrating peptide linked to the DNA aptamer, wherein the DNA aptamer comprises a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and SEQ ID NO: 27.

According to a thirteen broad aspect, the disclosed invention provides a method of detecting the presence or progression of a tauopathy disease comprising measuring binding of a DNA aptamer to a phosphorylated tau protein, a non-phosphorylated tau, or a total tau protein in a biosample obtained from a subject, thereby determining a level of tau and phosphor-tau in the biosample, wherein the level of tau and phosphor-tau indicates whether a tauopathy disease is present.

According to a fourteenth broad aspect, the disclosed invention provides a method for cell-based imaging of phosphorylated tau, non-phosphorylated tau, and/or total tau in a cell comprising: introducing a DNA aptamer conjugate into a cell in a cell culture medium; and detecting the binding of the DNA aptamer conjugate to a tau protein in the cell; wherein the DNA aptamer conjugate comprises a modified DNA aptamer that is linked with an azido-containing cell penetrating peptide; wherein the modified DNA aptamer is capable of binding to a tau protein at a phosphorylatable site of the tau protein; and wherein the DNA aptamer comprises a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and SEQ ID NO: 27.

According to a fifteenth broad aspect, the disclosed invention provides a method for in vivo imaging of phosphorylated tau, non-phosphorylated tau, and/or total tau in a subject comprising: delivering a composition comprising a DNA aptamer conjugate into a subject in need thereof; and detecting the binding of the DNA aptamer conjugate to a tau protein in the subject; wherein the DNA aptamer conjugate comprises a modified DNA aptamer that is linked with an azido-containing cell penetrating peptide; and wherein the DNA aptamer comprises a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and SEQ ID NO: 27.

According to a sixteenth broad aspect, the disclosed invention provides a method for in vivo imaging of phosphorylated tau, non-phosphorylated tau, and/or total tau in a subject comprising: delivering a composition comprising a DNA aptamer conjugate into a subject in need thereof; and detecting the binding of the DNA aptamer conjugate to a tau protein in the subject; wherein the DNA aptamer conjugate comprises a DNA aptamer conjugated to a moiety, wherein the moiety is a reporter molecule can be a molecular becon, fluorescent tag, a radioisotope for positron emission tomography (PET), single-photon emission computed tomography (SPECT), and/or contrast-agent-based MRI; and wherein the DNA aptamer comprises a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and SEQ ID NO: 27.

According to a seventeenth broad aspect, the disclosed invention provides a method for treating a progression of tauopathy associated neurodegenerative disorder comprising administering to a subject in need thereof a composition comprising a therapeutically effective amount of a DNA aptamer that is capable of binding to a tau protein at a phosphorylatable site of the tau protein, wherein when the DNA aptamer binds to a tau protein, the DNA aptamer is capable of inhibiting tau phosphorylation and tau protein oligomerization and/or aggregation in the brain of the subject.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIGS. 7A, 7B, 7C and 7D illustrate binding test with reference sequences, according to an embodiment of the disclosed invention.

FIGS. 12A through 12J illustrate primary binding analysis between the top 10 aptamer candidates and their prospective target of peptides, according to an embodiment of the disclosed invention.

FIG. 13A includes IT1 (SEQ ID NO: 1); IT1a (SEQ ID NO: 8); IT1b (SEQ ID NO: 9); IT1c (SEQ ID NO: 10); and IT1d (SEQ ID NO: 11).

FIG. 14A includes IT2 (SEQ ID NO: 2), IT2a (SEQ ID NO: 12); IT2b(1) (SEQ ID NO: 13); IT2b(2) (SEQ ID NO: 50); IT2c (SEQ ID NO: 14); IT2d (SEQ ID NO: 15); and IT2e (SEQ ID NO: 16).

FIG. 15A includes IT3 (SEQ ID NO: 3); IT3a (SEQ ID NO: 17); IT3b (SEQ ID NO: 18); and IT3c (SEQ ID NO: 19).

FIG. 16A includes IT4 (SEQ ID NO: 4); IT4a (SEQ ID NO: 20); IT4b (SEQ ID NO: 21); and IT4c (SEQ ID NO: 22).

FIG. 17A includes IT5 (SEQ ID NO: 5); IT5a (SEQ ID NO: 51); IT5b (SEQ ID NO: 24); and IT5c (SEQ ID NO: 52).

FIG. 18A included IT6 (SEQ ID NO: 6); IT6a (SEQ ID NO: 26); and IT6b (SEQ ID NO: 27).

FIG. 21 illustrates the derivation of Equation 3-7 used in the association phase, according to an embodiment of the disclosed invention.

FIG. 22 illustrates the derivation of Equation 3-8 used in the steady state, according to an embodiment of the disclosed invention.

FIG. 23 illustrates the derivation of Equation 3-9 used in the dissociation phase, according to an embodiment of the disclosed invention.

FIGS. 27A and 27B illustrate aptamer-based molecular beacons labeled with quencher Q and fluorophore F for detection of tau protein, according to an embodiment of the disclosed invention.

FIG. 31 is a table showing the sequence truncation of some tau aptamers, and their preferred binding to specific tau epitopes, according to an embodiment of the disclosed invention.

DETAILED DESCRIPTION OF THE PREFERRED EMBODIMENTS

Definitions

Figure 1:
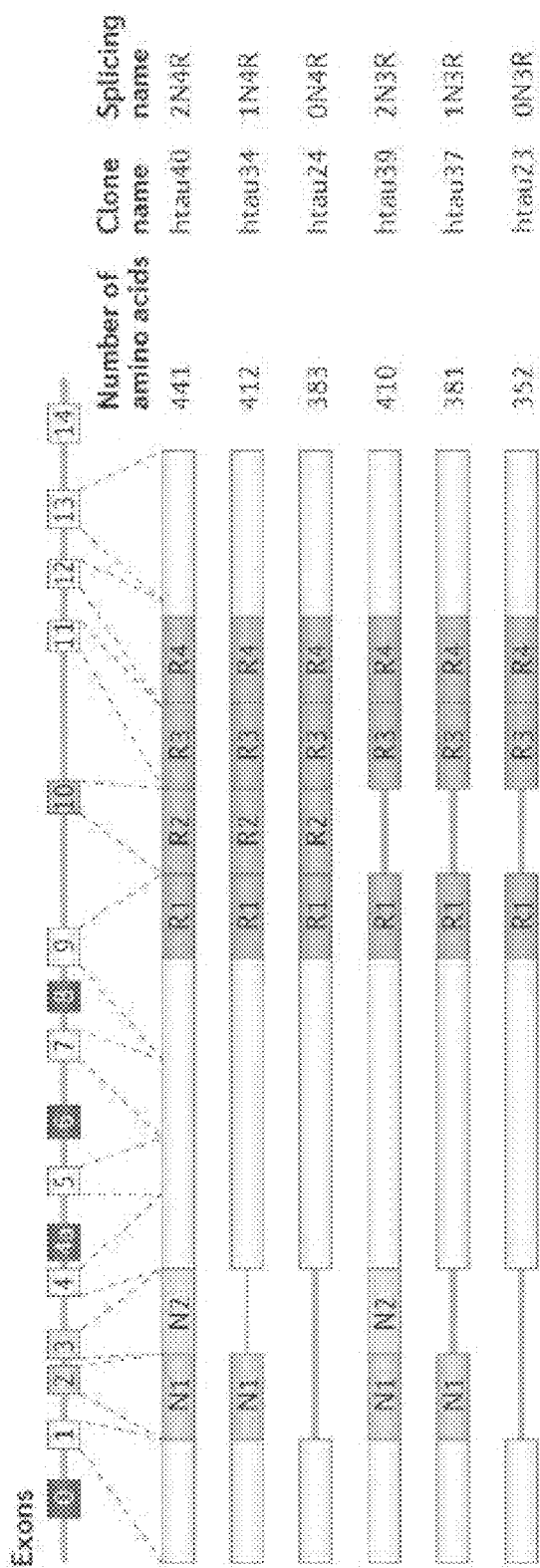
FIG. 1 illustrates the human MAPT gene and the splice isoforms of tau in the human brain.

Where the definition of terms departs from the commonly used meaning of the term, applicant intends to utilize the definitions provided below, unless specifically indicated.

Unless defined otherwise, all technical and scientific terms used herein have the same meaning as is commonly understood to which the claimed subject matter belongs. In the event that there is a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise.

For purposes of the disclosed invention, a value or property is "based" on a particular value, property, the satisfaction of a condition, or other factor, if that value is derived by performing a mathematical calculation or logical decision using that value, property or other factor.

For purpose of the disclosed invention, the term "adjacent" refers to "next to" or "adjoining something else."

For purposes of the disclosed invention, the term "comprising", the term "having", the term "including," and variations of these words are intended to be open-ended and mean that there may be additional elements other than the listed elements.

For purposes of the disclosed invention, directional terms such as "top," "bottom," "upper," "lower," "above," "below," "left," "right," "horizontal," "vertical," "up," "down," etc., are used merely for convenience in describing the various embodiments of the disclosed invention. The embodiments of the disclosed invention may be oriented in various ways. For example, the diagrams, apparatuses, etc., shown in the drawing figures may be flipped over, rotated by 90° in any direction, reversed, etc.

For purposes of the disclosed invention, the term "toward" refers to decreasing the distance between two aligned objects. For example, a contact controlling positioning device may be used to move: a stamp towards an ink palette, an ink palette towards a stamp, a stamp towards a substrate, a substrate towards a stamp, etc.

For purposes of the disclosed invention, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

For purpose of the disclosed invention, the term "linked" refers to a covalent linkage between two polypeptides in a fusion protein. The polypeptides are typically joined via a peptide bond, either directly to each other or via one or more additional amino acids.

For purpose of the disclosed invention, the term "linker" refers to short peptide sequences that occur between functional protein domains and link the functional domains together. Linkers designed by researchers are generally classified into three categories according to their structures: flexible linkers, rigid linkers, and in vivo cleavable linkers. A flexible linker is often composed of flexible residues like glycine and serine so that the adjacent protein domains are free to move relative to one another. A linker also may play a role in releasing the free functional domain in vivo (as in in vivo cleavable linkers). Linkers may offer many other advantages for the production of fusion proteins, such as improving biological activity, increasing expression yield, and achieving desirable pharmacokinetic profiles. The composition and length of a linker may be determined in accordance with methods well known in the art and may be tested for efficacy.

For purpose of the disclosed invention, the term "domain" with respect to a protein refers to a distinct functional or structural unit in the protein. Usually, a protein domain is responsible for a particular function or interaction, contributing to the overall role of a protein. Domains may exist in a variety of biological contexts, where similar domains can be found in proteins with different functions.

For purposes of the disclosed invention, the term "analog" refers to a compound with similar properties.

For purposes of the disclosed invention, the term "analyte" refers to the conventional meaning of the term "analyte," i.e., a substance or chemical constituent of a sample that is being detected or measured in a sample.

For purposes of the disclosed invention, the term "animal" refers to humans as well as non-human animals. Preferably, the non-human animal is a mammal (e.g., a rodent, a mouse, a rat, a rabbit, a monkey, a dog, a cat, a primate, or a pig). An animal may be a domesticated animal. An animal may be a transgenic animal.

For purposes of the disclosed invention, the term "antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'2 fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, CH1, CH2 and CH3, but does not include the heavy chain variable region.

For purposes of the disclosed invention, the term "aptamer" and the term "DNA aptamer" refer to an oligonucleotide molecule that binds to a target protein. In some embodiment, the aptamer or the DNA aptamer bind to a specific region or amino acid sequence of the target protein. In embodiments of the disclosed invention, "tau aptamer" are DNA aptamer that can binds to a tau protein at a phosphorylatable site.

For purposes of the disclosed invention, the term "bind," the term "binding" or the term "bound" refers to any type of chemical or physical binding, which includes but is not limited to covalent binding, hydrogen binding, electrostatic binding, biological tethers, transmembrane attachment, cell surface attachment and expression.

For purposes of the disclosed invention, the term "carrier" refers to relatively nontoxic chemical compounds or agents that facilitate the incorporation of a compound of interest such as naltrexone, methylphenidate, etc., into organisms.

For purposes of the disclosed invention, the term "conjugate" refers to connected, coupled, or linked. In particular, a DNA aptamer conjugate refers to a DNA aptamer connected, coupled, or linked with another molecule such as a reporter molecule, or a signaling moiety.

For purposes of the disclosed invention, the term "complementary" and the term "complementarity" refer to polynucleotides (e.g., a sequence of nucleotides) related by the base-pairing rules. For example, a DNA sequence 5'-A-G-T-3' is complementary to a DNA sequence 3'-T-C-A-5' or a RNA sequence 3'-U-C-A-5'.

For purposes of the disclosed invention, the term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., (1993) J. Gen. Microbiol. 139:425-32) can be modified to yield a functionally identical molecule. Accordingly, each silent variation of a nucleic acid, which encodes a polypeptide of the disclosed invention, is implicit in each described polypeptide sequence and incorporated herein by reference.

For purposes of the disclosed invention, the term "control amount" of a marker refers to any amount or a range of amount which is to be compared against a test amount of a marker. For example, a control amount of a marker can be the amount of a marker in a person without neural injury and/or neuronal disorder. A control amount can be either in absolute amount (e.g., µg/ml) or a relative amount (e.g., relative intensity of signals).

For purposes of the disclosed invention, the term "correspond" and the term "corresponding" refer to that a protein sequence refer interchangeably to an amino acid position(s) of a protein. An amino acid at a position of a protein may be found to be equivalent or corresponding to an amino acid at a position of one or more other protein(s) based on any relevant evidence, such as the primary sequence context of the each amino acid, its position in relation to the N-terminal and C-terminal ends of its respective protein, the structural and functional roles of each amino acid in its respective protein, etc.

For purposes of the disclosed invention, the term "detect" refers to identifying the presence, absence or amount of the object to be detected.

For purposes of the disclosed invention, the term "detectable moiety" or the term "label" refers to a composition detectable by spectroscopic, photochemical, biochemical, immunochemical, or chemical means. For example, useful labels include 32P, 35S, fluorescent dyes, electron-dense reagents, enzymes (e.g., as commonly used in an ELISA), biotin-streptavidin, digoxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantify the amount of bound detectable moiety in a sample. Quantitation of the signal is achieved by, e.g., scintillation counting, densitometry, or flow cytometry.

For purposes of the disclosed invention, the term "diagnostic" refers to identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

For purposes of the disclosed invention, the phrase "diagnostic amount" of a marker refers to an amount of a marker in a subject's sample that is consistent with a diagnosis of neural injury and/or neuronal disorder. A diagnostic amount can be either in absolute amount (e.g., µg/ml) or a relative amount (e.g., relative intensity of signals).

For purposes of the present invention, the term "dosage form," the term "form," and the term "unit dose" refer to a method of preparing pharmaceutical products in which individual doses of medications are prepared and delivered. Dosage forms typically involve a mixture of active drug components and nondrug components (excipients), along with other non-reusable material that may not be considered either ingredient or packaging.

For purposes of the present invention, the term "dosage" refers to the administering of a specific amount, number, and frequency of doses over a specified period of time. Dosage implies duration. A "dosage regimen" is a treatment plan for administering a drug over a period of time.

For purposes of the present invention, the term "dose" refers to a specified amount of medication taken at one time.

For purposes of the present invention, the term "drug" refers to a material that may have a biological effect on a cell, including but not limited to small organic molecules, inorganic compounds, polymers such as nucleic acids, peptides, saccharides, or other biologic materials, nanoparticles, etc.

For purposes of the present invention, the term "effective amount" or "effective dose" or grammatical variations thereof refers to an amount of an agent sufficient to exhibit one or more desired effects. The effective amount may be determined by a person skilled in the art using the guidance provided herein.

For purposes of the present invention, the term "eluant" and the term "washing solution" are interchangeable and refer to an agent that can be used to mediate adsorption of a marker to an adsorbent. Eluants and washing solutions are also referred to as "selectivity threshold modifiers." Eluants and washing solutions can be used to wash and remove unbound materials from the probe substrate surface.

For purposes of the present invention, the term "excipient" refers to a natural or synthetic substance formulated alongside the active ingredient of a medication, included for the purpose of bulking-up formulations that contain potent active ingredients (thus often referred to as "bulking agents," "fillers," or "diluents"), or to confer a therapeutic enhancement on the active ingredient in the final dosage form, such as facilitating drug absorption or solubility. Excipients can also be useful in the manufacturing process, to aid in the handling of the active substance concerned such as by facilitating powder flowability or non-stick properties, in addition to aiding in vitro stability such as prevention of denaturation over the expected shelf life. The selection of appropriate excipients also depends upon the route of administration and the dosage form, as well as the active ingredient and other factors. Though excipients were at one time considered to be "inactive" ingredients, they are now understood to be a key determinant of dosage form performance,"

For purposes of the disclosed invention, the phrase "differentially present" refers to differences in the quantity and/or the frequency of a marker present in a sample taken from patients having for example, neural injury as compared to a control subject. For example, a marker can be a polypeptide which is present at an elevated level or at a decreased level in samples of patients with neural injury compared to samples of control subjects. Alternatively, a marker can be a polypeptide which is detected at a higher frequency or at a lower frequency in samples of patients compared to samples of control subjects. A marker can be differentially present in terms of quantity, frequency or both. A polypeptide is differentially present between the two samples if the amount of the polypeptide in one sample is statistically significantly different from the amount of the polypeptide in the other sample. For example, a polypeptide is differentially present between the two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other. Alternatively or additionally, a polypeptide is differentially present between the two sets of samples if the frequency of detecting the polypeptide in samples of patients' suffering from neural injury and/or neuronal disorders, is statistically significantly higher or lower than in the control samples. For example, a polypeptide is differentially present between the two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

For purposes of the disclosed invention, the term "fragment" of a molecule such as a protein or nucleic acid refers to a portion of the amino acid or nucleotide sequence.

For purposes of the present invention, the term "gene" refers to a nucleic acid (e.g., DNA or RNA) sequence that comprises coding sequences necessary for the production of an RNA or a polypeptide or its precursor. The term "portion," when used in reference to a gene, refers to fragments of that gene. The fragments may range in size from a few nucleotides to the entire gene sequence minus one nucleotide. Thus, "a nucleotide comprising at least a portion of a gene" may comprise fragments of the gene or the entire gene.

For purposes of the present invention, the term "gene expression" refers to a process by which information from a gene is used the synthesis of a functional gene product. A gene product is often a protein, but in a non-protein coding gene such as transfer RNA (tRNA) or small nuclear RNA (snRNA) gene, the product is a functional RNA.

For purposes of the present invention, the term "gene therapy" refers to the purposeful delivery of genetic material to cells for the purpose of treating disease or biomedical investigation and research. Gene therapy includes the delivery of a polynucleotide to a cell to express an exogenous nucleotide sequence, to inhibit, eliminate, augment, or alter expression of an endogenous nucleotide sequence, or to produce a specific physiological characteristic not naturally associated with the cell. In some cases, the polynucleotide itself, when delivered to a cell, can alter expression of a gene in the cell.

For purposes of the disclosed invention, the term "heterologous," when used in relation to a nucleic acid, includes reference to a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

For purposes of the disclosed invention, the term "introduce," when used in relation to a nucleic acid, refers to delivering a nucleic acid into a cell or a subject.

For purposes of the disclosed invention, the term "isolated," "isolated nucleic acid," or "isolated protein," includes reference to a material, such as a nucleic acid or a protein, which is substantially or essentially free from components which normally accompany or interact with it as found in its naturally occurring environment. The isolated material optionally comprises material not found with the material in its natural environment.

For purposes of the present invention, the term "immunoassay" is an assay that uses an antibody to specifically bind an antigen (e.g., a marker). The immunoassay is characterized by the use of specific binding properties of a particular antibody to isolate, target, and/or quantify the antigen.

For purposes of the present invention, the term "individual" refers to an individual mammal, such as a human being.

For purposes of the present invention, the term "inhibiting" refers to the onset of a disorder means either lessening the likelihood of the disorder's onset, preventing the onset of the disorder entirely, or in some cases, reducing the severity of the disease or disorder after onset. In the preferred embodiment, inhibiting the onset of a disorder means preventing its onset entirely.

For purposes of the present invention, the term "intraperitoneal injection" or the term "IP injection" refer to the injection of a substance into the peritoneum.

For purposes of the disclosed invention, the term "marker" refers to a polypeptide (of a particular apparent molecular weight) which is differentially present in a sample taken from patients having neural injury and/or neuronal disorders as compared to a comparable sample taken from control subjects (e.g., a person with a negative diagnosis, normal or healthy subject).

For purposes of the present invention, the term "medical therapy" refers to prophylactic, diagnostic and therapeutic regimens carried out in vivo or ex vivo on humans or other mammals.

For purposes of the present invention, the term "modified" and the term "mutant" when made in reference to a gene or to a gene product refer, respectively, to a gene or to a gene product which displays modifications in sequence and/or functional properties (i.e., altered characteristics) when compared to the wild-type gene or gene product.

For purposes of the disclosed invention, the term "mutant protein" refers to a protein product encoded by a gene with mutation.

For purposes of the disclosed invention, the phrase "Neural cells" refers to the cells that reside in the brain, central and peripheral nerve systems, including, but not limited to, nerve cells, glial cell, oligodendrocyte, microglia cells or neural stem cells.

For purposes of the disclosed invention, the phrase "neuronal specific or neuronally enriched proteins" refers to proteins that are present in neural cells and not in non-neuronal cells, such as, for example, cardiomyocytes, myocytes, in skeletal muscles, hepatocytes, kidney cells and cells in testis.

For purposes of the disclosed invention, the term "nucleic acid" and the term "polynucleotide," as used interchangeably herein, include reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

For purposes of the present invention, the term "oligonucleotide," the term "polynucleotide," the term "nucleotide," and the term "nucleic acid" refer to a molecule comprised of two or more deoxyribonucleotides or ribonucleotides, and usually more than ten. The exact size of an oligonucleotide will depend on many factors, which in turn depends on the ultimate function or use of the oligonucleotide. The oligonucleotide may be generated in any manner, including chemical synthesis, DNA replication, reverse transcription, or a combination thereof. When present in a DNA form, the oligonucleotide may be single-stranded (i.e., the sense strand) or double-stranded.

For purposes of the present invention, the term "parenteral route" refers to the administration of a composition, such as a drug in a manner other than through the digestive tract. Parenteral routes include, but are not limited to, routes such as intravenous, intra-arterial, transdermal, intranasal, sub-lingual and intraosseous, etc. For example, intravenous is also known as I.V., which is giving directly into a vein with injection. As the drug directly goes into the systemic circulation, it reaches the site of action resulting in the onset the action.

For purposes of the disclosed invention, the term "percentage of sequence identity" refers to the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

For purposes of the present invention, the term "pharmaceutical composition" refers to a product comprising one or more disclosed tau protein-binding DNA aptamers, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. A pharmaceutical composition includes enough of the active object compound to produce the desired effect upon the progress or condition of diseases. Accordingly, a pharmaceutical composition encompasses any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof, i.e., the subject.

For purposes of the present invention, the term "pharmaceutical formulation" and the term "drug formulation" refer to a mixtures or a structure in which different chemical substances, including the active drug, are combined to form a final medicinal product, such as a sterile product, a capsule, a tablet, a powder, a granule, a solution, an emulsion, a topical preparation, a non-conventional product such as semi-solid or sustained-release preparations, liquid, etc. Pharmaceutical formulation is prepared according to a specific procedure, a "formula." The drug formed varies by the route of administration. For example, oral drugs are normally taken as tablet or capsules.

For purposes of the present invention, the term "pharmaceutically acceptable" refers to a compound or drug approved or approvable by a regulatory agency of a federal or a state government, listed or listable in the U.S. Pharmacopeia or in other generally recognized pharmacopeia for use in mammals, including humans. For example, a "pharmaceutically acceptable diluent, excipient, carrier, or adjuvant" is a diluent, excipient, carrier, or adjuvant which is physiologically acceptable to the subject while retaining the therapeutic properties of the pharmaceutical composition with which it is administered. One exemplary pharmaceutically acceptable carrier is physiological saline.

For purposes of the present invention, the term "pharmaceutically acceptable salt" refers to those salts that are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. They may be prepared in situ when finally isolating and purifying the compounds of the invention, or separately by reacting them with pharmaceutically acceptable non-toxic bases or acids, including inorganic or organic bases and inorganic or organic acids. Pharmaceutically acceptable salts may be obtained using standard procedures well known in the art, for example by mixing a compound of the present invention with a suitable acid, for instance an inorganic acid or an organic acid.

For purposes of the present invention, the term "pharmaceutically acceptable carrier" refers to any carrier that does not itself induce the production of antibodies harmful to an individual or a subject receiving a composition. For example, pharmaceutically acceptable carriers may be large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art.

For purposes of the disclosed invention, the term "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

For purposes of the disclosed invention, the term "polypeptide" and the term "protein" are used interchangeably herein to refer to a polymer of amino acid residues. The terms encompass amino acid polymers in which one or more amino acid residues are artificial chemical mimetic of a corresponding naturally occurring amino acids, as well as to naturally occurring amino acid polymers and non-naturally occurring amino acid polymer. Polypeptides can be modified, e.g., by the addition of carbohydrate residues to form glycoproteins. The terms "polypeptide," "peptide" and "protein" include glycoproteins, as well as non-glycoproteins.

For purposes of the disclosed invention, the term "purified" refers to the component in a relatively pure state.

For purposes of the present invention, the term "prevent" refers to stop from happening or to make something not happen.

For purposes of the disclosed invention, the term "probe" refers to nucleic acid molecule that can bind to a protein target.

For purposes of the disclosed invention, the term "recombinant" refers to a genetic material formed by a genetic recombination process. A "recombinant protein is made through genetic engineering. A recombinant protein is coded by a DNA sequence created artificially. A recombinant protein is a protein that is coded by a recombinant nucleic acid sequence. A recombinant nucleic acid sequence has a sequence from two or more sources incorporated into a single molecule.

For purposes of the disclosed invention, the term "reference sequence" refers to a defined sequence used as a basis for sequence comparison. A reference sequence may be a subset or the entirety of a specified sequence; for example, as a segment of a full-length cDNA or gene sequence, or the complete cDNA or gene sequence.

For purposes of the disclosed invention, the term "reporter" or the term "reporter molecule" refers to a molecule that is used for detecting a signal of analyzed molecules in an experiment, testing, or assay. A reporter molecule can be a molecular becon, fluorescent tag, a radioisotope for SPECT or PET, etc.

For purposes of the disclosed invention, the term "residue," the term "amino acid residue," or the term "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

For purposes of the disclosed invention, the term "resolve," the term "resolution," or the term "resolution of marker" refers to the detection of at least one marker in a sample. Resolution includes the detection of a plurality of markers in a sample by separation and subsequent differential detection. Resolution does not require the complete separation of one or more markers from all other biomolecules in a mixture. Rather, any separation that allows the distinction between at least one marker and other biomolecules suffices.

For purposes of the disclosed invention, the term "room temperature" refers to a temperature of from about 20° C. to about 25° C.

For purposes of the disclosed invention, the term "sample" is used herein in its broadest sense. A sample comprising polynucleotides, polypeptides, peptides, antibodies and the like and may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

For purposes of the disclosed invention, the term "sequence identity" or the term "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, Calif., USA).

For purposes of the disclosed invention, the phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to marker NF-200 from specific species such as rat, mouse, or human can be selected to obtain only those polyclonal antibodies that are specifically immunoreactive with marker NF-200 and not with other proteins, except for polymorphic variants and alleles of marker NF-200. This selection may be achieved by subtracting out antibodies that cross-react with marker NF-200 molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

For purposes of the disclosed invention, the term "subject" and the term "patient" refers to an animal, which is the object of treatment, observation or experiment. By way of example only, a subject may be, but is not limited to, a mammal including, but not limited to, a human.

For purposes of the disclosed invention, the term "substantial identity" refers to that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides which are "substantially similar" share sequences as noted above, except that residue positions which are not identical may differ by conservative amino acid changes. One of skill will recognize that these values can be appropriately adjusted to determine corresponding identity of proteins encoded by two nucleotide sequences by taking into account codon degeneracy, amino acid similarity, reading frame positioning and the like. Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

For purposes of the disclosed invention, the term "substantially purified" refers to nucleic acid molecules or proteins that are removed from their natural environment and are isolated or separated, and are at least about 60% free, preferably about 75% free, and most preferably about 90% free, i.e. from about 60% to about 90%, from other components with which they are naturally associated.

For purposes of the disclosed invention, the term "substrate" or the term "probe substrate" refers to any rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

For purposes of the disclosed invention, the term "substantially purified" refers to nucleic acid molecules or proteins that are removed from their natural environment and are isolated or separated, and are at least about 60% free, preferably about 75% free, and most preferably about 90% free, i.e. from about 60% to about 90%, from other components with which they are naturally associated.

For purposes of the disclosed invention, the term "subunit" refers to a separate polypeptide chain that makes a certain protein which is made up of two or more polypeptide chains joined together. In a protein molecule composed of more than one subunit, each subunit can form a stable folded structure by itself. The amino acid sequences of subunits of a protein can be identical, similar, or completely different.

For purposes of the present invention, the term "target" refers to a biological molecule to which some other entity, such as a molecule like an aptamer or a DNA fragment, is directed and/or binds. For example, "target protein" may a biological molecule, such as a protein or protein complex, a receptor, or a portion of a biological molecule, etc., capable of being bound and regulated by a biologically active composition such as a pharmacologically active drug compound derived from a protein binding DNA-aptamer.

For purposes of the present invention, the term "therapeutically effective amount" refers to an amount of a compound or composition that, when administered to a subject for treating a disease or disorder, or at least one of the clinical symptoms of a disease or disorder, is sufficient to affect such disease, disorder, or symptom. A "therapeutically effective amount" may vary depending, for example, on the compound, the disease, disorder, and/or symptoms of the disease or disorder, severity of the disease, disorder, and/or symptoms of the disease or disorder, the age, weight, and/or health of the subject to be treated, the capacity of the individual's immune system to synthesize antibodies, the degree of protection desired, the formulation of the vaccine, the treating doctor's assessment of the medical situation, and other relevant factors. An appropriate amount in any given instance may be readily ascertained by those skilled in the art or capable of determination by routine experimentation. It is expected that the amount will fall in a relatively broad range that can be determined through routine trials.

For purposes of the disclosed invention, the term "test amount" of a marker refers to an amount of a marker present in a sample being tested. A test amount can be either in absolute amount (e.g., µg/ml) or a relative amount (e.g., relative intensity of signals).

For purposes of the present invention, the term "treating" and the term "treatment," when being used in relating to a disease, disorder, or condition, refers to an approach for obtaining beneficial or desired results, such as clinical results. Beneficial or desired results can include, but are not limited to, alleviation or amelioration of one or more symptoms or conditions; diminishment of extent of disease, disorder, or condition; stabilization (i.e., not worsening) of a state of disease, disorder, or condition; prevention of spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

Abbreviations for purposes of the present invention are listed below:
AD Alzheimer's disease
ASW Artificial sea water
BSA Bovine serum albumin
cdk5 Cyclin-dependent kinase-5
CEA Carcinoembryonic antigen
CNS Central nervous system
CPP Cell penetrating peptide
CTE Chronic traumatic encephalopathy
DBCO Dibenzylcyclooctyne
DMEM Dulbecco's modified Eagle's medium
DNA Deoxyribonucleic acid
DTT Dithiothreitol
dNTP Deoxynucleotide triphosphate
EGFR Epidermal growth factor receptor
ELISA Enzyme-linked immunosorbent assay
ER Estrogen receptor
FAM 6-carboxyfluorescein
FITC Fluorescein-5,6-isothiocyanate
GSK-3 Glycogen synthase kinase-3
HER2 Human epidermal growth factor receptor 2
HIV Human immunodeficiency virus
IGF Insulin-like growth factors
IgG Immunoglobulin G
IGHM immunoglobin heavy mu chain
Kd Dissociation constant
kDa Kilodalton
MAPK Mitogen-activated protein kinase
NFTs Neurofibrillary tangles
NTA Nitrilotriacetic acid
PAGE Polyacrylamide gel electrophoresis
PBS Dulbecco's phosphate buffered saline
PCR Polymerase chain reaction
PDGF Platelet-derived growth factor
PHFs Paired helical filaments
PR Progesterone receptor
PRD Proline-rich domain
PSA Prostate specific antigen
PTK7 Protein tyrosine kinase 7
PVDF Polyvinylidene difluoride
RNA Ribonucleic acid
S100B S100 calcium-binding protein B
SDS Sodium dodecyl sulfate
SELEX Systematic evolution of ligands by exponential enrichment
ssDNA Single stranded deoxyribonucleic acid
TAT trans-activator of transcription
TAT CPP derived from the trans-activator of transcription of HIV
TBE Tris/Borate/EDTA
TBI Traumatic brain injury
TBST Tris-buffered saline with Tween 20
TEAA Triethylammonium acetate
HBV hepatitis B virus
HCC Hepatocellular carcinoma
HCV hepatitis C virus
HPLC High performance liquid chromatography
VEGF Vascular enhanced growth factors

DESCRIPTION

While the disclosed invention is susceptible to various modifications and alternative forms, specific embodiment thereof has been shown by way of example in the drawings and will be described in detail below. It should be understood, however that it is not intended to limit the disclosed invention to the particular forms disclosed, but on the contrary, the disclosed invention is to cover all modifications, equivalents, and alternatives falling within the spirit and the scope of the invention.

Through two different approaches, the cell-based SELEX and peptide SELEX, the disclosed invention identifies DNA aptamers targeting hepatocarcinoma associated membrane proteins and neurodegenerative diseases related tau protein, respectively. The disclosed DNA aptamers are capable of recognizing disease-associated targets. Selected aptamers are also used to develop molecular probes.

Nucleic Acid Aptamers

Nucleic acid aptamers are short, single-stranded DNA or RNA oligonucleotides capable of specific binding to defined targets. The term "aptamer" derived from the Latin "aptus", meaning to fit, was firstly introduced back in 1990 when Ellington and Szostak reported the in vitro selection of dye-binding RNA aptamers,[1] while the amplification-evolution process used to select these binding molecules was termed "systematic evolution of ligands by exponential enrichment" (SELEX) by Turek and Gold when they identified two RNA sequences that bind to T4 DNA polymerase from over 60 thousands species using this procedure.[2] Since then, a growing number of RNA and DNA aptamers have been selected against a variety of targets, including metal ions,[3-5] fluorescent dyes,[6] amino acids,[7-9] nucleotides,[10] antibiotics,[11-14] metabolites,[15], [16] peptides,[17], [18] proteins,[19-22] viruses,[23, 24] organelles,[25] or even whole cells.[26, 27] Furthermore, aptamers have shown remarkable specificity in discriminating targets from their similar analogs, such as differentiating among homologous proteins that differed only by a few amino acids[28] or one single amino acid,[29] or even between enantiomers.[30, 31] On the other hand, as oligonucleotides, aptamers are readily reproducible by chemical synthesis. It is also readily easy to chemically introduce functional modules, such as fluorophores,[32-34] chemical linkers,[35, 36] therapeutics,[37-39] or even nanoparticles,[40] onto aptamers to fulfill specific needs.[41, 42]

The specificity and high affinity of aptamers' binding ability toward corresponding targets have made them a new generation of molecular probes. Especially, aptamers have shown outstanding capacity in differentiating specific disease-related proteins, either on the cell membranes or in the body fluids.

Tau aptamers identified here are evolved against peptide fragments from tau bearing predisposition to phosphorylation. Tau proteins are known to promote the assembly of microtubules and to maintain microtubular integrity in neurons. It is found that hyperphosphorylation of tau would cause them to form aggregations and filaments, which result in death of neurons. Such phenomenon is termed tauopathy and is found to be pathologically involved in several neurodegenerative disorders, such as Alzheimer's disease and chronic traumatic encephalopathy. The tau aptamers not only recognize tau at the designated sites, but also demonstrate inhibitory effects on phosphorylation and oligomer formation. These findings validate the feasibility of applying tau aptamers to (1) detect the levels of tau in cerebrospinal fluid, (2) study the mechanism of tauopathy, and (3) arrest the progression of tauopathy associated disorders.

SELEX

The advent and success of SELEX technology in 1990s may be attributed to the feasibility to chemically synthesize pools of random oligonucleotides, the availability of the polymerases for nucleic acid amplification, as well as the improvement in sequencing techniques. The molecular recognition between aptamers and their corresponding targets relies on the three-dimensional conformations of the aptamers, hence the specific nucleic acid sequences. By substituting just a few nucleotides, the conformation of an oligonucleotide may change. Consequently, the structural diversity of a DNA or RNA pool containing combinatorial sequences may be infinitely expanded, thereby creating panels of aptamers for a wide variety of binding targets. Though there are some differences between the procedures for selecting DNA and RNA aptamers, for example, RNA SELEX generally involves additional transcription and reverse transcription while the survivors in DNA SELEX may be directly amplified via PCR followed by strand separation, the evolution process for selecting either DNA or RNA aptamers typically covers the following steps: 1) chemical synthesis of a combinatorial oligonucleotide library having $10^{13}$-$10^{16}$ single stranded nucleic acid molecules, 2) exposure of the library to the targets to differentiate binding strands from spectators, 3) extraction and amplification of eluted survivors, 4) enrichment of the stronger survivors by iterative binding to targets and by involving counter selection if necessary, and, finally, 5) sequencing to identify individual candidates.

Aptamer-Protein Interactions

Many proteins in nature, such as transcription factors and nuclear proteins, are already known to interact with DNA or RNA to perform multiple functions and regulate many cellular processes, including transcription, translation, gene silencing, microRNA biogenesis and telomere maintenance. Even though these interactions are not necessarily strong, they are definitely specific and functional.[43] Unlike these DNA- and RNA-binding proteins, the target proteins used or identified in the process of aptamer evolution are proteins that do not normally interact with nucleic acids but show high affinity to the specific DNA or RNA selected. In these cases, the affinity may be attributed to the topography on the protein surfaces along with the presence of H-bond donors and acceptors as well as the flexible phosphodiester backbone of the nucleic acid folding into precise three-dimensional scaffolds, thus creating hydrophobic and electrostatic interactions, hydrogen bonding, van der Waals forces, and shape complementarity between aptamers and target proteins to assist the recognition.[44] The first example of such a protein is thrombin binding to single-stranded DNA aptamers with a highly conserved region.[19] Binding thrombin with aptamers may also inhibit thrombin activity and decrease the rate of blood clotting.[45] The three-dimensional structure of the aptamer and the thrombin-aptamer complex have been evaluated by NMR[46] and X-ray crystallography[47], respectively. Evidently, aptamers targeting proteins are not only expected to recognize the targets but may also inhibit their down-stream functions.

Tau Proteins and Neuron Neurodegenerative Diseases

Tau proteins are neuronal microtubule-associated proteins known to promote the assembly of microtubules and to maintain microtubular integrity, which is physiologically essential for axonal transport and morphogenesis.[66, 67] These proteins are mainly expressed in neurons of the central nervous system (CNS), but are also found in astrocytes and oligodendrocytes at a much lower level.[68] Tau is found to be pathologically involved in several related disorders, termed tauopathies, in which aggregations of tau proteins are deposited in brain neurons.[69, 70] Such phenomenon is observed in a range of neurodegenerative diseases,[71-74] from fronto-temporal dementia (FTD), Parkinson's disease, Alzheimer's disease, to the less common progressive supranuclear palsy (PSP), as well as a progressive degenerative disease of the brain often found in athletes, military veterans, and others with a history of repetitive mild traumatic brain injury, called chronic traumatic encephalopathy (CTE).[75]

Figure 2:
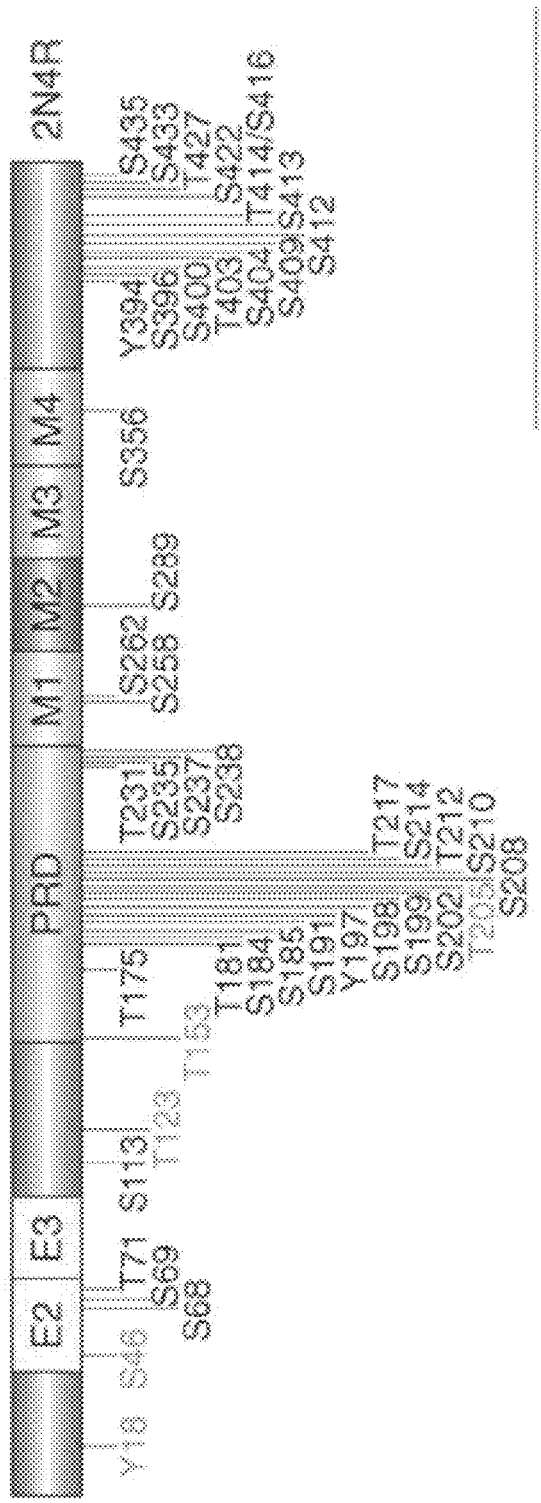
FIG. 2 illustrates positioning of phosphorylation sites on tau from Alzheimer brain, according to an embodiment of the disclosed invention.

Tau was first isolated and identified in 1975 as a heat stable protein essential for microtubule assembly by Dr. Kirschner's group.[66, 76] In the late 1980s, it was discovered that tau proteins found in adult human CNS is a mixture of six isoforms, ranging from 352 to 441 amino acids in length.[77-79] FIG. 1 is a reprinted with permission from Nature Publishing Group. It shows the human MAPT gene and the splice isoforms of tau in the human brain. MAPT, the gene encoding human tau, contains 16 exons. Exon 1 (E1), E4, E5, E7, E9, E11, E12 and E13 are constitutive, whereas the others are subject to alternative splicing. The six human brain tau isoforms are generated through alternative splicing of E2, E3 and E10.[84] The tau variants are expressed from alternative splicing in exons 2 (E2), 3 (E3), and 10 (E10) of a single MAPT (microtubule-associated protein tau) gene (as shown in FIG. 1 and FIG. 2).[80-84] Among the six isoforms, three of them have three binding domains (3R isoforms), while the other three with exon 10 inserts have four binding domains (4R isoforms). These conserved microtubule-binding domains are located in the C-terminal half of tau, and 3R isoforms bind less tightly to microtubules than 4R isoforms. Even though the molecular mechanism or the relative abundance of each tau isoform is yet ambiguous, the inability of commercially available ELISA kits to discriminate between the 6 isoforms demonstrate common epitope sites for each corresponding antibody across all 6 variants.[85]

Alzheimer's Disease

Alzheimer's disease, or Alzheimer disease (AD), is a neurological disorder that shows symptoms of memory loss and cognitive decline resulted from progressive degeneration or even loss of neurons in the brain. It is known as the most common form of dementia as well as the most prevalent case of tauopathies. Although the exact causes of Alzheimer's disease are not yet completely understood. Two major inclusions often sighted in its progression or postmortem are the extracellular plaques and the intracellular tangles.[86, 87] Plaques, or beta-amyloid plaques, are clumps of beta-amyloid monomers that get between the dying neurons and interfere with neuron-to-neuron signaling. Consequently, the brain functions, such as memory, could be seriously impaired because the neurons in brain cannot signal and relay information properly. Besides, amyloid plaques have also been found around blood vessels in the brain, causing amyloid angiopathy, which weakens the walls of blood vessels and increases the risk of hemorrhage.[88-90] The tangles, or neurofibrillary tangles (NFTs), on the other hand, are found within the brain neurons as abnormal clusters of tau proteins. Healthy neurons are held together by their cytoskeleton, which is partly built up with microtubules. Normal tau proteins bind with microtubules and prevent these track-like structures from breaking apart, allowing nutrients and molecules to be transported along the cells. Alzheimer tau, on the contrary, loses its affinity for microtubules due to an abnormally high degree of phosphorylation.[67] The pathological tau proteins self-assemble into the paired helical filaments (PHFs), which later aggregate into the insoluble neurofibrillary tangles.[91-93] The transport system for neurons is disrupted along the process, causing nutrients and other essential supplies to no longer move along the cells. Neurons with tangles and non-functioning microtubules thereby undergo apoptosis and eventually cell death.

Chronic Traumatic Encephalopathy

Chronic traumatic encephalopathy (CTE) is a progressive degenerative disease associated with repetitive traumatic brain injury (TBI). It has been most commonly found in professional athletes participating in contact sports and military personnel who have been exposed to a blast. There is often a long period of latency, ranging from several years to several decades, between the incident of TBI and the occurrence of the clinical symptoms of CTE. The initial symptoms of CTE include irritability, impulsivity, aggression, depression, short-term memory loss and heightened suicidality, but it may progress into cognitive deficits and dementia. The pathology of CTE is characterized by tauopathy, which shows the accumulation of phosphorylated tau protein in neurons and astrocytes.[94]

Hyperphosphorylation of Tau

The distinctive intracellular inclusions like neurofibrillary tangles observed in brains affected by Alzheimer's disease or chronic traumatic encephalopathy, or various forms of insoluble abnormal tau aggregates in other tauopathies, share a common composition of pathological tau, which is in an elevated state of phosphorylation, called hyperphosphorylation. Tau may be phosphorylated at many sites and by several kinases. A list of tau phosphorylation sites identified is shown in FIG. 2, which is a reprinted with permission from Elsevier.[95] As shown in FIG. 2, positioning of phosphorylation sites on tau from Alzheimer brain. Approximately 45 sites have been identified, and they seem to cluster in the PRD and in the C-terminal region, with few sites evident within the microtubule-binding domain of tau. Six of the phosphorylation sites have been identified only by phospho-specific antibody labelling (indicated in orange); the remaining phosphorylation sites have been identified by direct means (mass spectrometry and/or Edman degradation).[95] Many of the reported phosphorylations occur at Ser-Pro and Thr-Pro motifs, corresponding to phosphorylated sites sensitized by proline-directed kinases (MAPK, GSK-3, cdk5),[67, 96] but the hyperphosphorylation of tau is not confined within the proline-rich region. Apparently, increased phosphorylation in the microtubule-binding domain (residues 244-368) of tau would reduce the amount of tau binding to microtubules. One site that has been reported to have a great impact on the binding of tau to microtubules after its phosphorylation is Ser262.[97] However, it is also found that phosphorylation of tau at sites distinct from the microtubule-binding domain, such as at Thr231, could still have a pronounced influence on the binding affinity of tau to microtubules.[98] That being said, several other phosphorylation sites have only moderate effect on microtubule binding.

DNA Aptamers that are Capable of Recognizing Disease-Associated Targets

According to embodiments of the disclosed invention, by using specific peptide fragments from tau protein and pathologic phosphorylated tau proteins as targets to carry out the selection for site-specific tau protein-binding DNA aptamers (in short, "aptamers," "tau aptamers," or "DNA aptamers") that recognize tau at designated phosphorylatable sites are identified and selected. Molecular probes are further developed using the site-specific tau aptamers. Therefore, embodiments of the disclosed invention provide DNA aptamers that not only recognize tau at designated phosphorylatable sites, but also demonstrate the inhibitory effects on phosphorylation and oligomer formation of tau. These tau protein-binding DNA aptamers are feasible to apply to (1) detect the levels of tau and phosphotau in cerebrospinal fluid as capture or detection agent, (2) study the mechanism of tauopathy, and (3) arrest the progression of tauopathy associated neurodegenerative disorders.

In one embodiment of the disclosed invention, DNA aptamers that are capable of recognizing disease-associated targets are identified through two different approaches, the cell-based systematic evolution of ligands by exponential enrichment (SELEX) and peptide SELEX. Table 1 is a list of exemplary DNA aptamers disclosed in one embodiment of the present invention. These tau protein-binding DNA aptamers not only recognize tau at designated phosphorylatable sites, but also demonstrate inhibitory effects on phosphorylation and oligomer formation of tau.

TABLE 1

Full nucleotide sequence (5' --> 3') of Tau-binding DNA aptamers and truncated Tau-binding DNA aptamers, according to an embodiment of the disclosed invention.

| Aptamer Name | full nucleotide sequence (5' --> 3') of Tau-binding aptamers |
|---|---|
| IT1 | CAGCACCGTCAACTGAATTGCTTGGTCCTCCCGGGGT TCTGGAAAAGCGTGATGCGATGGAGATGT (SEQ ID NO: 1) |
| IT2 | CAGCACCGTCAACTGAATAAGGACTGCTTAGGATTGC GATGATTCAGGGTGATGCGATGGAGATGT (SEQ ID NO: 2) |
| IT3 | CAGCACCGTCAACTGAATGGGGAGAGTGGTGGGGCGG GGGCCGGATCCGTGATGCGATGGAGATGT (SEQ ID NO: 3) |
| IT4 | CAGCACCGTCAACTGAATGGGTTGGCCGGGCAGCGGG GGGTAGGCTTGGTGATGCGATGGAGATGT (SEQ ID NO: 4) |
| IT5 | CAGCACCGTCAACTGAATGGCGGGGGGTCAGGTCGGG GTAAGGTGAGCGTGATGCGATGGAGATGT (SEQ ID NO: 5) |
| IT6 | CAGCACCGTCAACTGAATGTTGTCGTCAGAGGTTATA ACCTGAACTCGGTGATGCGATGGAGATGT (SEQ ID NO: 6) |
| IT9 | CAGCACCGTCAACTGAATTGCGGGGGGTCAGGTCGGG GTAAGGTGAGCGTGATGCGATGGAGATGT (SEQ ID NO: 7) |
| T231-IT1a | CCGTCAACTGAATTGCTTGGTCCTCCCGGGGTTCTGG AAAAGCGTGATGCGATGG (SEQ ID NO: 8) |

TABLE 1-continued

Full nucleotide sequence (5' --> 3') of Tau-binding DNA aptamers and truncated Tau-binding DNA aptamers, according to an embodiment of the disclosed invention.

| Aptamer Name | full nucleotide sequence (5' --> 3') of Tau-binding aptamers |
|---|---|
| T231-IT1b | CCGTCAACTGAATTGCTTGGTCCTCCCGGGGTTCTGGAAAAGC (SEQ ID NO: 9) |
| T231-IT1c | GCTTGGTCCTCCCGGGGTTCTGGAAAAGC (SEQ ID NO: 10) |
| T231-IT1d | TTGGTCCTCCCGGGGTTCTGGAAAA (SEQ ID NO: 11) |
| T231-IT2a | CTGAATAAGGACTGCTTAGGATTGCGATGATTCAG (SEQ ID NO: 12) |
| T231-IT2b | AAGGACTGCTTAGGATTGC (SEQ ID NO: 13) |
| T231-IT2c | TGAATAAGGACTGCTTAGGATTGCGATGATTCA (SEQ ID NO: 14) |
| T231-IT2d | GAATAAGGACTGCTTAGGATTGCGATGATTC (SEQ ID NO: 15) |
| T231-IT2e | AATAAGGACTGCTTAGGATTGCGATGATT (SEQ ID NO: 16) |
| T231-IT3a | CAGCACCGTCAACTGAATGGGGAGAGTGGTGGGGCGG (SEQ ID NO: 17) |
| T231-IT3b | CAGCACCGTCAACTGAATGGGGAGAGTGGTGGGGCGGGGGCCGGATCCGTGATGCG (SEQ ID NO: 18) |
| T231-IT3c | CAGCACCGTCAACTGAATGGGGAGAGTGGTGGGGCGGGGGCCGGATCCGTGATGCGATGGA (SEQ ID NO: 19) |
| T231-IT4a | CACCGTCAACTGAATGGGTTGGCCGGGCAGCGGGGGTAGGCTTGGTG (SEQ ID NO: 20) |
| T231-IT4b | CACCGTCAACTGAATGGGTTGGCCGGGCAGCGGGGGTAGGCTTGGTGATGCGATG (SEQ ID NO: 21) |
| T231-IT4c | CAGCACCGTCAACTGAATGGGTTGGCCGGGCAGCGGGGGGTAGGCTTGGTGATGCGATG (SEQ ID NO: 22) |
| T231-IT5a | CCGTCAACTGAATGGCGGGGGGTCAGGTCGG (SEQ ID NO: 23) |
| T231-IT5b | CACCGTCAACTGAATGGCGGGGGGTCAGGTCGGGGTAAGGTG (SEQ ID NO: 24) |
| T231-IT5c | CACCGTCAACTGAATGGCGGGGGGTCAGGTCGGGGTAAGGTGAGCGTGATGCG (SEQ ID NO: 25) |
| T231-IT6a | CACCGTCAACTGAATGTTGTCGTCAGAGGTTATAACCTGAACTCGGTG (SEQ ID NO: 26) |
| T231-IT6b | CGTCAACTGAATGTTGTCGTCAGAGGTTATAACCTGAAC (SEQ ID NO: 27) |

In particular, using phosphorylated and non-phoshorylated tau epitope sequences around site of human tau Ser-202, Thr205, Thr-231, Thr-181, Ser-398-Ser-404, seven tau aptamers that are high affinity tau epitope-binders, termed IT1 (SEQ ID NO: 1), IT2 (SEQ ID NO: 2), IT3 (SEQ ID NO: 3), IT4 (SEQ ID NO: 4), IT5 (SEQ ID NO: 5), IT6 (SEQ ID NO: 6), and IT9 (SEQ ID NO: 7), respectively, have been identified (See Table 1). Each of IT1 (SEQ ID NO: 1), IT2 (SEQ ID NO: 2), IT3 (SEQ ID NO: 3), IT4 (SEQ ID NO: 4), IT5 (SEQ ID NO: 5), IT6 (SEQ ID NO: 6), and IT9 (SEQ ID NO: 7) is 66 nucleotide long. In an embodiment, four phosphorylatable regions from tau protein and the corresponded phosphorylated peptide fragments from pathologic tau are used as targets to carry out the selection for site-specific tau aptamers. DNA aptamer IT3 (SEQ ID NO: 3) overlooks phosphorylation on T231 and recognizes both T231 and T231P. DNA aptamer IT2 (SEQ ID NO: 2) may bind to T231, T231P, and S202, but not S202P. The other aptamers discovered are highly specific to T231 site only.

Accordingly, embodiments provide a DNA aptamer comprising a nucleic acid sequence that is capable of specifically binding to a tau protein at a phosphorylatable site of the tau protein. The nucleic acid sequence comprises 66 nucleotides and is selected from the group consisting of SEQ ID NO: 2, SEQ ID NO: 3, SEQ ID NO: 4, SEQ ID NO: 5, SEQ ID NO: 6, and SEQ ID NO: 7.

In addition, it is found that 5'-end and 3'-end truncated nucleic acid fragments of a 66 nucleotide long tau aptamer of IT1 (SEQ ID NO: 1), IT2 (SEQ ID NO: 2), IT3 (SEQ ID NO: 3), IT4 (SEQ ID NO: 4), IT5 (SEQ ID NO: 5), IT6 (SEQ ID NO: 6), and IT9 (SEQ ID NO: 7) also yield smaller aptamers that show high affinity to tau protein. All of the tau aptamers disclosed here showed high affinity to tau protein.

For example, each of T231-IT1a (SEQ ID NO: 8), T231-IT1b (SEQ ID NO: 9), T231-IT1C (SEQ ID NO: 10), and T231-IT1d (SEQ ID NO: 11), as listed in Table 1, is a smaller aptamer that is a truncated fragment of the nucleic acid sequence of IT1 (SEQ ID NO: 1). Each of T231-IT2a (SEQ ID NO: 12), T231-IT2b (SEQ ID NO: 13), T231-IT2C (SEQ ID NO: 14), T231-IT2d (SEQ ID NO: 15), and T231-IT2e (SEQ ID NO: 16), as listed in Table 1, is a smaller aptamer that is a truncated fragment of the nucleic acid sequence of IT2 (SEQ ID NO: 2). Each of T231-IT3a (SEQ ID NO: 17), T231-IT3b (SEQ ID NO: 18), and T231-IT3C (SEQ ID NO: 19), as listed in Table 1, is a smaller aptamer that has a truncated nucleic acid sequence based on the nucleic acid sequence of IT3 (SEQ ID NO: 3). Each of T231-IT4a (SEQ ID NO: 20), T231-IT4b (SEQ ID NO: 21), and T231-IT4C (SEQ ID NO: 22), as listed in Table 1, is a smaller aptamer that has a truncated nucleic acid sequence based on the nucleic acid sequence of IT4 (SEQ ID NO: 4). Each of T231-IT5a (SEQ ID NO: 23), T231-IT5b (SEQ ID NO: 24), and T231-IT5C (SEQ ID NO: 25), as listed in Table 1, is a smaller aptamer that has a truncated nucleic acid sequence based on the nucleic acid sequence of IT5 (SEQ ID NO: 5). Each of T231-IT6a (SEQ ID NO: 26) and T231-IT6b (SEQ ID NO: 27), as listed in Table 1, is a smaller aptamer that has a truncated nucleic acid sequence based on the nucleic acid sequence of IT6 (SEQ ID NO: 6). These 5'-end and 3'-end truncated nucleic acid sequences are 25 to 61 nucleotides long) (See Table 1).

All these tau protein-binding DNA aptamers disclosed herein, as shown in Table 1, are unique nucleotide A, T, G, C-based sequences. Each of these smaller is capable of specifically binding to a tau protein at a phosphorylatable site of the tau protein.

Utilities of Disclosed Tau Protein-Binding DNA Aptamers

The discloses tau aptamers may be used to (1) detect the levels of tau in cerebrospinal fluid, blood or other biofluids, (2) to study the mechanism of tauopathy, and (3) arrest the progression of tauopathy associated disorders by binding and sequestering tau and/or P-tau from the brain by administrating tau aptamers into the human body.

Molecular probes based on these disclosed DNA aptamers may be used as capture or detection agents to detect the levels of tau and phosphor-tau in cerebrospinal fluid as well as for cell-based or in vivo brain imaging in live animals or human. Compositions comprising these disclosed DNA aptamers may further be used to arrest or treat the progression of tauopathy associated neurodegenerative disorders.

Detection of Tau in Cerebrospinal Fluid (CSF), Blood and Other Biofluids

FIGS. 27A and 27B illustrate aptamer-based molecular beacons labeled with quencher Q and fluorophore F for detection of tau protein, according to an embodiment of the disclosed invention. FIG. 27A shows that fluorescence is recovered due to the conformational change of aptamer upon binding to the target tau protein. F for detection of tau protein, according to an embodiment of the disclosed invention. FIG. 27B shows a fluorophore-labeled DNA strand (blue) complimentary to one end of the DNA aptamer (red) is released upon aptamer-target complex formation. The fluorescence intensity is hence restored. Accordingly, in one embodiment, a DNA aptamer conjugate comprising a DNA aptamer that is conjugated with quencher Q and fluorophore F is provided. The quencher Q and fluorophore are signal moieties bound on the DNA aptamer.

With tau aptamers, the presence of tau or even the level of tau may be directly detected through a fluorescence recovery mechanism. It has been demonstrated that aptamers may undergo conformational changes upon target binding.[158, 159] Labeling a fluorophore at one end of a hairpin-structure tau aptamer IT1c or IT2a and a nonfluorescent quencher at the opposite end would create a molecular beacon that is responsive to the presence of its binding target tau protein as shown in FIG. 27A. The binding of tau to the aptamer could cause the separation between the fluorophore and quencher due to the conformational change of the molecular beacon and hence result in the enhancement in fluorescence intensity with little background.

However, this approach relies on the nature of the specific aptamer. It may not be applicable if the specific aptamer used does not undergo major conformational changes upon target binding. In this case, another strategy as shown in FIG. 27A will be applied. The quencher is labeled on a DNA strand that is complementary to one end of the hairpin stem and part of the hairpin loop. The short complementary DNA will be released from the aptamer upon binding to the target and therefore restore the fluorescence intensity.

Figure 28:
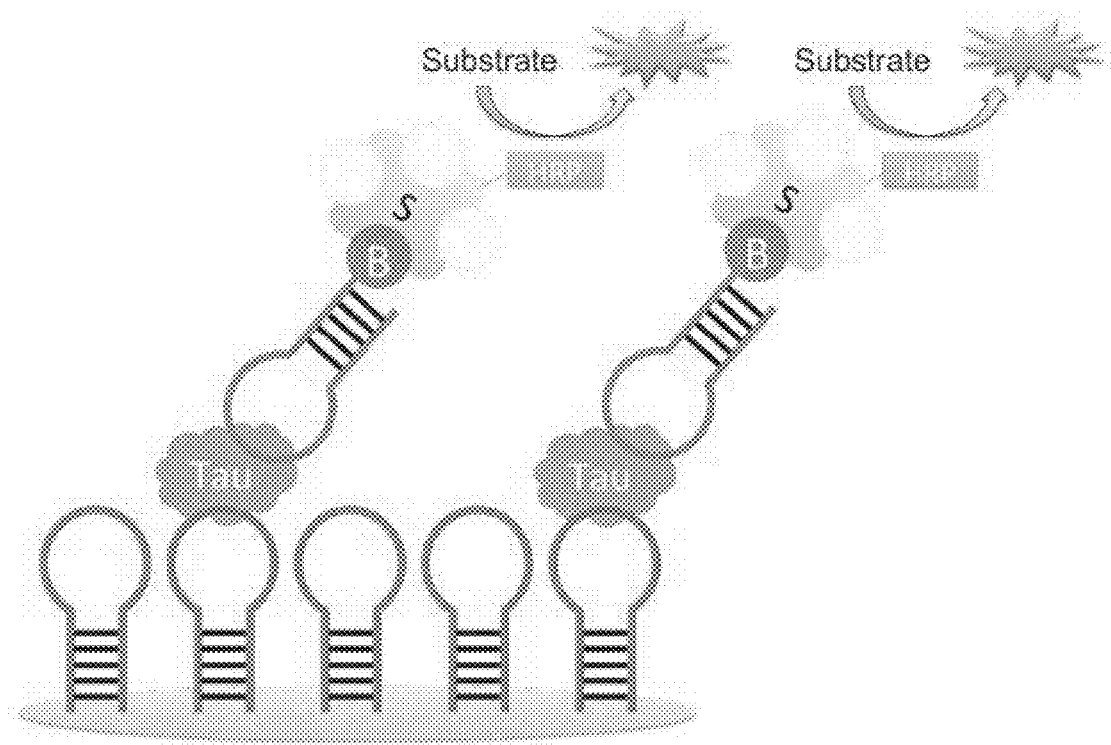
FIG. 28 illustrates sandwich assay for detection of tau protein, according to an embodiment of the disclosed invention.

Beside the rapid fluorescence recovery assay that readily detects the presence of tau in a semi-quantitative manner, tau aptamers may also be used to perform a more quantitative sandwich assay to determine the concentration of tau in CSF with a larger linear dynamic range. FIG. 28 illustrates sandwich assay for detection of tau protein, according to an embodiment of the disclosed invention. One aptamer is used as a capture probe while the other aptamer carries biotin for interacting with streptavidin and HRP for signaling. As depicted in FIG. 28, two tau aptamers targeting different binding regions on tau are used for the sandwich assay. One of the aptamers (capture probe) is coated on the surface of a microplate to capture tau protein in CSF, and then another tau aptamer modified with biotin will be added followed by washing and incubation with streptavidin conjugated with horseradish peroxidase enzyme (HRP). After washing away the unwanted residues, the assay will be developed with a HRP substrate to form colorimetric products for analysis. This assay not only increases the diagnostic accuracy by incorporating two aptamers but also improves the detection limit by the enzyme-substrate reaction.

Different from technologies that detect total tau and phosphorylated tau by mass spectrometry, positron emission tomography (PET) imaging, and western blotting in combination with immunoprecipitation or high performance liquid chromatography (HPLC), the disclosed invention provides an approach to directly detect the levels of total tau and phosphorylated tau. Unlike antibodies, tau aptamer may be produced in high quantity and high fidelity. Tau aptamers are also smaller than antibodies. Aptamers may be readily be chemically modified to improve binding property, cell-permeability, plasma half-life and immunogenicity and for detection (biotin, HRP, avidin or fluorophore conjugation)—thus it is superior to antibodies.

In particular, the disclosed invention provides a composition comprising a DNA aptamer that is capable of binding to a tau protein at a phosphorylatable site of the tau protein. In one embodiment, a composition comprising a DNA aptamer that is capable of specifically binding to a tau protein at a phosphorylatable site of the tau protein. The nucleic acid sequence of the DNA aptamer is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and SEQ ID NO: 27. This DNA aptamer may be used as a molecular probe for binding and detecting phosphorylatable sites on a tau protein. In some alternative embodiment, the phosphorylatable sites on a tau protein may be Thr-231 and/or Ser-202. In some alternative embodiment, the phosphorylatable sites on a tau protein may be Thr-231, Ser-202, Thr-231, and/or Ser-398-Ser404.

Embodiments further provide a kit for testing the presence or progression of various tauopathy diseases. In one embodiment, the kit comprises a DNA aptamer disclosed herein and a tau-binding antibody. The tau-binding antibody may be a mouse monoclonal or rabbit of goat polyclonal antibody. In one embodiment, the kit comprises two or more DNA aptamer disclosed herein and a tau-binding antibody, such as a mouse monoclonal or rabbit of goat polyclonal antibody. In an alternative embodiment, the nucleic acid sequence of the DNA aptamer is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and SEQ ID NO: 27. In an alternative embodiment, the kit comprises two or more DNA aptamers.

Embodiments further provide a method for testing the presence or the progression of a various tauopathy disease by using the kit disclosed herein.

Embodiments disclosed further herein provide a method of using Tau-binding aptamer disclosed herein as a capture and/or detection tool for detecting phosphorylated Tau, non-phosphorylated Tau, or total Tau in a biosample, such as blood, CSF and other biofluid or brain tissue lysate. A tau aptamer may be used as a single capture-detection tool or in combination as a sandwich, which is "capture tool-Tau target-detection tool," by combining with another aptamer or with a tau-binding antibody. The tau-binding antibody may be a mouse monoclonal or rabbit of goat polyclonal antibody. The assays may be used as a tau/P-tau based biomarker diagnostic test for the presence or progression of various tauopathy diseases. In one embodiment, the method includes measuring the binding of a DNA aptamer to a phosphorylated tau protein, a non-phosphorylated tau, or a total tau protein in a biosample obtained from a subject, thereby determining the level of tau and phosphor-tau in the biosample from the subject. The level of tau and phosphor-tau tested in the biosample from a subject may be compared with a level of tau and phosphor-tau of a healthy subject who does not have a tauopathy disease, thereby determining if a tauopathy disease is present or not. The method further comprising measuring the binding of a DNA aptamer using the kit disclosed herein. The subject may be an animal or human. In an alternative embodiment, the subject has Alzheimer's disease and/or chronic traumatic encephalopathy, wherein a healthy subject does not have Alzheimer's disease and/or chronic traumatic encephalopathy. In some alternative embodiments, the phosphorylatable sites tested on a tau protein may be Thr-231 and/or Ser-202. In some alternative embodiment, the phosphorylatable sites tested on a tau protein may be Thr-231, Ser-202, Thr-231, and/or Ser-398-Ser404. In an alternative embodiment, the sample is a biosample, such as blood, CSF and other biofluid or brain tissue lysate, obtained from the subject.

Imaging of Tau in Living Cells Using Tau-Binding DNA Aptamers

Aptamer-based molecular beacons are not just probes for target analysis. They may also be used as imaging agents in living cells. However, since tau is located in cytoplasm rather than on cell surface, the delivery of tau molecular beacons into cells is an essential challenge for imaging of tau. As chemically synthesized oligonucleotide-based probes, aptamers may be readily modified with a variety of functional groups and signaling moieties.

Embodiments provide a DNA aptamer conjugate comprising a disclosed tau-binding DNA aptamer conjugated to a reporter moiety. The reporter moiety may be a molecular becon, fluorescent tag, a radioisotope for positron emission tomography (PET), single-photon emission computed tomography (SPECT), contrast-agent-based MRI, etc. The conjugated DNA aptamer may be used for detection of tau protein.

Figure 29:
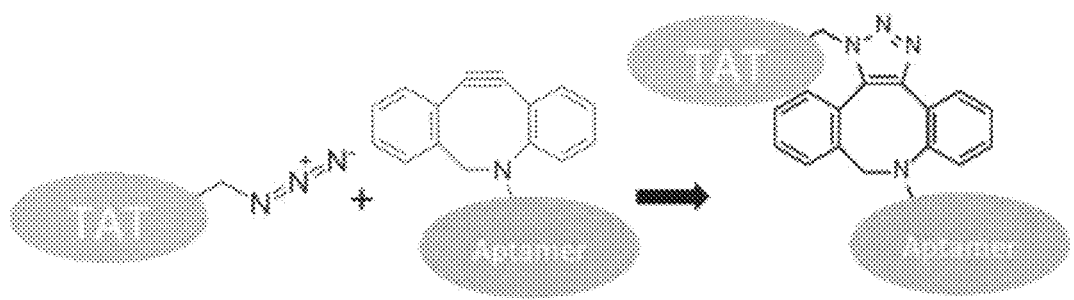
FIG. 29 illustrates DBCO modified DNA aptamer can be linked with azido-TAT peptide via click chemistry for intracellular imaging of tau, according to an embodiment of the disclosed invention.

FIG. 29 illustrates DBCO modified DNA aptamer may be linked with azido-TAT peptide via click chemistry for intracellular imaging of tau, according to an embodiment of the disclosed invention. Embodiments provide a DNA aptamer conjugate, which is a conjugated Tau-binding aptamer. The DNA aptamer conjugate comprises a DNA aptamer disclosed herein, which is capable of binding to a tau protein at a phosphorylatable site of the tau protein, and a moiety linked to the DNA aptamer. The moiety may be an azido-containing cell penetrating peptide (CPP), such as azido-TAT. In one embodiment, the DNA aptamer conjugate is a TAT-conjugated aptamer. By modifying a DNA aptamer disclosed herein with a dibenzylcyclooctyne (DBCO) group, the DNA aptamer may be linked with an azido-containing cell penetrating peptide (CPP), such as azido-TAT (a cell penetrating peptide derived from the trans-activator of transcription of HIV), via click chemistry (FIG. 29). The DNA aptamer conjugate comprises a modified DNA aptamer that is linked with an azido-containing cell penetrating peptide. The modified DNA aptamer is capable of binding to a tau protein at a phosphorylatable site of the tau protein. The DNA aptamer comprises a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and SEQ ID NO: 27.

In combination with a fluorophore and a quencher (fluorescence recovery molecular beacon), this TAT-conjugated aptamer may be used to image intracellular tau protein in situ. Thus, a tau aptamer disclosed herein may also be used for neuroimaging purposes, such as with PET, SPECT and contrast-agent-based MRI, for detecting brain injury or development of tauopathy. The disclosed tau aptamer further have novel utilities in traumatic brain injury (TBI), chronic traumatic encephalopathy, Alzheimer's disease, and other tauopathy-linked neurodegenerative diseases (e.g. Parkinsonism).

In one embodiment, a TAT-conjugated aptamer is introduced into a cell for imaging intracellular phosphorylated tau, non-phosphorylated tau, and/or total tau in situ. Accordingly, embodiments further provide a method for cell-based imaging of phosphorylated tau, non-phosphorylated tau, and/or total tau in a cell. The method comprises introducing a DNA aptamer conjugate into cells in a cell culture medium in vitro by adding a composition comprising the DNA aptamer conjugate into the cell culture medium and detecting the binding of the DNA aptamer conjugate to a tau protein in the cell. The DNA aptamer conjugate comprises a modified DNA aptamer that is linked with an azido-containing cell penetrating peptide. The modified DNA aptamer is capable of binding to a tau protein at a phosphorylatable site of the tau protein. The DNA aptamer comprises a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and SEQ ID NO: 27.

Alternatively, a composition comprising the disclosed DNA aptamer conjugate may be delivered or administered into a subject in need thereof for imaging the phosphorylated Tau, non-phosphorylated Tau or total Tau in the brain of the subject. The subject may be a live animal or a human. The composition comprising the disclosed DNA aptamer conjugate may be administered systemically or regionally into the subject. In one embodiment, a DNA aptamer conjugate is administered into a subject by injection. For example, the DNA aptamer conjugate may be regionally injected into the brain region or ventricle of the brain for in vivo imaging in a subject. The subject may be animals or human.

Treating a Progression of Tauopathy Associated Neurodegenerative Disorder

Furthermore, a tau aptamer disclosed herein, when bound to Tau protein may inhibit in vitro Tau phosphorylation by protein kinases. A tau aptamer disclosed herein, when bound to tau protein, may also inhibit tau protein aggregation in vitro (as induced by heparin). Modified forms of some of tau aptamers may further bind tau protein and microtubule in a cell culture system, for example, rat cortical neurons, neuroblastoma cells N2A, etc.

A tau aptamer disclosed herein may be used for treating a progression of tauopathy associated neurodegenerative disorder. In one embodiment, a composition comprising a DNA aptamer disclosed herein is a pharmaceutical composition comprising a DNA aptamer disclosed herein and a pharmaceutically acceptable carrier such as a diluent or excipient. The pharmaceutical composition is formulated in a dosage form. Alternatively, the composition comprises a DNA aptamer disclosed herein and a pharmaceutically acceptable salt. The DNA aptamer is capable of binding to a tau protein at a phosphorylatable site of the tau protein.

In one embodiment, the composition comprising a DNA aptamer comprising a nucleic acid sequence set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, or SEQ ID NO: 27. The composition disclosed herein may be administered to a subject in need thereof. In one alternative embodiment, the pharmaceutical composition disclosed herein may be delivered to a subject via injection. When the DNA aptamer is delivered into the body of the subject, the DNA aptamer is capable of binding at a phosphorylatable site of the tau protein and inhibit tau phosphorylation at the phosphorylatable site and inhibit tau protein oligomerization and/or aggregation in the subject's brain. Accordingly, administering to a subject in need thereof a pharmaceutical composition comprising a therapeutically effective amount of a DNA aptamer that is capable of binding to a tau protein at a phosphorylatable site of the tau protein may arrest or treat the progression of a tauopathy associated disorder. In an embodiment, the subject being treated with the disclosed DNA aptamer has Alzheimer's disease and/or chronic traumatic encephalopathy.

Alternatively, embodiments provide a method for arrest the progression of tauopathy associated disorder s by administrating a pharmaceutical composition comprising a tau-binding DNA aptamer disclosed herein into the body of a subject. The pharmaceutical composition comprising the Tau-binding DNA aptamer may be administered into the circulating blood of the subject. The tau-binding DNA aptamer may arrest the progression of tauopathy associated disorders by binding and sequestering Tau and/or P-Tau from the brain as an organ gradually.

Alternatively, embodiments provide a method to introduce one or more Tau-binding DNA aptamers into brain of a subject and/or brain cells. When the Tau-binding DNA aptamers are bound to Tau protein, they may inhibit Tau phosphorylation by endogenous protein kinases in the brain of a subject and/or the brain cells.

In one embodiment, one or more Tau-binding aptamers are introduced into a brain of a subject and/or brain cells. When aptamers are bound to Tau protein, they may inhibit tau protein aggregation in the brain cells or in the brain interstitial fluid.

Figure 32:
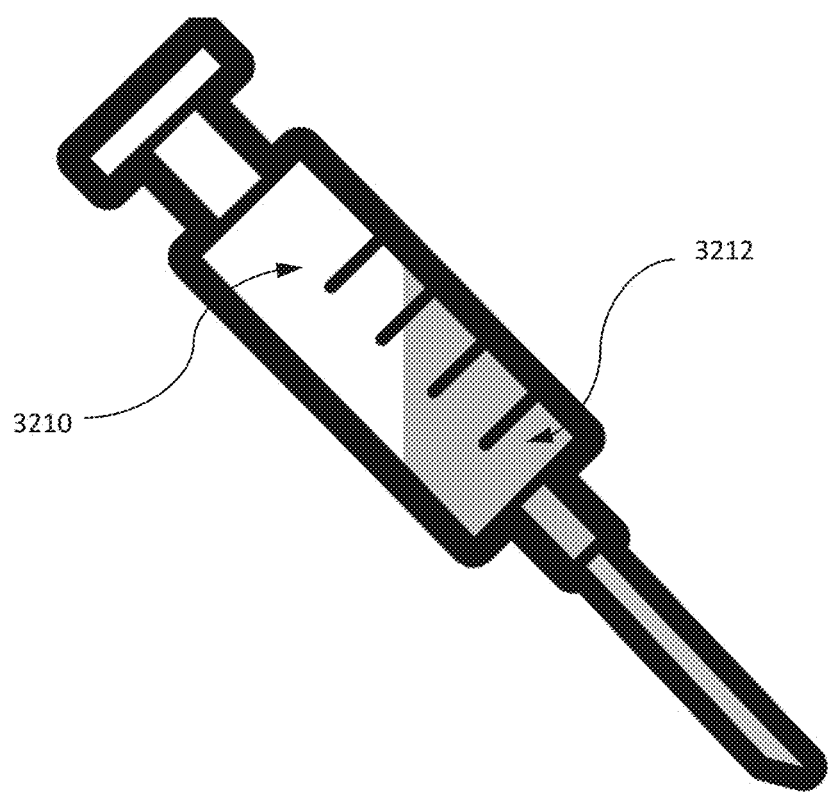
FIG. 32 illustrates a delivery apparatus containing an injection liquid solution or suspension comprising at least one effective dosage of a pharmaceutical composition comprising a therapeutically effective amount of a DNA aptamer that is capable of binding to a tau protein at a phosphorylatable site of the tau protein, an adjuvant, and/or a pharmaceutically acceptable diluent or excipient, according to an embodiment of the disclosed invention.

In one embodiment, a delivery apparatus used for treating a tauopathy associated disorder is further provided. The delivery apparatus contains a pharmaceutical composition comprising a therapeutically effective amount of a disclosed DNA aptamer that is capable of binding to a tau protein at a phosphorylatable site of the tau protein. This delivery apparatus may be an injectable drug delivery device containing an injection liquid solution or suspension contained in the injectable drug delivery device, wherein the injection liquid solution or suspension comprises at least one effective dosage of a pharmaceutical composition comprising a therapeutically effective amount of a DNA aptamer that is capable of binding to a tau protein at a phosphorylatable site of the tau protein, an adjuvant, and/or a pharmaceutically acceptable diluent or excipient. FIG. 32 illustrates a delivery apparatus for delivering a pharmaceutical composition disclosed herein. The delivery apparatus comprises an injectable drug delivery device 3210 and a liquid solution or suspension 3212 comprising the pharmaceutical composition disclosed herein.

All documents, patents, journal articles and other materials cited in the present application are incorporated herein by reference.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

The disclosed invention is further defined in the following Examples. It should be understood that these Examples are given by way of illustration only. From the above discussion and these Examples, one skilled in the art may ascertain the essential characteristics of embodiments of the disclosed invention. Without departing from the spirit and scope thereof, one skilled in the art may make various changes and modifications of the invention to adapt it to various usages and conditions. All publications, including patents and non-patent literature, referred to in this specification are expressly incorporated by reference herein.

EXAMPLES

In the following examples, specific peptide fragments from tau protein and pathologic phosphorylated tau proteins were used as targets to carry out the selection for site-specific tau aptamers. The identification of a panel of phosphorylatable sites/epitopes specific tau aptamers using peptide SELEX was described. A panel of phosphorylatable sites specific tau aptamers was selected using specific peptide fragments from tau protein and pathologic phosphorylated tau proteins as putative targets.

One of the aptamers identified (IT3) overlooked phosphorylation on T231 and recognized both T231 and T231P. Another one (IT2) could bind to T231, T231P, and S202, but not S202P. The rest of the aptamers discovered were highly specific to T231 site only. Three of the identified aptamers were truncated into shorter versions without appreciable compromise on their binding abilities to targets. All of the tau aptamers reported here showed high affinity to tau protein. The dissociation constants of these aptamers against Tau441 protein ranged between 5.5 nM to 68 nM.

Finally, the specificity and the inhibitory effects of the selected tau aptamers were demonstrated. All of the tested tau aptamers were highly specific to tau protein. No cross-reaction was observed with any of the non-target proteins. Besides, in vitro inhibition on oligomerization by several Tau-binding aptamers (new Figure Y), as well as in vitro protection against protein kinase (e.g. GSK3beta)-mediated Tau phosphorylation (new figures X) was confirmed. Moreover, the cell-based experiment showed that aptamers IT1c and IT2a are capable of interfering with the phosphorylation of tau and thus minimizing the formation of phosphor-tau oligomers inside living cells.

Example 1

Identification of DNA Aptamers Targeting Susceptible Phosphorylation Sites on Tau Significance and Background Healthy neurons are held together by their cytoskeleton, which is partly built up with microtubules. Tau proteins are neuronal microtubule-associated proteins known to promote the assembly of microtubules and to maintain microtubular integrity. Normal tau proteins bind with microtubules and prevent these track-like structures from breaking apart, allowing nutrients and molecules to be transported along the cells. However, it has been proved that tau is pathologically involved in several neuron related disorders. The deposition of aggregated tau in brain neurons are observed in a range of neurodegenerative diseases, from fronto-temporal dementia (FTD), progressive supranuclear palsy (PSP), chronic traumatic encephalopathy (CTE), to Parkinson's disease and Alzheimer's disease.71-75 The aggregated form of tau loses its affinity for microtubules due to an abnormally high degree of phosphorylation.67 The abnormal clusters of tau proteins found within the brain neurons are known as neurofibrillary tangles (NFTs). These tangles are insoluble and are disruptive to the transport system in neurons, causing nutrients and other essential supplies to no longer move along the cells. Neurons with tangles and non-functioning microtubules thereby undergo apoptosis and eventually cell death.

The most fundamental difference between healthy tau protein and the pathological tau protein is the phosphorylation level. Tau may be phosphorylated at many sites, but these sites are very specific. Aptamers are nucleic acid probes capable of binding to particular ligands. They are selected from combinatorial oligonucleotide libraries through an evolution process called SELEX. Aptamers have shown remarkable specificity in discriminating targets from their similar analogs, such as differentiating among homologous proteins that differed only by a few amino acids28 or one single amino acid,29 or even between enantiomers.30, 31 Here, to exploit the specificity of aptamers, fragments of phosphorylatable regions from tau protein and their corresponding phosphorylated forms were used as putative targets to search for site-specific tau aptamers that may further be used to regulate up-stream or down-stream functions associated with phosphorylation of tau protein.

Materials and Methods

Buffers and Peptides

The buffer used to disperse peptides and peptide-beads was Dulbecco's phosphate buffered saline (PBS) with calcium chloride and magnesium chloride (Sigma-Aldrich). The buffer used to prepare DNA solutions as well as the buffer for all binding reactions was Dulbecco's phosphate buffered saline (PBS) with calcium chloride and magnesium chloride (Sigma-Aldrich) with additional 5 mM MgCl2. The sequences of the peptides used in this study were TPPAPKTPPSSGE (T181) (SEQ ID NO: 28), TPPAPKT(p)PPSSGE (T181P) (SEQ ID NO: 28), GYSSPGSPGTPGSR (S202) (SEQ ID NO: 29), GYSSPGS(p)PGTPGSR (S202P) (SEQ ID NO: 29), KVAVVRTPPKSPS (T231) (SEQ ID NO: 30), KVAVVRT(p)PPKSPS (T231P) (SEQ ID NO: 30), EIVYKSPVVSGDTSPRH (S396S404) (SEQ ID NO: 31), EIVYKS(p)PVVSGDTS(p)PRH (S396S404P) (SEQ ID NO: 31). All peptides were purchased from GenScript; they all came with N-terminal acetylation and 2 units of 6-aminocaproic acid (Ahx) linker followed by 6 histidine residues (his-tag) (SEQ ID NO: 32) at their C-terminus.

Immobilization of Tau/P-Tau Peptides

20 µL of stock Ni sepharose high performance beads (~7×105 Ni-NTA beads, GE Healthcare Life Sciences) were washed/equilibrated with 500 µL of PBS three times. After quick spin-down with mini centrifuge (Fisher Scientific), supernatant was discarded. The remaining pellet was suspended in 100 µL of PBS containing either 400 µg/mL or 800 µg/mL of the designated peptide and left overnight at 4° C. on a shaker. The prepared peptide-beads were kept in the peptide solution and left unwashed at 4° C. until before use. Beads used in counter selections or negative controls in binding tests were prepared as mentioned above but suspended in PBS as opposed to peptide solution.

DNA Library and Primers

The forward primer and the reverse primer were labeled with FAM and biotin, respectively, at their 5'-ends. The sequence of the forward primer was 5'-FAM-CAG CAC CGT CAA CTG AAT-3' (SEQ ID NO: 33); the sequence of the reverse primer was 5'-Biotin-ACA TCT CCA TCG CAT CAC-3' (SEQ ID NO: 34). The DNA library consisted of a randomized 30-nt region flanked by primer binding sites: 5'-CAG CAC CGT CAA CTG AAT-(N30)-GTG ATG CGA TGG AGA TGT-3' (SEQ ID NO: 35). All library and primer sequences were purchased from Integrated DNA Technologies (IDT) and purified by reverse phase HPLC.

Polymerase Chain Reaction (PCR)

PCR parameters were optimized before the selection process. All PCR mixtures contained 50 mM KCl, 10 mM Tris-HCl (pH 8.3), 1.5 mM MgCl2, 0.2 mM each dNTP, 0.5 µM each primer, and hot start Taq DNA polymerase (0.015 units/µL). PCR was performed on a BioRad C1000 Thermo Cycler, and all PCR reagents were purchased from Takara. The amplification began with a hot start at 95° C. for 90 sec to activate Taq DNA polymerase. Then each of the repeated amplification cycle was performed at 95° C. for 30 sec, 57° C. for 30 sec, and 72° C. for 60 sec, followed by a one-time final extension at 72° C. for 3 min.

SELEX Procedures

The SELEX process was performed by binding the DNA library to the peptide-immobilized beads and eluting DNA survivors from the washed peptide-beads followed by PCR amplification in a reciprocal manner. In the first round, an initial DNA library consisted of 20 nmol of the randomized oligonucleotides in 500 µL of buffer was used as a starting pool. For later rounds, 150 pmol (Rounds #2-#3), 125 pmol (Rounds #4-#7), 75 pmol (Rounds #8-#15), or 20 pmol (Rounds #16-#17) of oligonucleotides amplified from previous recovered binding survivors were used. In each round, the DNA pool was heated at 95° C. for three minutes, followed by rapid cooling on ice for 5 minutes before starting incubation, allowing the DNA sequences to form the most favorable secondary structures. Beads were washed against 1 mL of PBS three times before use. Counter selection with bare Ni-NTA beads was introduced in Round #6 and was thereafter included in all subsequent rounds. Sandwiched counter selections were used in Round #8 as well as in all later rounds. All positive incubations and negative incubations were done at 4° C. After each cycle of negative incubation, supernatant was collected while the undesired sequences bound on Ni-NTA beads were discarded. As for positive incubations, peptide-beads were washed with buffer to remove unbound sequences. The washing stringency was enhanced as the selection progressed to remove weak candidates. The washed peptide-beads were heated at 95° C. for 7 minutes followed by quick spin-down with mini centrifuge. The survived candidates in the supernatant were collected and were ready for PCR amplification during the first five rounds when negative selections were not included. For later rounds, the sequences recovered from peptide-beads were treated with counter selection before PCR amplification. The number of optimized PCR amplification cycles for each round was confirmed with agarose gel electrophoresis. Streptavidin sepharose high performance beads (GE Healthcare Life Sciences) were used to isolate the PCR products from the reaction mixture. The fluorophore-labeled amplicons were then separated from the biotinylated antisense DNA by eluting with 20 mM NaOH. Finally, the ssDNA was desalted with a NAP-5 column (GE Healthcare Life Sciences). The entire SELEX process was summarized in Table 2.

TABLE 2

Conditions used in each round of SELEX.

| Round | Library (conc., volume) | Negative (volume of beads, duration) | Positive (volume of beads, duration) | Negative (volume of beads, duration) | Washing (volume, times) | Suspended volume*[1] | # of repeated PCR cycles |
|---|---|---|---|---|---|---|---|
| 1 | 40 µM, 500 µL | — | 25 µL × 8*[2], 60 min | — | 500 µL × 2 | 100 µL | 20 repeats |
| 2 | 300 nM, 500 µL | — | 25 µL × 8, 45 min | — | 500 µL × 2 | 300 µL | 14 repeats |
| 3 | 300 nM, 500 µL | — | 25 µL × 8, 30 min | — | 500 µL × 2 | 300 µL | 14 repeats |
| 4 | 250 nM, 500 µL | — | 50 µL × 8, 30 min | — | 500 µL × 2 | 300 µL | 14 repeats |
| 5 | 250 nM, 500 µL | — | 50 µL × 8, 30 min | — | 500 µL × 3 | 300 µL | 12 repeats |
| 6 | 250 nM, 500 µL | — | 50 µL × 8, 30 min | 400 µL, 30 min | 500 µL × 3 | 500 µL | 12 repeats |
| 7 | 250 nM, 500 µL | — | 50 µL × 8, 30 min | 400 µL, 30 min | 1000 µL × 3 | 500 µL | 22 repeats |
| 8 | 250 nM, 300 µL | 125-1000 µL*[3], 30 min | 50 µL*[4] × 8, 30 min | 400 µL, 30 min | 1000 µL × 3 | 300 µL | 26 repeats |
| 9 | 250 nM, 300 µL | 400 µL, 30 min | 50 µL × 8, 30 min | 400 µL, 30 min | 1000 µL × 3 | 300 µL | 24 repeats |
| 10 | 250 nM, 300 µL | 1000 µL, 30 min | 50 µL × 8, 30 min | 1000 µL, 30 min | 1000 µL × 3 | 300 µL | 10 repeats*[5] |
| 11 | 250 nM, 300 µL | 1000 µL, 30 min | 50 µL × 8, 30 min | 1000 µL, 30 min | 1000 µL × 3 | 300 µL | 18 repeats*[5] |
| 12 | 250 nM, 300 µL | 1000 µL, 30 min | 100 µL*[6], 30 min | 1000 µL, 30 min | 1000 µL × 3 | 500 µL | 16 repeats |
| 13 | 250 nM, 300 µL | 1000 µL, 30 min | 100 µL, 30 min | 1000 µL, 30 min | 1000 µL × 3 | 500 µL | 16 repeats |
| 14 | 250 nM, 300 µL | 1000 µL, 30 min | 100 µL, 30 min | 1000 µL, 30 min | 1000 µL × 5 | 500 µL | 20 repeats |
| 15 | 250 nM, 300 µL | 1000 µL, 30 min | 100 µL, 30 min | 1000 µL, 30 min | 1000 µL × 5 | 500 µL | 14 repeats |
| 16 | 100 nM, 200 µL | 200 µL, 30 min | 100 µL, 30 min | 200 µL, 30 min | 1000 µL × 5 | 500 µL | 14 repeats |
| 17 | 100 nM, 200 µL | 200 µL, 30 min | 80 µL, 30 min | 200 µL, 30 min | 1000 µL × 5 | 500 µL | 12 repeats |

*[1]The solvent used to suspend DNA eluted from heated positive beads was DNase-free water in the first 5 rounds. That solvent was changed to PBS with additional 5 mM $Mg^{2+}$ for Round #6 and later rounds because negative incubations were introduced after positive incubations in these rounds.
*[2]All 8 types of peptide-beads (T181, T181P, S202, S202P, T231, T231P, S396S404, S396S404P) were used in the first 11 rounds. The concentration of the peptide solutions used to immobilize each of the his-tag peptides onto Ni-NTA beads was 400 µg/mL in the first 7 rounds.
*[3]Four subsequent counter incubations with 125 µL, 125 µL, 125 µL, and 1000 µL of Ni-NTA beads were executed before positive incubation in Round #8.
*[4]The concentration of the peptide solutions used to immobilize each of the his-tag peptides onto Ni-NTA beads for Round #8 and later rounds was increased to 800 µg/mL.
*[5]The DNA templates eluted from heated positive beads in Rounds #10 and #11 were diluted with another 300 µL of DNase-free water prior to PCR amplification.
*[6]Only T231-immobilized beads, instead of all 8 types of peptide-beads, were used as positive beads in Round #12 and later rounds.

Flow Cytometric Analysis of Enriched Pools or Aptamer Candidates

BD ACCURI™ C6 flow cytometry (BD Immunocytometry Systems) was used to monitor the enrichment of aptamer candidates during the selection process and to evaluate the binding specificity of the selected aptamer candidates. For each sample, 20 µL of peptide-beads or bare beads (~1.4×105 beads) was washed against 500 µL of PBS three times. After removing the supernatant, beads were suspended in 80 µL of buffer containing either DNA pool or aptamer candidate to be tested at 250 nM for 30 min, but the DNA concentration used was 100 nM instead of 250 nM when examining the saturation of fluorescent signal with the selection pools. Incubations were carried out at 4° C. unless stated otherwise. Afterwards, beads were washed against 500 µL of PBS with additional 5 mM Mg2+ twice and then were suspended in 80 µL of buffer for flow cytometric analysis.

Next-Generation Deep Sequencing of DNA Survivors

Enriched DNA pools from Rounds #15-17 were chosen for sequencing. Primers without FAM or biotin modification were used to amplify the DNA pools to be sequenced. The amplicons from each pool were then barcoded separately using TruSeq DNA library preparation kit (Illumina) for assorting the sequences afterwards. The samples were submitted to Illumina next-generation DNA sequencing at the University of Florida, ICBR Sequencing Core Facility. The sequencing results were analyzed using in-house software.

Chemical Synthesis and Purification of Aptamer Candidates

The 10 most abundant sequences from Round #17 were chemically synthesized by the standard phosphoramidite method using a 3400 DNA synthesizer (Applied Biosystems). Reagents for synthesis were purchased from Glen Research. The synthesized aptamer candidates were then purified by reversed phase HPLC (Varian Prostar), using a C18 column and triethylammonium acetate (TEAA, 0.1M)/acetonitrile (Fisher Scientific) as the mobile phase.

Sequence Truncation of the Selected Aptamers

The selected aptamers were truncated based on their secondary structures predicted by Integrated DNA Technologies OLIGOANALYZER® Tool. Shorter versions of each of the selected aptamers were synthesized and their binding abilities were evaluated by flow cytometry as described previously for full-length candidates.

Measurement of Binding Kinetics/Affinities of the Selected Aptamers

The binding affinities and binding kinetics of the selected aptamers were determined on an Octet RED384 instrument (Pall Fortebio). All measurements were performed on 384-well plates that were agitated at 1000 rpm at 30° C. The his-tag peptides were immobilized at a concentration of 5 µg/mL on Ni-NTA sensors for 10 minutes, followed by rinsing the sensors in PBS for 10 min. Then the sensors were brought into fresh association buffer (PBS with 5 mM Mg2+) to establish a baseline for another 10 min. For kinetic analysis, the peptide-immobilized sensors were transferred to the wells containing aptamer dilutions (1 µM, 1.5 µM, 2 µM, 3 µM, 4 µM) for the association step (10 min), and then moved to the wells with fresh buffer for the dissociation step (10 min). A reference sensor was used without the treatment with aptamer solution but others steps remained the same. When measuring the binding of aptamers with his-tag Tau441 protein (SignalChem), the experimental layout was the same as described above, except that the loading concentration of his-tag Tau441 protein was 1 µg/mL supplemented with 0.75 mM imidazole and the concentrations for aptamer dilutions were 0.75 µM, 1.5 µM, 3 µM, 6 µM, and 12 µM. Association rate constants ($k_{on}$), dissociation rate constants ($k_{off}$), and equilibrium dissociation constants ($K_d$) for each aptamer binding to its target peptide were calculated using the FORTEBIO® data analysis software 10.0.

Results and Discussion

Monitoring the Progression of Tau Aptamer Selection

Figure 3A:
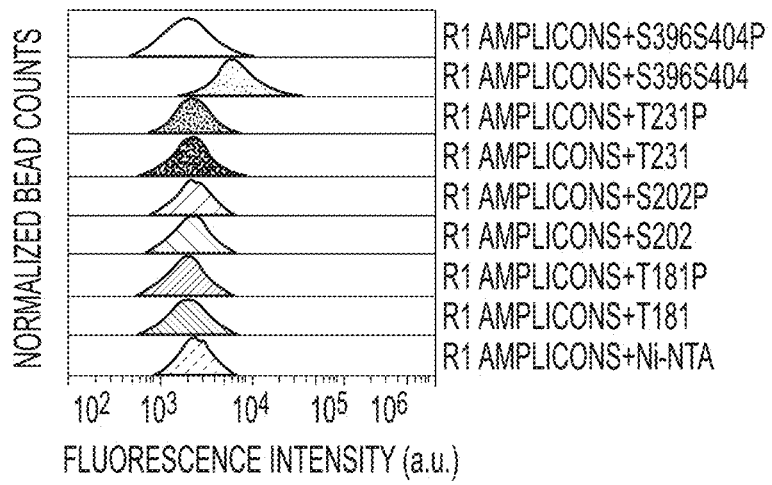
FIGS. 3A, 3B, and 3C illustrate the progress of aptamer selection against each of the peptides of interest, according to an embodiment of the disclosed invention.
Figure 3B:
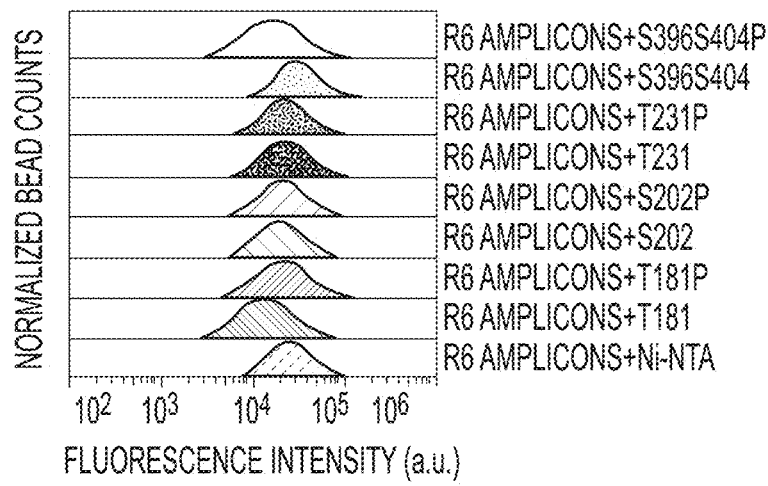
Figure 3C:
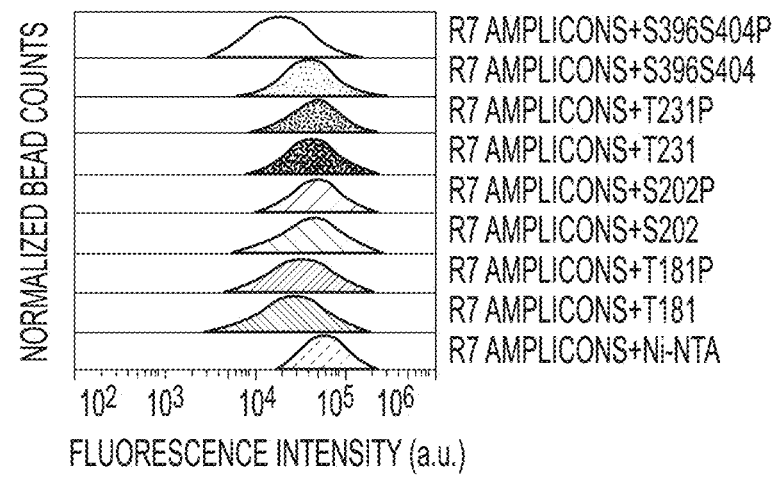
Figure 4:
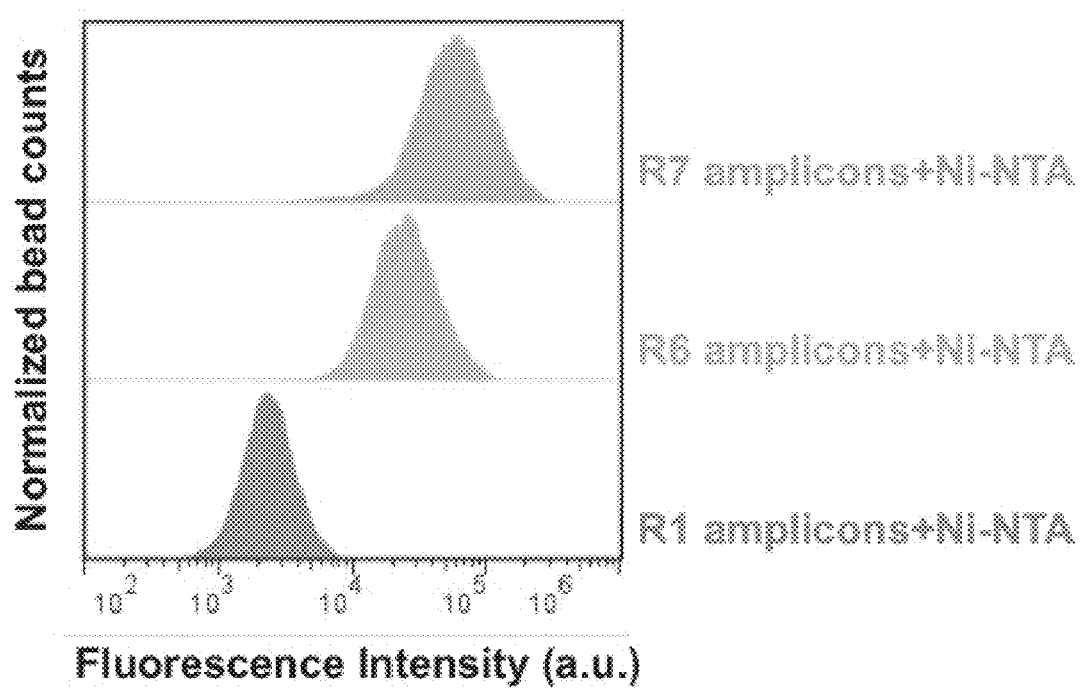
FIG. 4 illustrates binding of oligonucleotides amplified from Round #1, Round #6, and Round #7 to Ni-NTA beads, according to an embodiment of the disclosed invention.
Figure 5:
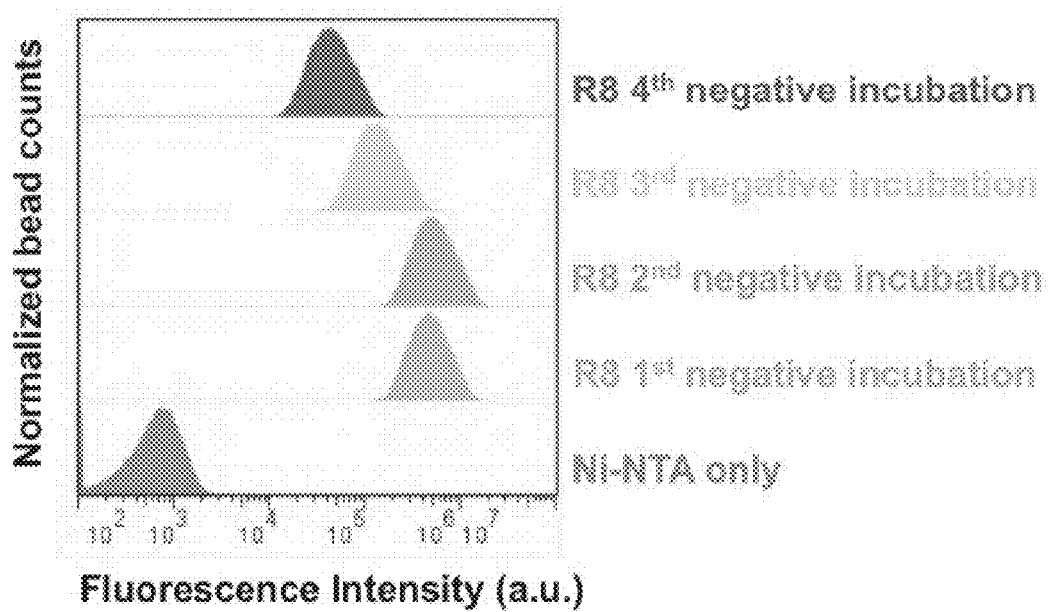
FIG. 5 illustrates decreasing binding intensities observed after involving stringent counter selections, according to an embodiment of the disclosed invention.

FIGS. 3a, 3b and 3c illustrate the progress of aptamer selection against each of the peptides of interest, according to an embodiment of the disclosed invention. Binding signal intensity was examined after Round #1 shown in FIG. 3A, Round #6 shown in FIG. 3B, and Round #7 shown in FIG. 3A. Fluorescent signals detected came from FAM-labeled oligonucleotides bound on beads and were monitored using flow cytometry. FIG. 4 illustrates binding of oligonucleotides amplified from Round #1, Round #6, and Round #7 to Ni-NTA beads, according to an embodiment of the disclosed invention. The recovered pools showed an increasing trend of binding to the Ni-NTA beads throughout the rounds. FIG. 5 illustrates decreasing binding intensities observed after involving stringent counter selections, according to an embodiment of the disclosed invention. Four subsequent negative incubations were conducted before positive incubation in Round #8. The fluorescence intensities detected were in accordance with the relative amount of ssDNA bound on each portion of negative beads.

The selection process began with a random library containing 20 nmol of primer-flanked, 66-nucleotide-long, single-stranded DNA, which approximately had $1.2 \times 10^{16}$ sequences. After incubating the initial DNA library with a mixture of peptide-beads, the unbound DNA strands were washed off. The retained oligonucleotides on peptide-beads were eluted by denaturing the secondary structure of DNA through heating and then were collected in supernatant. The recovered survivors were amplified by PCR and the amplicons generated were used as the library for the next round. Sequential rounds were carried out with similar procedures until counter-selection with bare Ni-NTA beads was introduced. Started from Round #6, the supernatant recovered from positive incubation was to be submitted to the negative incubation with bare Ni-NTA beads to remove the sequences that might preferably adhere to the surface of the beads. Such post-counter-selection was employed in all following rounds. The enrichment was firstly examined after 7 rounds. The amplicons produced in Round #1, Round #6, and Round #7 were used to test the binding of the recovered pools against each of the 8 putative peptides of target. The fluorescent signals on Ni-NTA beads and peptide-beads were measured using flow cytometry. As shown in FIG. 3, the DNA pools obtained after 7 rounds did not really exhibit binding preference to any of the desired targets compared to their binding towards negative beads. Instead, the oligonucleotides amplified seemed to have an upward trend in binding to the bare Ni-NTA beads throughout the rounds (FIG. 4). Based on this, a much more stringent counter selection was executed before positive incubation in Round #8. Four subsequent negative incubations were performed with 125 µL, 125 µL, 125 µL, and 1000 µL of Ni-NTA beads, respectively. The relative amount of ssDNA bound on each portion of negative beads was examined as expressed in FIG. 5. The concentration, or the population, of the undesired sequences was decreased in a noticeable manner in the third and the fourth negative incubations.

Figure 6A:
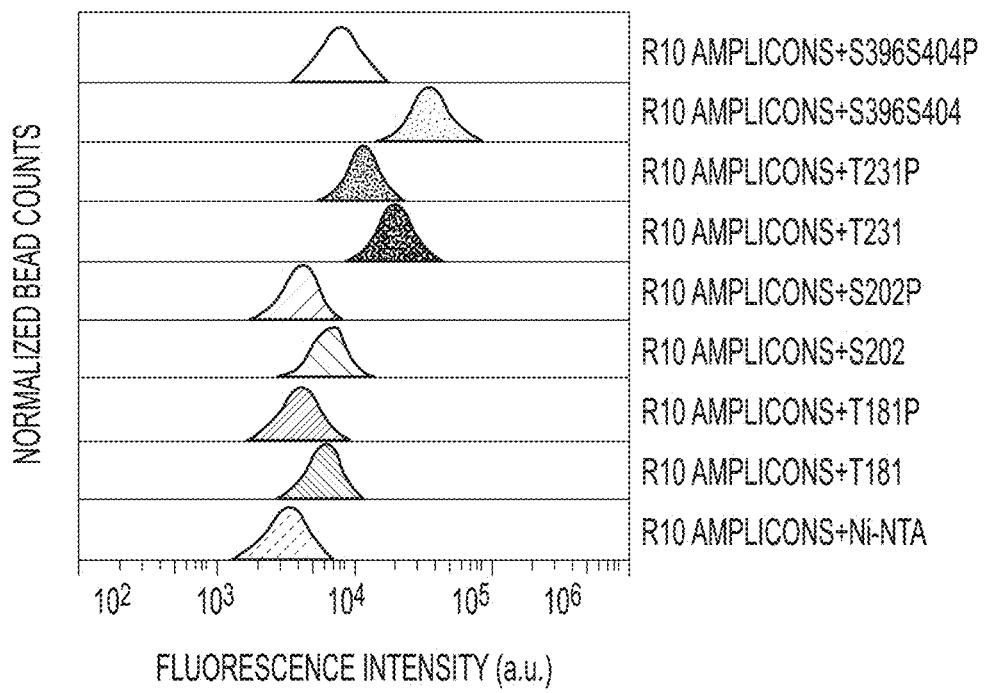
FIGS. 6A and 6B illustrate evaluation of the SELEX progress, according to an embodiment of the disclosed invention.
Figure 6B:
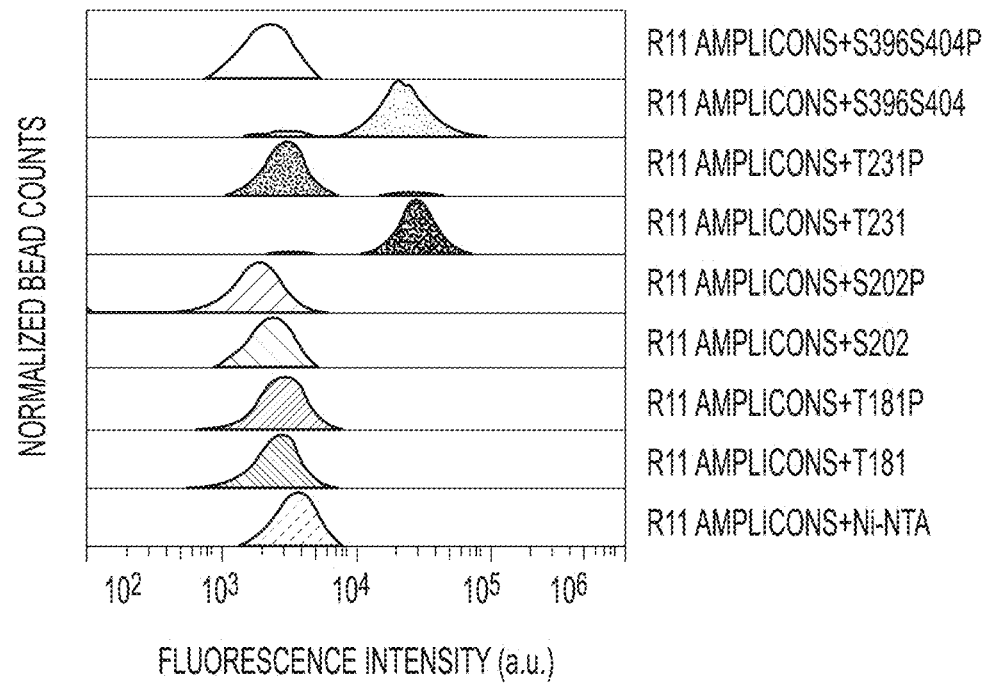

FIGS. 6A and 6B illustrate evaluation of the SELEX progress, according to an embodiment of the disclosed invention. Binding intensity was evaluated with amplicons obtained in Round #10 shown in FIG. 6A and Round #11 shown in FIG. 6B. Both ssDNA pools tested showed a preference binding towards T231 and S396S404 over other peptides. FIGS. 7A, 7B, 7C and 7D, and Table 3 illustrate binding test with reference sequences, according to an embodiment of the disclosed invention. Sequence Ref1 (shown in FIG. 7A), Ref2 (shown in FIG. 7B), Ref3 (shown in FIG. 7C), and Ref4 (shown in FIG. 7D) were used to investigate binding bias between oligonucleotides and peptides. Higher non-specific binding was observed with S396S404 peptide regardless of the sequence of the binding partner.

TABLE 3

Reference sequences used in binding test.

| Name | Sequence 5'→3' |
|---|---|
| Ref1 | GCGGAGCGTGGCAGG (SEQ ID NO: 36) |
| Ref2 | AACGAGAAGCGCGATCACAT (SEQ ID NO: 37) |
| Ref3 | CTTCTGCCCGCCTCCTTCC (SEQ ID NO: 38) |
| Ref4 | ATCCAGAGTGACGCAGCACCAATAAATCTAGCCGGGGT ATCGGTGGACACGGTGGCTTAGT (SEQ ID NO: 39) |

The supernatant collected after the fourth negative incubation then was carried to the 8th round of positive incubation, in which the concentration of the peptide solutions used to modify Ni-NTA beads was doubled to 800 µg/mL. Moving forward, the following selection rounds were conducted with sandwiched negative incubations to eliminate the possibility of enriching any oligonucleotides recognizing the surface of the beads and with positive beads prepared with more concentrated peptide solutions (800 µg/mL) to raise the recovery rate of the desired candidates. The conditions used were summarized in Table 1. The SELEX progress was then evaluated again with amplicons obtained in Round #10 and Round #11. Both ssDNA pools tested favored T231 and S396S404 over other peptides, demonstrate these two tau fragments were potentially the most promising targets (FIG. 6). A reference test was engaged at this point to circumvent any predisposition to higher non-specific binding with each peptide of interest. Four oligonucleotides were used as reference sequences. Three of them (Ref1-Ref3) had been reported to have binding affinities towards full-length Tau 381 and Tau 410 proteins in either single-stranded or double-stranded forms, yet their binding sites remained unknown.134 Ref4 was used as a reference in comparable length to the DNA library used for tau SELEX. It turned out the binding bias was observed with S396S404 peptide regardless of which reference sequence was used (FIG. 7) On the other hand, no significant background binding was found between T231 and the reference sequences, indicating the binding enhancement on T231 seen in FIG. 6 was genuinely attributed to the evolution of T231 DNA binders along the selection process.

Figure 8:
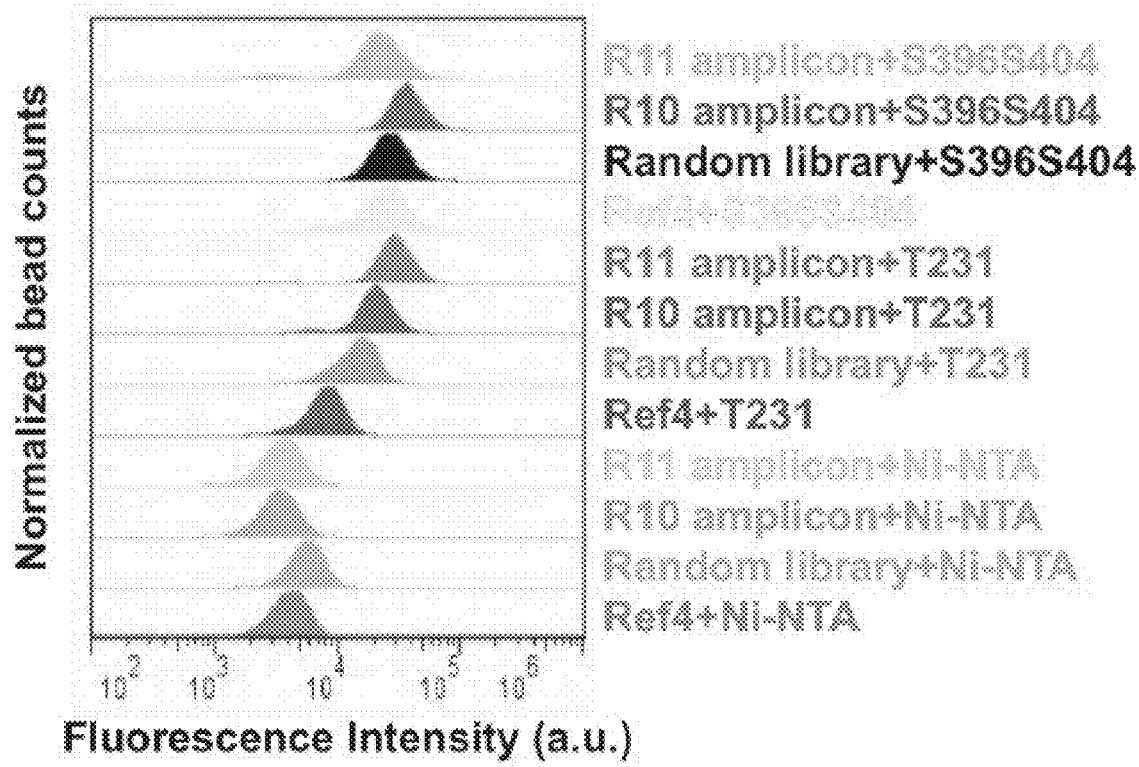
FIG. 8 illustrates Fluorescence intensities detected on Ni-NTA, T231, and S396S404 beads after incubated with fluorophore-labeled sequences, including Ref4, a random DNA library, amplicons obtained in Round #10, and amplicons obtained in Round #11, according to an embodiment of the disclosed invention.
Figure 9:
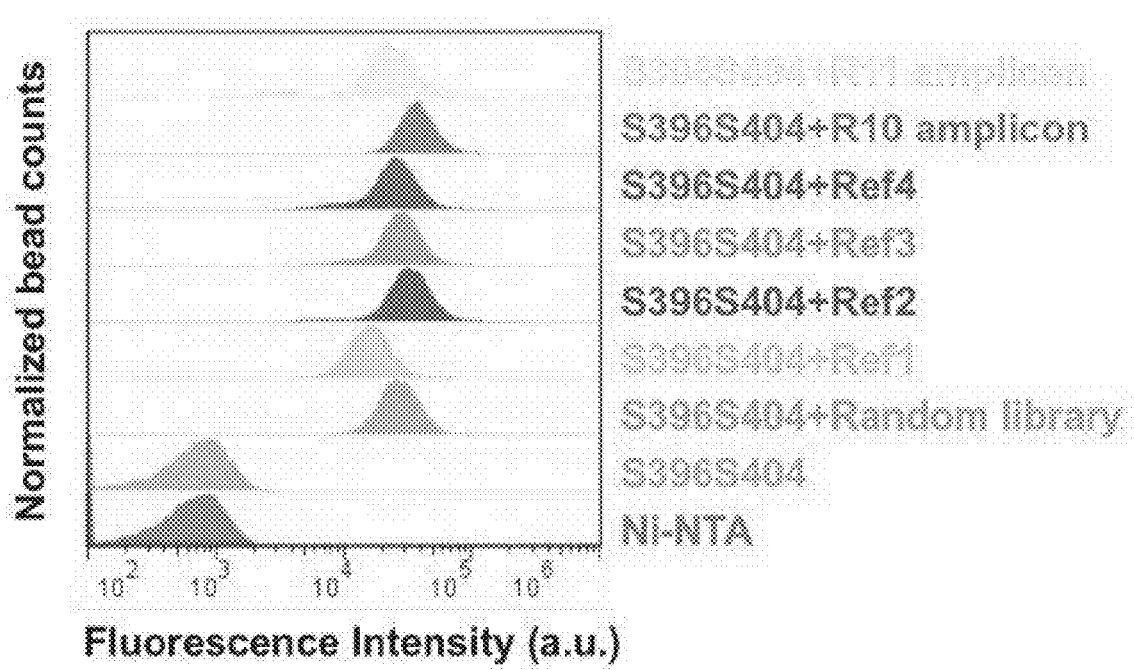
FIG. 9 illustrates binding test with S396S404 peptide using different DNA pools and sequences, according to an embodiment of the disclosed invention.

FIG. 8 illustrates Fluorescence intensities detected on Ni-NTA, T231, and S396S404 beads after incubated with fluorophore-labeled sequences, including Ref4, a random DNA library, amplicons obtained in Round #10, and amplicons obtained in Round #11, according to an embodiment of the disclosed invention. FIG. 9 illustrates binding test with S396S404 peptide using different DNA pools and sequences, according to an embodiment of the disclosed invention. S396S404 did not discriminate different DNA samples but possessed an inherent affinity to ssDNA.

To better recapitulate the conclusion here, the binding of Ref4, a DNA library contained randomized mixture of sequences, amplicons obtained in Round #10, and amplicons obtained in Round #11 towards Ni-NTA, T231, and S396S404 beads were depicted side by side in FIG. 8. All four DNA pools used here expressed same level of low binding strength to Ni-NTA beads, representing that the sandwiched counter selections were efficient. As for T231 beads, a gradual increase of binding intensities between the random library and oligonucleotides amplified from DNA survivors in Round #10 and Round #11 was found, implying the likelihood of T231 being target of aptamers to be selected. Nevertheless, the binding intensities observed on S396S404 beads with amplicons obtained in Round #10 and Round #11 were misleading. Even though the fluorescence intensities on S396S404 beads were much stronger than that on Ni-NTA beads, S396S404 did not really discriminate different DNA pools (FIG. 9), meaning the fluorescent signals detected with S396S404 beads came from an inherent affinity between S396S404 peptide and ssDNA rather than S396S404 being the anticipated target at this point. T231 peptides were then taken as the sole target used in positive incubations for the next six rounds.

Figure 10:
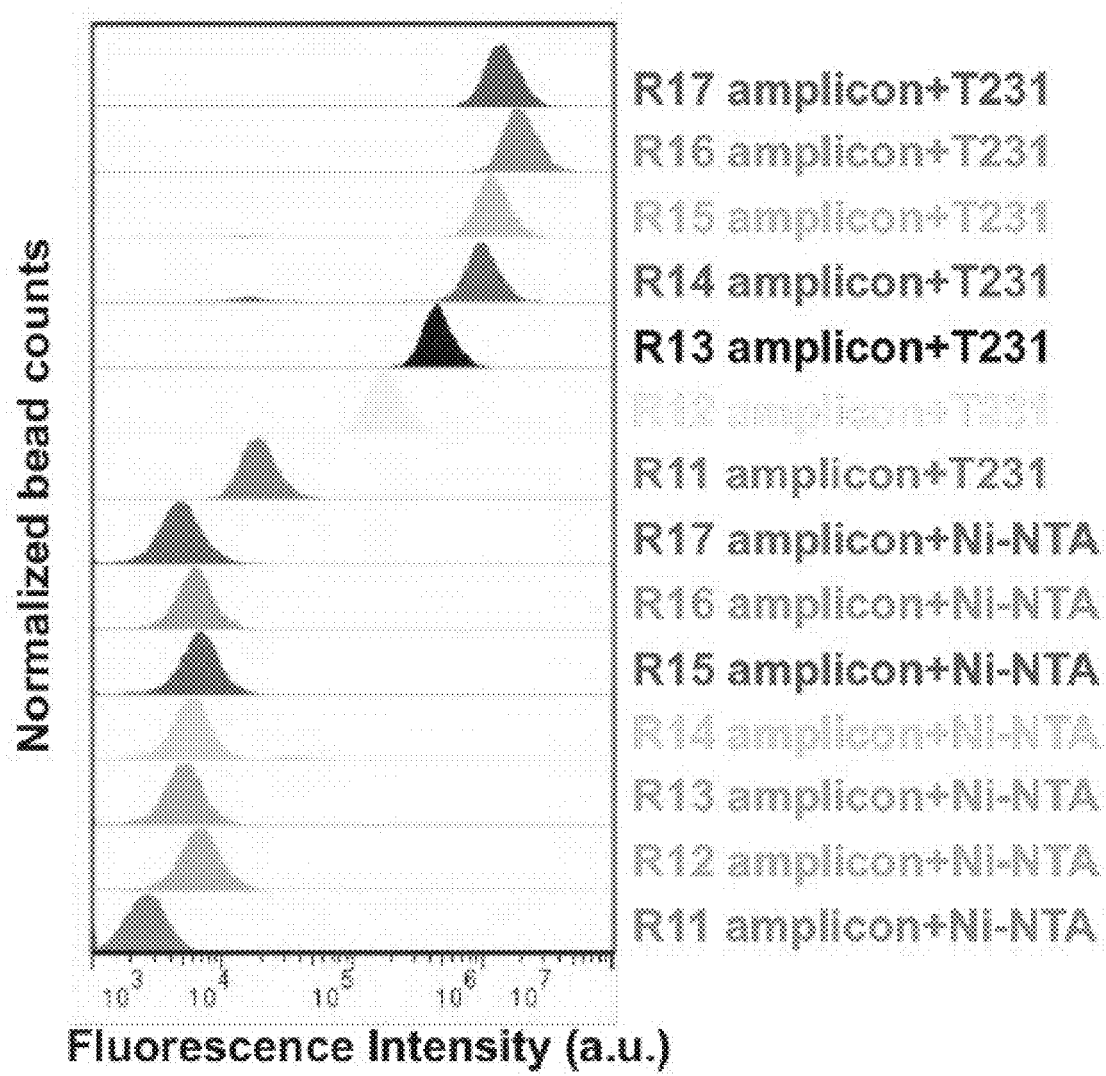
FIG. 10 illustrates the binding strengths of amplicons from Round #12 to Round #17 against Ni-NTA beads and T231 beads, according to an embodiment of the disclosed invention.
Figure 11:
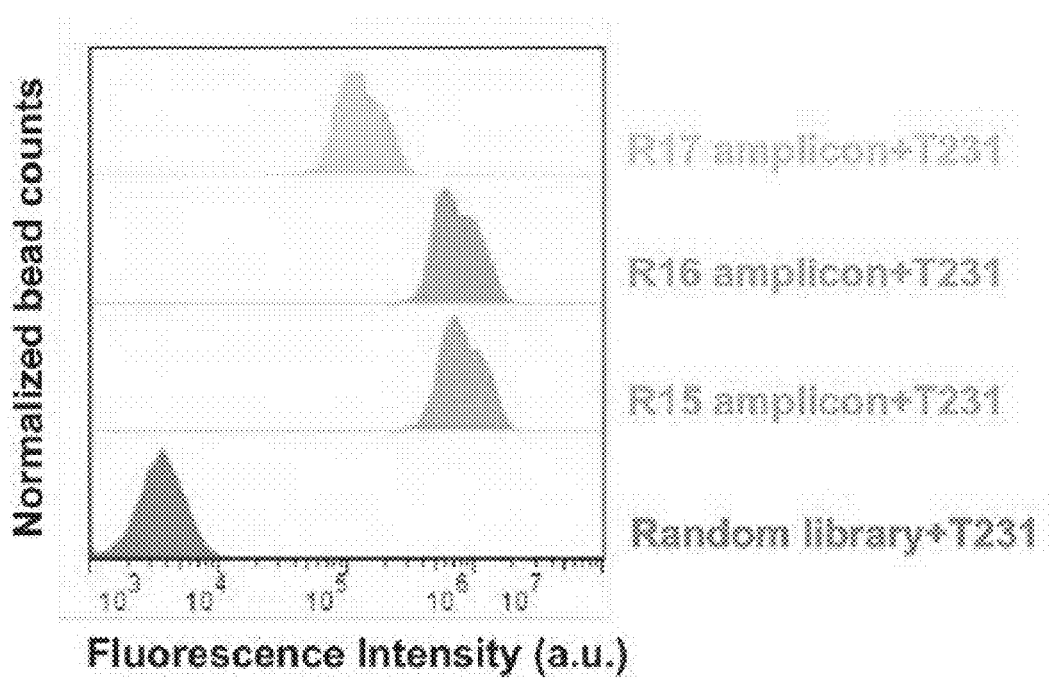
FIG. 11 illustrates binding test against T231 peptide with 100 nM of amplicons acquired from Round #15, Round #16, and Round #17, according to an embodiment of the disclosed invention.
Figures 12I, 12J:
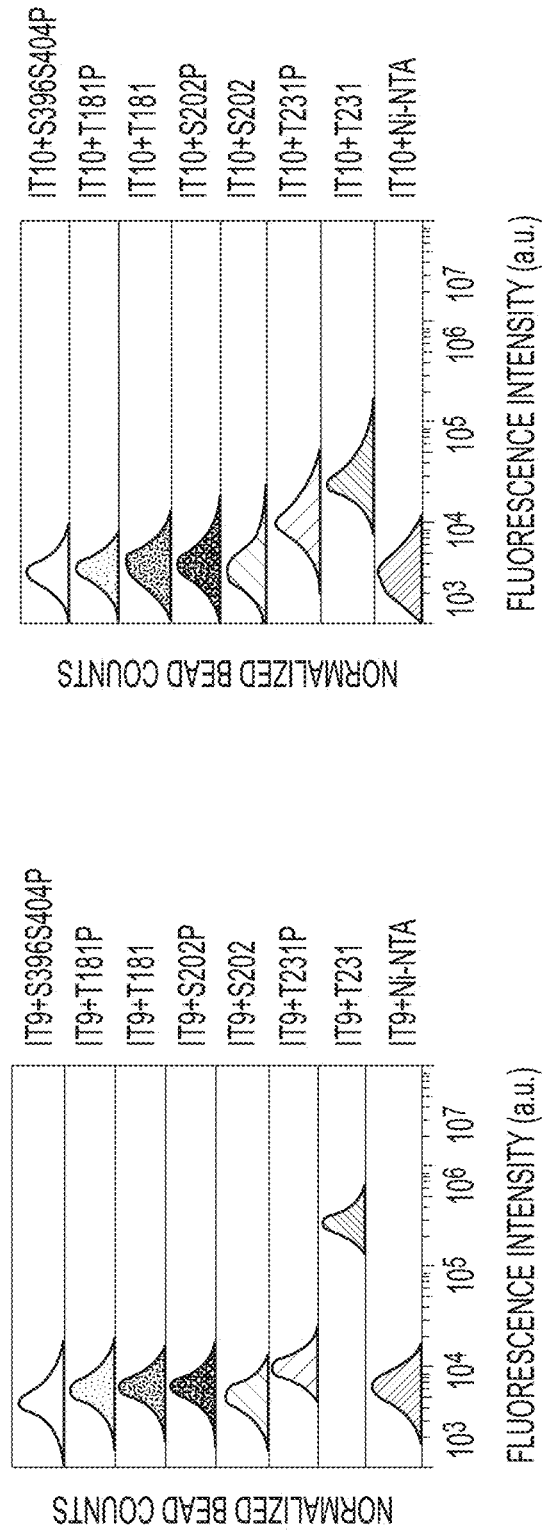

The binding strengths of the resulting PCR products from Round #12 to Round #17 against Ni-NTA beads and T231 beads evaluated by flow cytometry were shown in FIG. 10. A substantial boost in fluorescence intensity detected on T231 beads was found with amplicons acquired in Round #12, in which T231-immobilized beads, instead of all 8 types of peptide-beads, were used alone in the positive selection for the first time. While the screened ssDNA pools steadily presented low binding to Ni-NTA beads, the fluorescent signals on T231 beads stopped increasing as significantly between Round #14 and Round #17, demonstrating the saturated binding of the enriched pools to T231 beads had been achieved. Signals were evaluated by flow cytometry. Since the signal intensity detected from Round #16 almost reached the upper detection limit of the instrument, another test using only 100 nM, instead of 250 nM, of the amplicons was carried out to truthfully interpret the discrepancy between Round #15, Round #16, and Round #17 (FIG. 11). FIG. 11 illustrates binding test against T231 peptide with 100 nM of amplicons acquired from Round #15, Round #16, and Round #17, according to an embodiment of the disclosed invention. PCR products obtained in Round #15, Round #16, and Round #17 were then barcoded and submitted for next-generation deep sequencing.

Identification of the Selected Aptamers and their Binding Targets

FIGS. 12A through 12J illustrate primary binding analysis between the top 10 aptamer candidates and their prospective target of peptides, according to an embodiment of the disclosed invention. Sequences IT1, IT4, IT5, IT6, and IT9 appeared to be aptamers specifically targeting T231 peptide without phosphorylation. Sequence IT2 demonstrated a unique binding profile on three of the peptides (T231, T231P, and S202). Sequence IT3 overlooked the phosphorylated site and recognized both T231 and T231P.

Equal moles of barcoded amplicons from Round #15, Round #16, and Round #17 were sequenced. The number of reads yielded for Pool #15, Pool #16, and Pool #17 were 628,462, 675,441, 628,288, respectively. The sequences were analyzed using in-house software. The top 10 most abundant sequences found in Pool #17 were listed in Table 4 and were chemically synthesized and labeled with FAM at the 5' end, followed by purification using HPLC. Primary binding analysis examined by flow cytometry was performed by incubating each of the 7 peptide-beads with 250 nM of each aptamer candidate to screen the binding capacity and corresponding binding targets. S396S404 peptide was not included here to avoid misleading readout with the analysis. As shown in FIG. 12, five of the candidates (IT1, IT4, IT5, IT6, and IT9) were found to possess strong and specific binding to T231 peptide, while IT3 overlooked the phosphorylated site and bound to both T231 and T231P. Sequence IT2, on the other hand, demonstrated a unique binding profile. Not only did IT2 recognize both T231 and T231P, but it also bound to S202. In addition, IT8, IT9, and IT10 were found bearing high level of sequence homology to IT3, IT5, and IT2, respectively, except for one nucleotide at position 19, which is the very first nucleotide next to the PCR forward primer region (Table 5). IT9 and its predecessor IT5 displayed similar binding strength towards T231, demonstrating the nucleotide at position 19 for these two resembling sequences had no significant impact on their binding abilities to T231. However, IT8 and IT10 both lost their binding abilities to the prospective targets found with IT3 and IT2, proving that the binding strength of an aptamer could be greatly compromised by altering merely one nucleotide within the crucial binding region. Yet, based on the fact that IT8 and IT10 did not really manifest any binding preference to neither of the peptides, they are more likely the byproducts resulted from PCR amplification with edge effect than the candidates evolved from partition with the targets. Table 1 shows the full nucleotide sequences of all Tau aptamers and their truncated Tau aptamers capable of binding to one or more phosphoarylable epitopes of Tau protein.

TABLE 4

The sequences of the most abundant 10 candidates selected with Tau peptides after 17 rounds and their relative percentages in 3 pools sequenced.

| Name | % in R15 | % in R16 | % in R17 | Sequence 5'→3' (showing only the randomized region) |
|---|---|---|---|---|
| IT1 | 18.8 | 32.8 | 46.2 | TGCTTGGTCCTCCCGGGGTTCT GGAAAAGC (SEQ ID NO: 40) |
| IT2 | 16.2 | 23.5 | 21.5 | AAGGACTGCTTAGGATTGCGAT GATTCAGG (SEQ ID NO: 41) |
| IT3 | 15.9 | 11.9 | 8.35 | GGGGAGAGTGGTGGGGCGGGGG CCGGATCC (SEQ ID NO: 42) |
| IT4 | 18.1 | 10.0 | 7.75 | GGGTTGGCCGGGCAGCGGGGGG TAGGCTTG (SEQ ID NO: 43) |
| IT5 | 9.19 | 7.20 | 4.43 | GGCGGGGGGTCAGGTCGGGTA AGGTGAGC (SEQ ID NO: 44) |
| IT6 | 0.150 | 0.303 | 0.794 | GTTGTCGTCAGAGGTTATAACC TGAACTCG (SEQ ID NO: 45) |
| IT7 | 1.29 | 0.917 | 0.458 | GGGGGCTGCTTAGGATTGCGGT TGTTTGTG (SEQ ID NO: 46) |

TABLE 4-continued

The sequences of the most abundant 10 candidates selected with Tau peptides after 17 rounds and their relative percentages in 3 pools sequenced.

| Name | % in R15 | % in R16 | % in R17 | Sequence 5'→3' (showing only the randomized region) |
|---|---|---|---|---|
| IT8 | 0.198 | 0.238 | 0.233 | TGGGAGAGTGGTGGGGCGGGGG CCGGATCC (SEQ ID NO: 47) |
| IT9 | 0.211 | 0.222 | 0.221 | TGCGGGGGGTCAGGTCGGGTA AGGTGAGC (SEQ ID NO: 48) |
| IT10 | 0.236 | 0.318 | 0.209 | GAGGACTGCTTAGGATTGCGAT GATTCAGG (SEQ ID NO: 49) |

TABLE 5

Sequences IT8, IT9, and IT10 were found bearing high level of sequence homology to IT3, IT5, and IT2, respectively.

| Group | Name | Sequence 5'→3' (showing only the randomized region) | Target | Mutant site |
|---|---|---|---|---|
| Pair 1 | IT8 | TGGGAGAGTGGTGGGGCGG GGGCCGGATCC (SEQ ID NO: 47) | X | NT19: G→T |
| | IT3 | GGGGAGAGTGGTGGGGCGG GGGCCGGATCC (SEQ ID NO: 42) | T231, T231P | |
| Pair 2 | IT9 | TGCGGGGGGTCAGGTCGGG GTAAGGTGAGC (SEQ ID NO: 48) | T231 | NT19: G→T |
| | IT5 | GGCGGGGGGTCAGGTCGGG GTAAGGTGAGC (SEQ ID NO: 44) | T231 | |
| Pair 3 | IT10 | GAGGACTGCTTAGGATTGC GATGATTCAGG (SEQ ID NO: 49) | X | NT19: A→G |
| | IT2 | AAGGACTGCTTAGGATTGC GATGATTCAGG (SEQ ID NO: 41) | T231, T231P, S202 | |

The discrepancy only occurred at the 19th nucleotide. IT9 retained the binding ability to T231 as of IT5, but IT8 and IT10 lost the binding affinities to the prospective targets found with IT3 and IT2.

Sequence Truncation of the Selected Aptamers

The above selected aptamers were full-length sequences evolved from the initial library used in SELEX, which contained the fixed primer binding regions on both ends to serve the PCR amplification process. Often times, the full-length aptamers came with some redundant motifs, either within the primer binding sites or in the randomized region. Accordingly, the full-length aptamers could be truncated into a minimal functional sequence without compromising the direct interaction with the target or the folding structure that facilitated the target binding. Sequence truncation had been carried out successfully to obtain functional aptamers restricted to the minimal target-binding domain, most of which were less than 40 nucleotides long and were predicted to be in the hairpin (stem-loop) or hairpin-with-an-additional-loop structure.135-139 The approach used here to remove the extraneous nucleotides from the full-length aptamers based on analysis of their secondary structures predicted by Integrated DNA Technologies OLIGOANA-LYZER® Tool. Aptamers IT1, IT2, IT3, IT4, IT5, and IT6 were chosen for sequence truncation. Since it had been reported that fluorescein would be quenched by around 30% when in proximity to guanine,140 two to three T-bases were added as a spacer next to fluorescein if the truncated sequence ended with G-base or G-C pair in the stem. The truncated candidates from each known aptamer were synthesized and tested successively. Their binding abilities were evaluated by flow cytometry as described previously for full-length candidates.

Figure 13A:
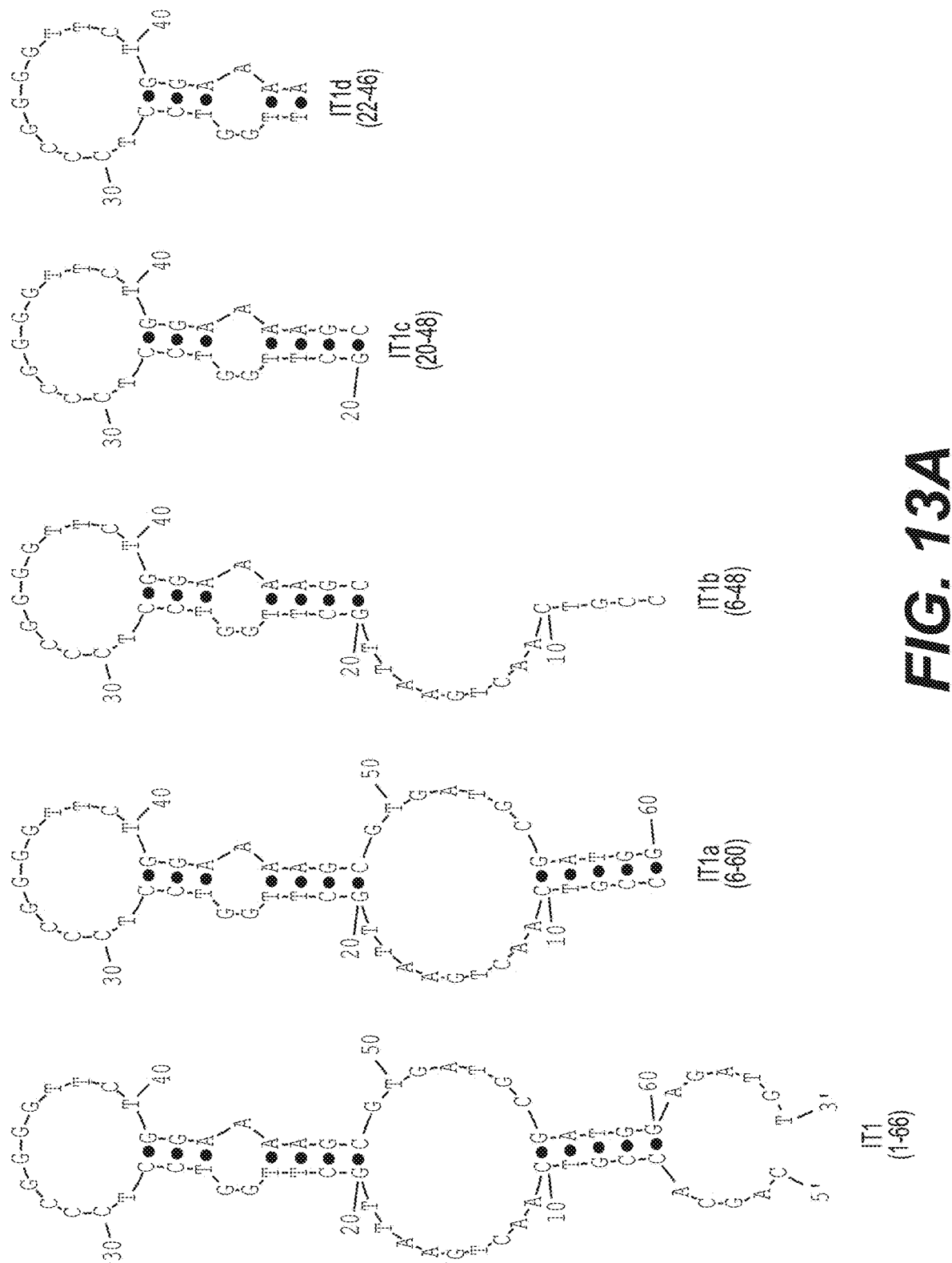
FIGS. 13A and 13B illustrate sequence optimization of IT1, according to an embodiment of the disclosed invention.
Figure 13B:
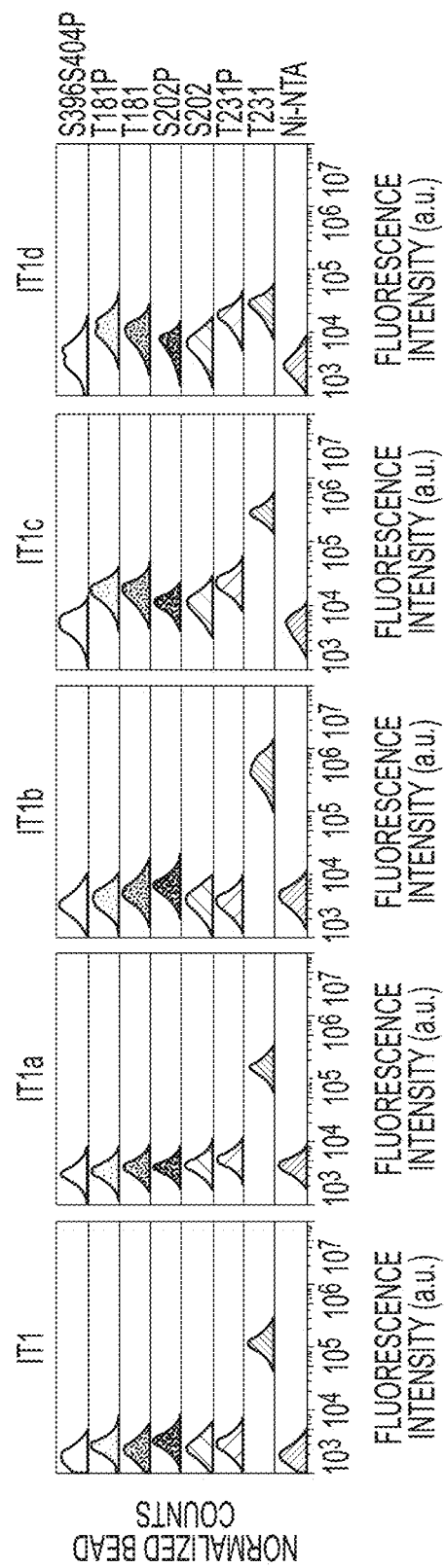

FIGS. 13A and 13B illustrate sequence optimization of IT1, according to an embodiment of the disclosed invention. (A) Predicted secondary structures of aptamer IT1 (SEQ ID NO: 1) and its truncated candidates, IT1a (SEQ ID NO: 8), IT1b (SEQ ID NO: 9), IT1c (SEQ ID NO: 10), and IT1d (SEQ ID NO: 11). (B) Truncated candidates IT1a, IT1b, and IT1c showed slightly stronger binding abilities to T231 compared to full-length aptamer IT1. However, the binding strength was lost when further truncating the stem of IT1c into IT1d. As shown in FIGS. 13A and 13B, the shorter versions of aptamer IT1, except for IT1d, were found to have slightly stronger binding abilities towards T231, demonstrating the smallest candidate IT1c was the binding motif, which was less than half in length compared to IT1.

Figure 14A:
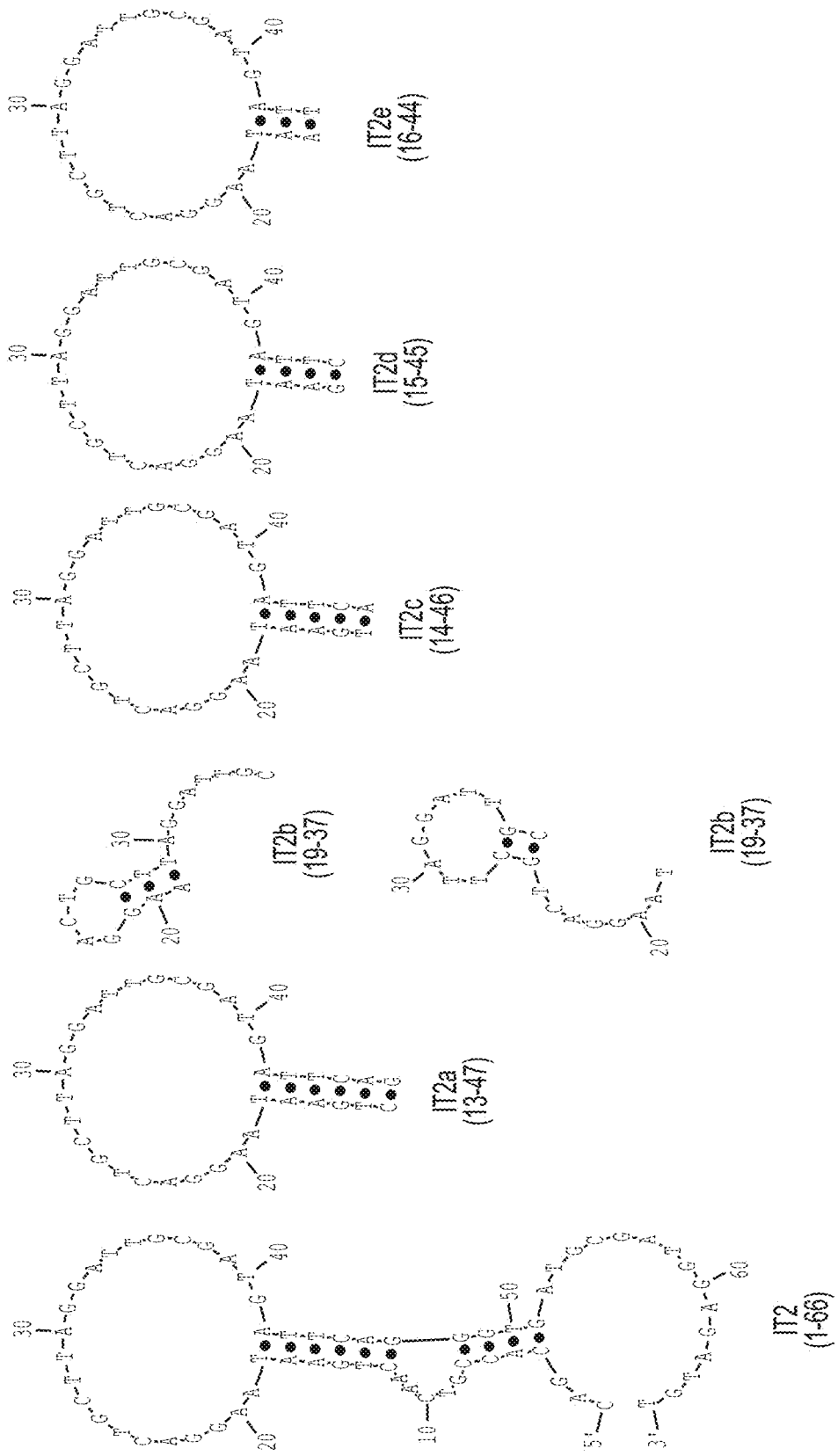
FIGS. 14A and 14B illustrate sequence optimization of IT2, according to an embodiment of the disclosed invention.
Figure 14B:
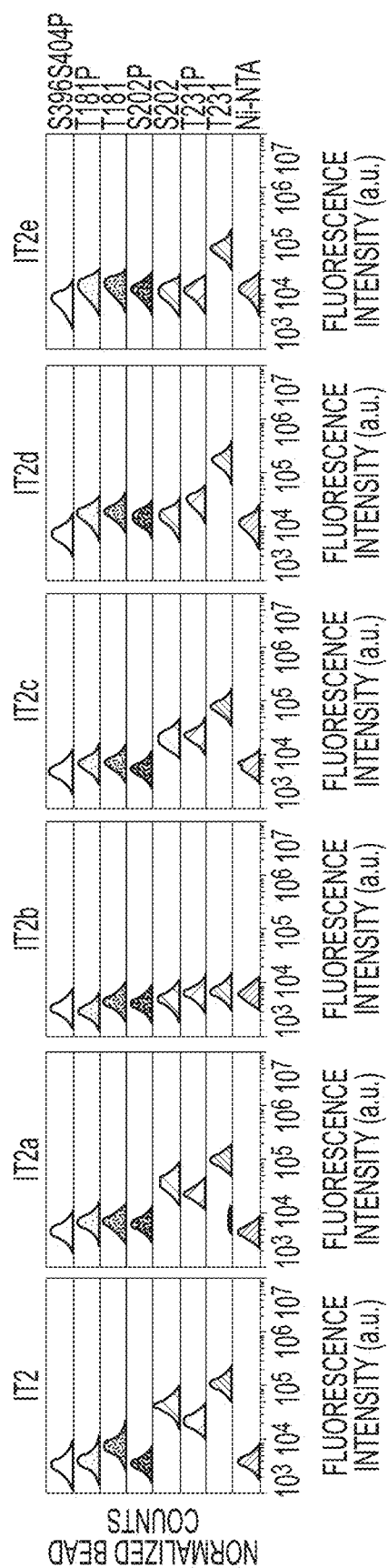

FIGS. 14A and 14B illustrate sequence optimization of IT2, according to an embodiment of the disclosed invention. (A) Predicted secondary structures of aptamer IT2 (SEQ ID NO: 2) and its truncated candidates, IT2a (SEQ ID NO: 12), IT2b ((1) SEQ ID NO: 13 and (2) SEQ ID NO: 50, respectively, in order of appearance), IT2c (SEQ ID NO: 14), IT2d (SEQ ID NO: 15), and IT2e (SEQ ID NO: 16). (B) Sequence truncation was done successfully with IT2a and IT2c. However, further truncation resulted in gradual loss of binding ability as seen with IT2d and IT2e. Binding strength was lost completely with sequence IT2b.

Figure 15A:
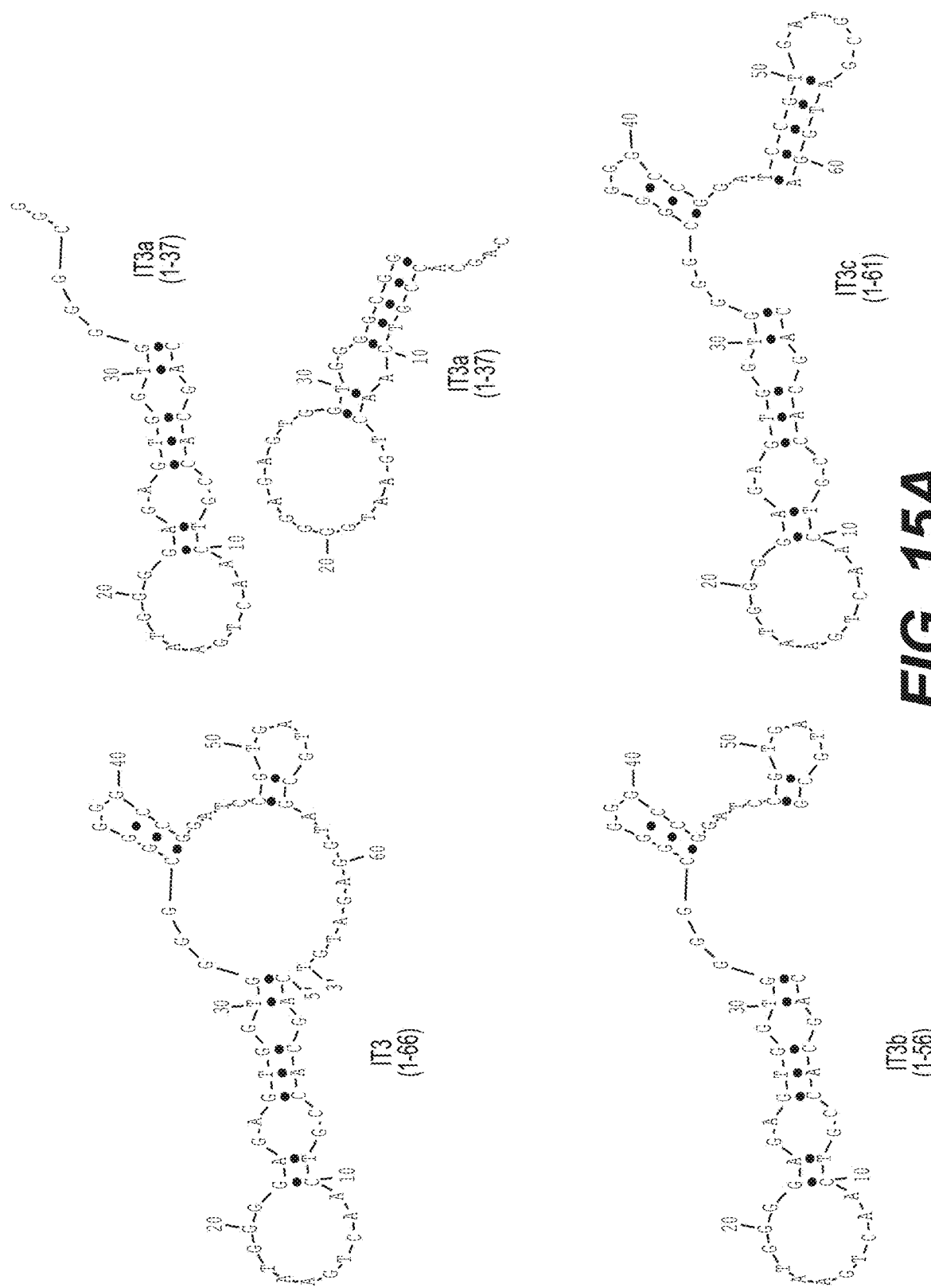
FIGS. 15A and 15B illustrate sequence optimization of IT3, according to an embodiment of the disclosed invention.
Figure 15B:
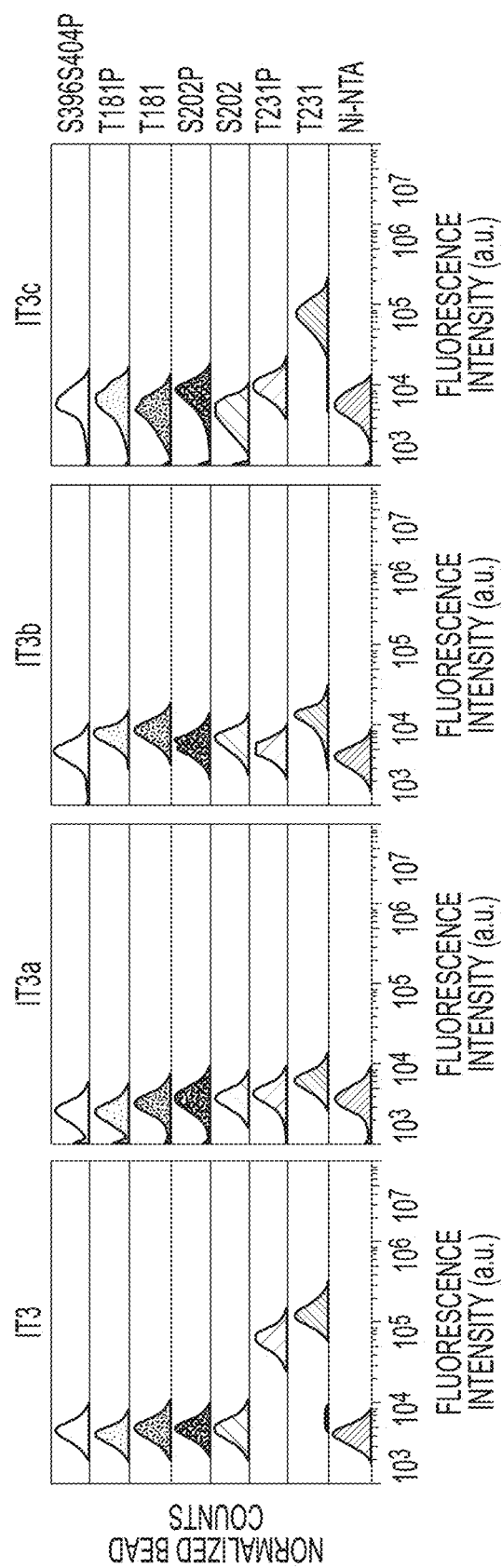

FIGS. 15A and 15B illustrate sequence optimization of IT3, according to an embodiment of the disclosed invention. (A) Predicted secondary structures of aptamer IT3 (SEQ ID NO: 3) and its truncated candidates, IT3a (SEQ ID NO: 17,), IT3b (SEQ ID NO: 18), IT3c (SEQ ID NO: 19), and IT3d. (B) Binding preference to T231 and T231P was lost completely with sequence IT3a. The binding affinity to T231 was then gradually recovered when the removed nucleotides were appended back to the sequence (IT3c), while the binding to T231P was extremely susceptible to any change made to the parent sequence.

Figure 16A:
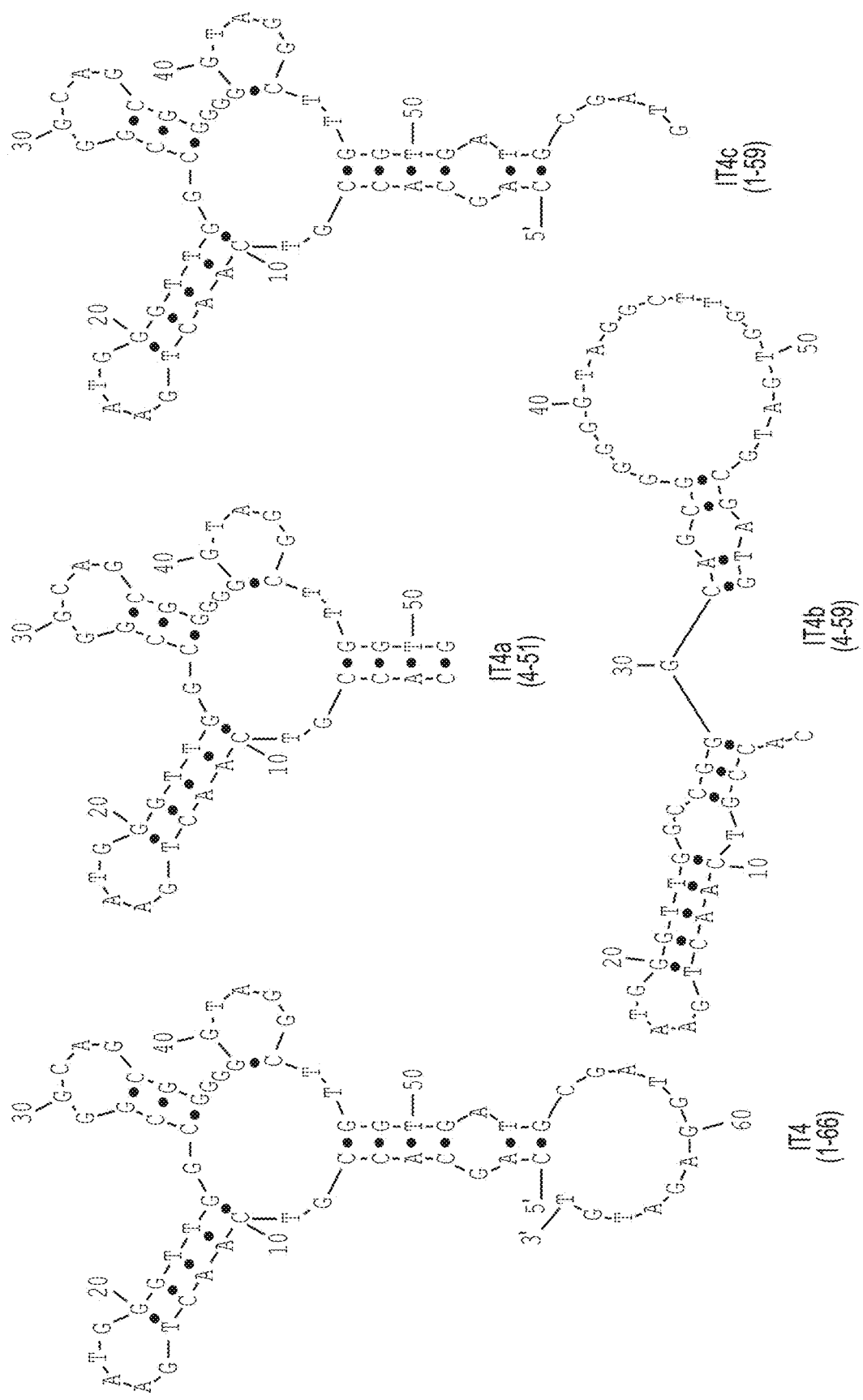
FIGS. 16A and 16B illustrate sequence optimization of IT4, according to an embodiment of the disclosed invention.
Figure 16B:
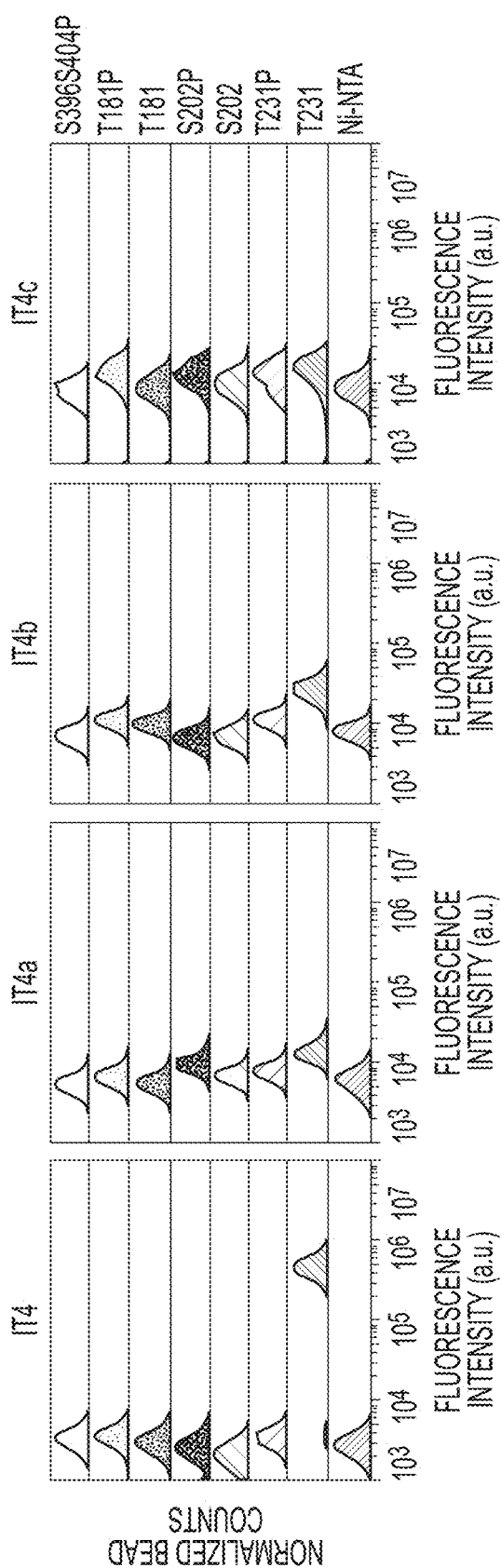

FIGS. 16A and 16B illustrate sequence optimization of IT4, according to an embodiment of the disclosed invention. (A) Predicted secondary structures of aptamer IT4 (SEQ ID NO: 4) and its truncated candidates, IT4a (SEQ ID NO: 20), IT4b (SEQ ID NO: 21), and IT4c (SEQ ID NO: 22). (B) None of the truncated candidates for IT4 showed binding affinity to T231.

Figure 17A:
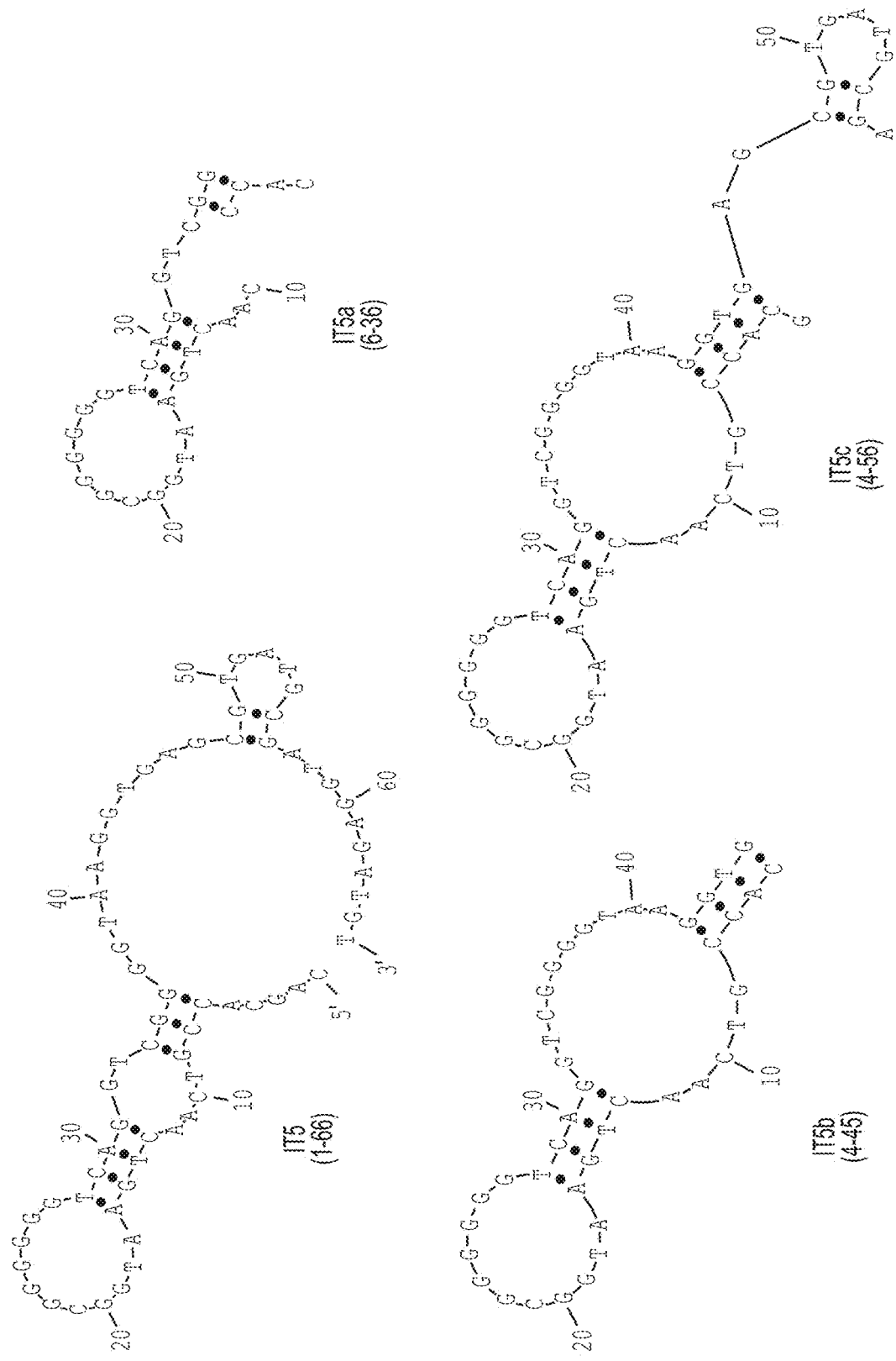
FIGS. 17A and 17B illustrate sequence optimization of IT5, according to an embodiment of the disclosed invention.
Figure 17B:
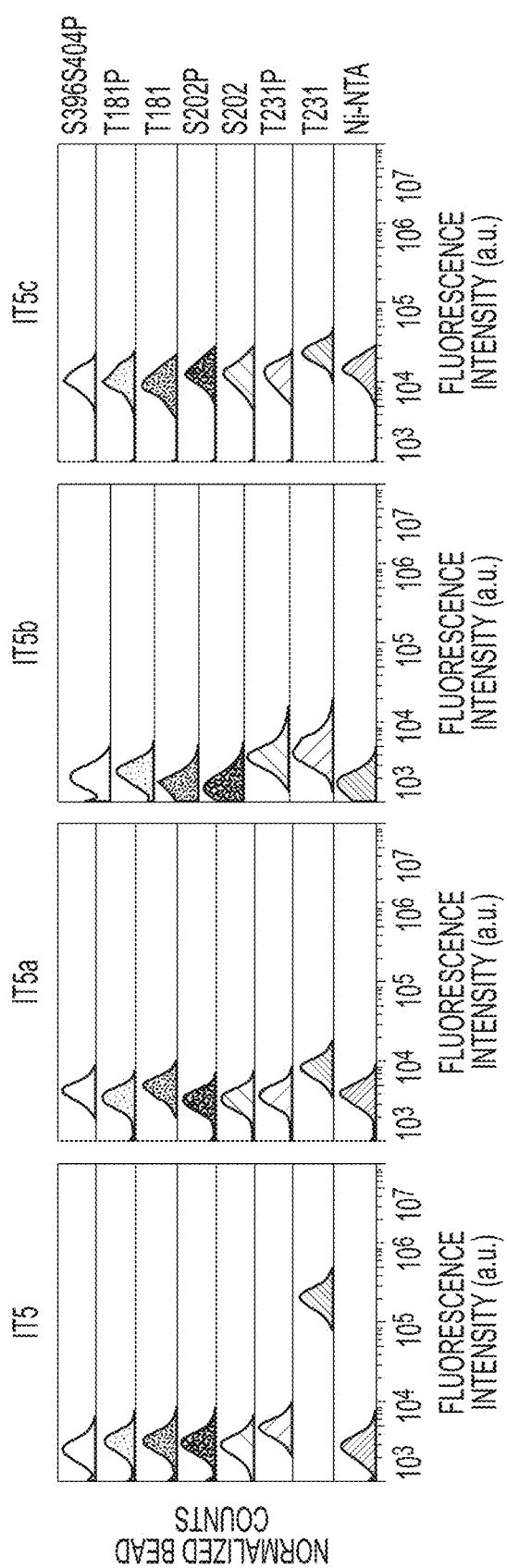

FIGS. 17A and 17B illustrate sequence optimization of IT5, according to an embodiment of the disclosed invention. (A) Predicted secondary structures of aptamer IT5 (SEQ ID NO: 5) and its truncated candidates, IT5a (SEQ ID NO: 51, which shows an additional nucleotide 5'-C compared to SEQ ID NO: 23), IT5b (SEQ ID NO: 24), and IT5c (SEQ ID NO: 52, which shows an additional nucleotide 5'-G and an additional nucleotide A-3' compared to SEQ ID NO: 25). (B) None of the truncated candidates for IT4 showed binding affinity to T231.

Figure 30:
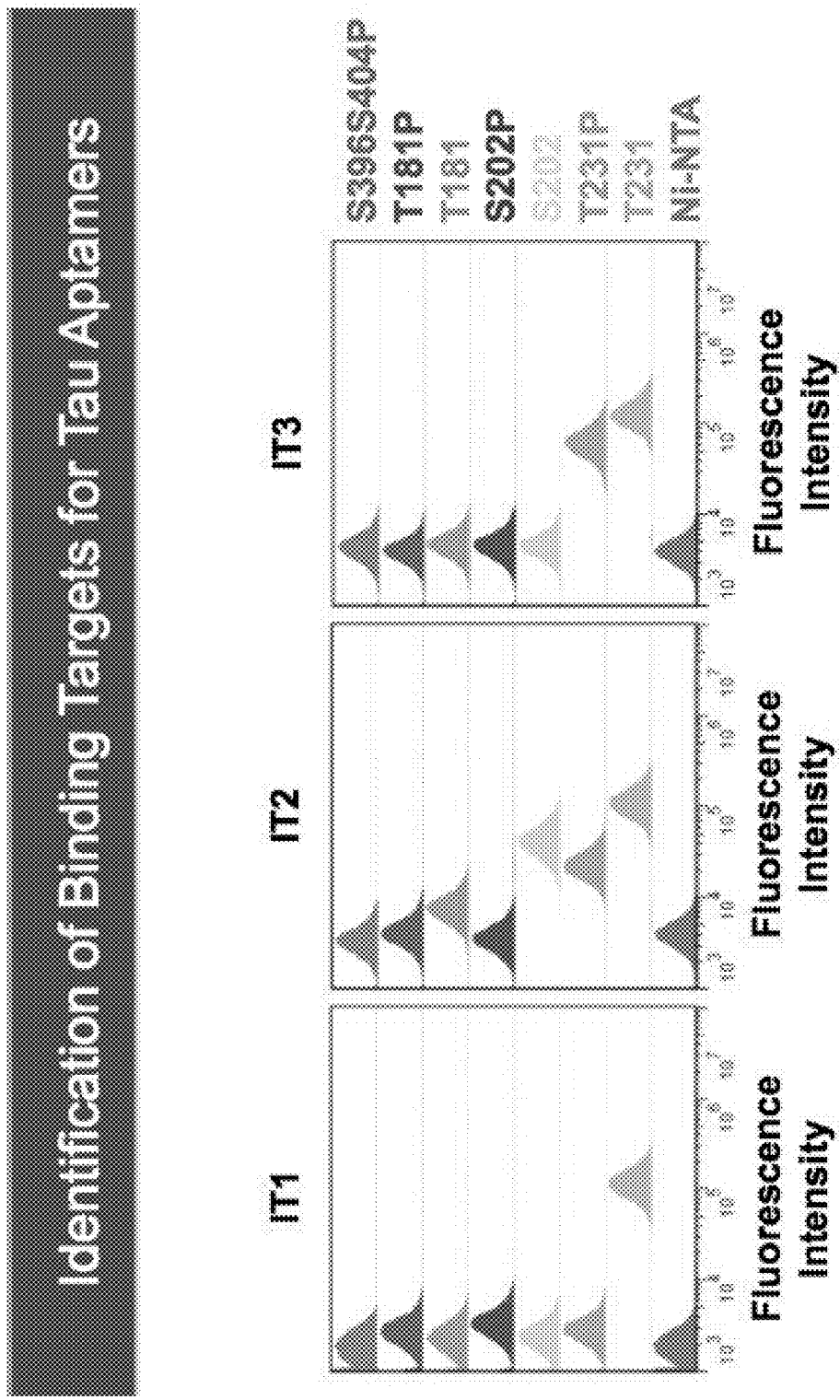
FIG. 30 is a table showing the identification of Tau epitope binding targets for three tau aptamers, according to an embodiment of the disclosed invention.

FIG. 30 is a table showing the identification of Tau epitope binding targets for three tau aptamers, according to an embodiment of the disclosed invention. A shift to the right indicates Tau aptamers (IT1, IT2 or IT3) binding to stated target epitopes of Tau (e.g. 53965404P, T181P, T181, 5202P, S202, T231P, T231 His-tag peptides. Ni-NTA is negative control without any peptide.

FIG. 31 is a table showing the sequence truncation of some tau aptamers, and their preferred binding to specific tau epitopes, according to an embodiment of the disclosed invention.

Figure 18A:
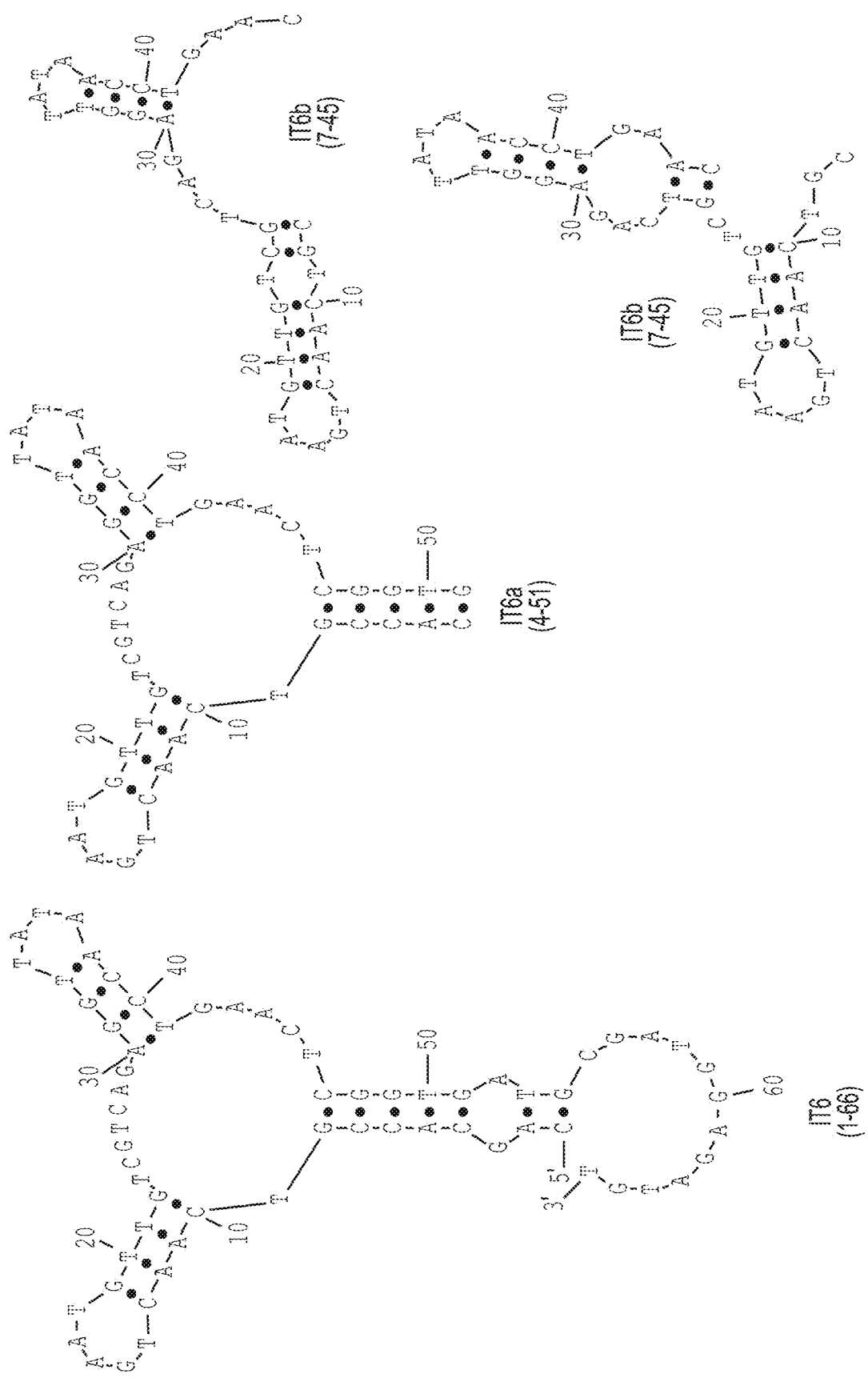
FIGS. 18A and 18B illustrate sequence optimization of IT6, according to an embodiment of the disclosed invention.
Figure 18B:
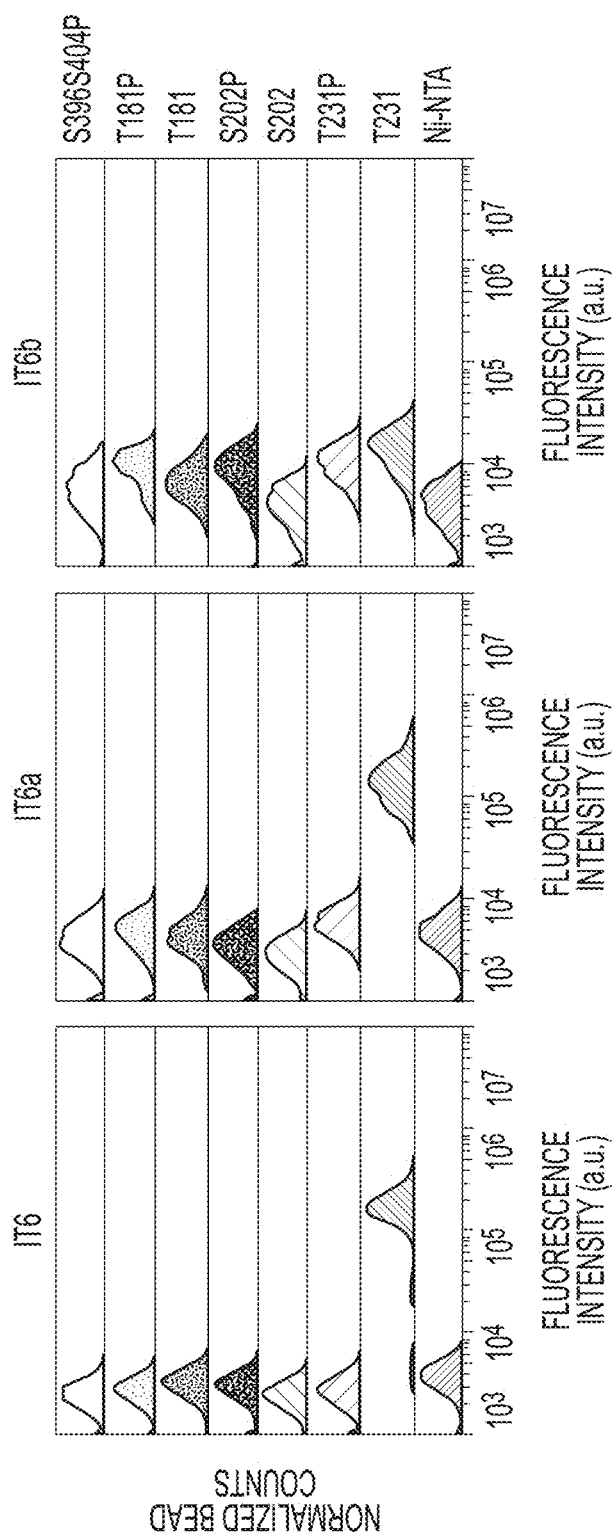
Figure 19A:
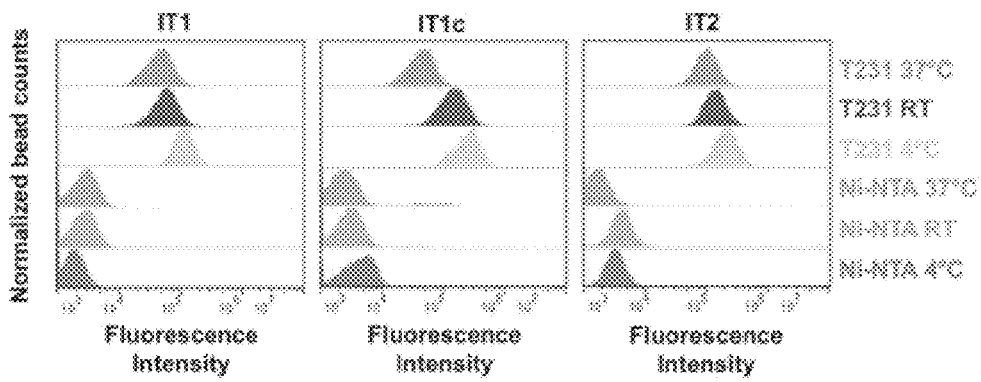
FIGS. 19A through 19D illustrate the binding abilities evaluated at room temperature and at 37° C. as compared to the binding strengths measured at 4° C., according to an embodiment of the disclosed invention.
Figure 19B:
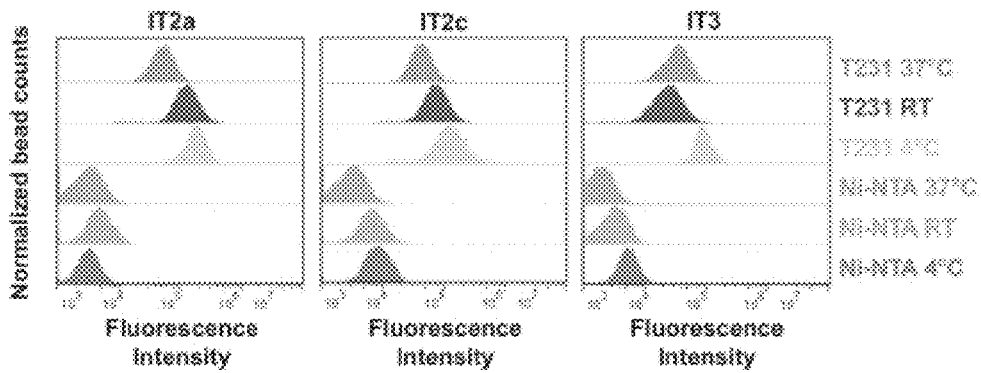
Figure 19C:
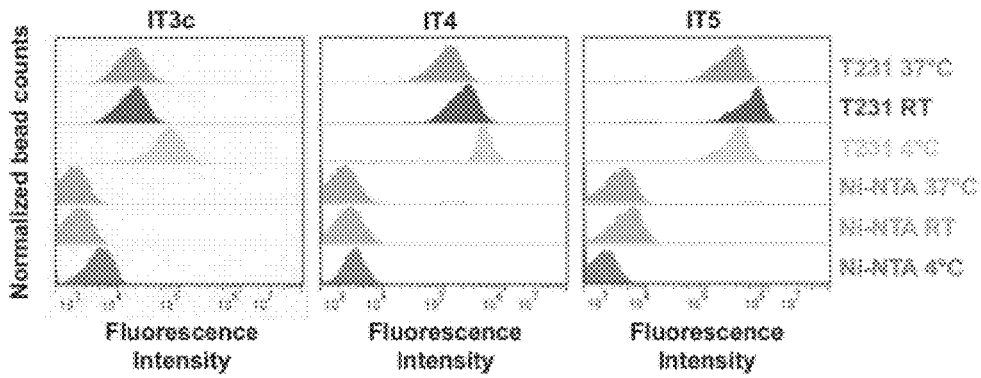
Figure 19D:
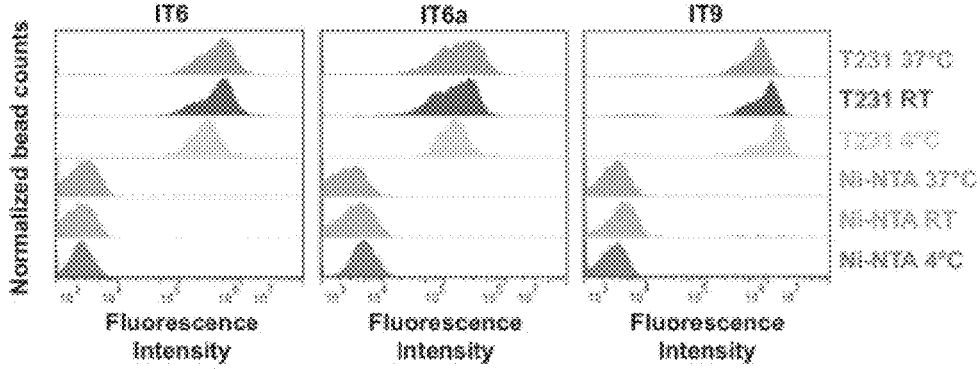

As for aptamer IT2 (SEQ ID NO: 2), an evident stem-loop motif was observed in its predicted secondary structure (FIG. 14A). Thus, IT2 was abbreviated into IT2a (SEQ ID NO: 12) with the neat hairpin structure, which then demonstrated similar binding profile to targets T231, T231P, and S202 as of IT2 (FIG. 14B). Yet, the much more stringent truncation of IT2a (IT2b (SEQ ID NO: 13)) failed to maintain the properties of the aptamer. A much gentle approach was then implemented to shorten aptamer IT2a (SEQ ID NO: 12). Sequence IT2c (SEQ ID NO: 14) still presented similar binding ability compared to IT2a. However, a gradual loss of binding ability was observed when further truncating the stem of IT2c, demonstrating the importance of a stable stem for binding of aptamer IT2c to its targets, especially for S202 peptide. The above results also corresponded to the loss of binding with sequence IT10, which resembled aptamer IT2 with one exception at position 19 (FIG. 12B, Table 5). It turned out that nucleotide #19 for IT2 was indeed within the binding motif. Considering the same effect found with IT3 and IT8, nucleotide #19 for aptamer IT3 should also play an important role for its binding ability. Also, taking the predicted secondary structures into consideration, optimization of aptamer IT3 then begun with eliminating the nucleotides at its 3'-end. Unfortunately, truncation of IT3 (SEQ ID NO: 3) caused complete loss or decrease of its binding to T231, except for IT3c (SEQ ID NO: 19), while the binding between IT3 and T231P was extremely susceptible to any attempts of sequence truncation made here (FIG. 15A and FIG. 15B). Likewise, the endeavors to shorten IT4 and IT5 were found unsuccessful (FIGS. 16A and 16B, and FIGS. 17A and 17B), demonstrating that the full-length sequences of IT3, IT4, and IT5 were required for these aptamers to function properly. Finally, the secondary structure prediction revealed that aptamer IT6 would form a branched hairpin structure. The sequence truncation yielded IT6a, which, unlike IT6b, retained the selective binding ability to T231 as shown in FIGS. 18A and 18B. FIGS. 18A and 18B illustrate sequence optimization of IT6, according to an embodiment of the disclosed invention. (A) Predicted secondary structures of aptamer IT6 (SEQ ID NO: 6) and its truncated candidates, IT6a (SEQ ID NO: 26) and IT6b (SEQ ID NO: 27). (B) Sequence IT6a demonstrated similar binding affinity to T231 as of aptamer IT6, but sequence IT6b failed to maintain the binding strength to T231.

Evaluation of Binding Abilities at Elevated Temperature

FIGS. 19A through 19D illustrate the binding abilities evaluated at room temperature and at 37° C. as compared to the binding strengths measured at 4° C., according to an embodiment of the disclosed invention. All of the aptamers were able to demonstrate similar binding abilities even when the temperature was increased to 37° C.

The above binding tests were carried out at 4° C. to ensure having the optimal secondary structures for aptamers. However, in order to validate the feasibility of utilizing the selected aptamers for biological studies that have to be done under physiological conditions, the binding abilities of the selected aptamers were also examined at room temperature and at 37° C., respectively. As shown in FIGS. 3A, 3B, 3C, 4, 5, 6A, 6B, 7A, 7B, 7D, 8, 9, 10, 11, 12A through 12J, 13A, 13B, 14A, 14B, 15A, 15B, 16A, 16B, 17A, and 17B, all of the selected aptamers possessed either similar or similar but slightly weaker binding strengths at 37° C. as compared to that at 4° C. None of the aptamers reported here completely lost its binding ability at room temperature or 37° C., demonstrating that these aptamers could be adopted to in vitro and in vivo studies. The summary of the Tau epitope binding of tau aptamers and the truncated aptamers is shown as FIG. 31, which is a table showing the sequence truncation of some tau aptamers, and their preferred binding to specific tau epitopes, according to an embodiment of the disclosed invention.

Determination of Binding Kinetics/Affinities of the Selected Aptamers

Direct measurement of binding kinetics plays an important role in understanding the interactions between aptamers and their targets. The kinetics also provides insightful information on binding affinities. For reversible, non-covalent binding occurred during biomolecular complex formation, the reaction typically comprises a continuum of association (forward reaction) and dissociation (reverse reaction). Generally, association rate constant describes how fast one molecule binds to another, while dissociation rate constant refers to how fast a complex falls apart. Finally, the binding affinity, which in a way determines how much complex is formed at equilibrium, is obtained by incorporating the ratio of these two rate constants. When applying a 1:1 bimolecular interaction model, the reaction of an aptamer binding to its target may be expressed as Equation 3-1. The rate equations for association and dissociation are shown as Equation 3-2 and Equation 3-3, respectively, where $k_{on}$ is the association rate constant and $k_{off}$ is the dissociation rate constant. Accordingly, the net rate equation for the overall reaction at any time point is given in Equation 3-4, which then transforms into Equation 3-5 at equilibrium. The affinity of an aptamer binding to its target is often evaluated by the equilibrium dissociation constant Kd, which is defined in Equation 3-6.

The reaction of an aptamer binding to its target.

$$\text{Aptamer} + \text{Target} \rightleftharpoons \text{Aptamer·Target} \quad (3\text{-}1)$$

The rate equation for association.

$$\frac{d[\text{Aptamer·Target}]}{dt} = k_{on}[\text{Aptamer}][\text{Target}] \quad (3\text{-}2)$$

The rate equation for dissociation.

$$\frac{-d[\text{Aptamer·Target}]}{dt} = k_{off}[\text{Aptamer·Target}] \quad (3\text{-}3)$$

The net rate equation for the overall binding reaction.

$$\frac{d[\text{Aptamer·Target}]}{dt} = k_{on}[\text{Aptamer}][\text{Target}] - k_{off}[\text{Aptamer·Target}] \quad (3\text{-}4)$$

The rate equation at equilibrium.

$$k_{on}[\text{Aptamer}][\text{Target}] = k_{off}[\text{Aptamer·Target}] \quad (3\text{-}5)$$

The dissociation constant Kd at equilibrium.

$$K_d = \frac{k_{off}}{k_{on}} = \frac{[\text{Aptamer}][\text{Target}]}{[\text{Aptamer·Target}]} \quad (3\text{-}6)$$

In the kinetic analysis carried out on Octet QKe, one interactant is immobilized on the surface of the biosensor (ligand) and the other remains in solution (analyte). A typical binding kinetics experiment begins with an initial baseline. Next, the loading step allows immobilization of ligand molecules onto the surface of the biosensors, after which the biosensors are dipped into buffer solution for establishing a baseline. The following steps involve dipping the biosensors into a solution containing the binding partner (association) and then transferring the biosensors into a solution without analyte (dissociation). The binding interaction of the analyte to the immobilized ligand is measured in real time as the change in the number of molecules bound to the biosensor causes a shift in the interference pattern reflected from sensor surfaces. In this study, his-tag Tau/P-Tau peptides (T231, T231P, S202) or his-tag Tau441 protein were used as the ligand, while aptamer candidates were the analytes. Specific corresponding equations explained below were applied to analyze the different sensorgram phases.

Figure 20:
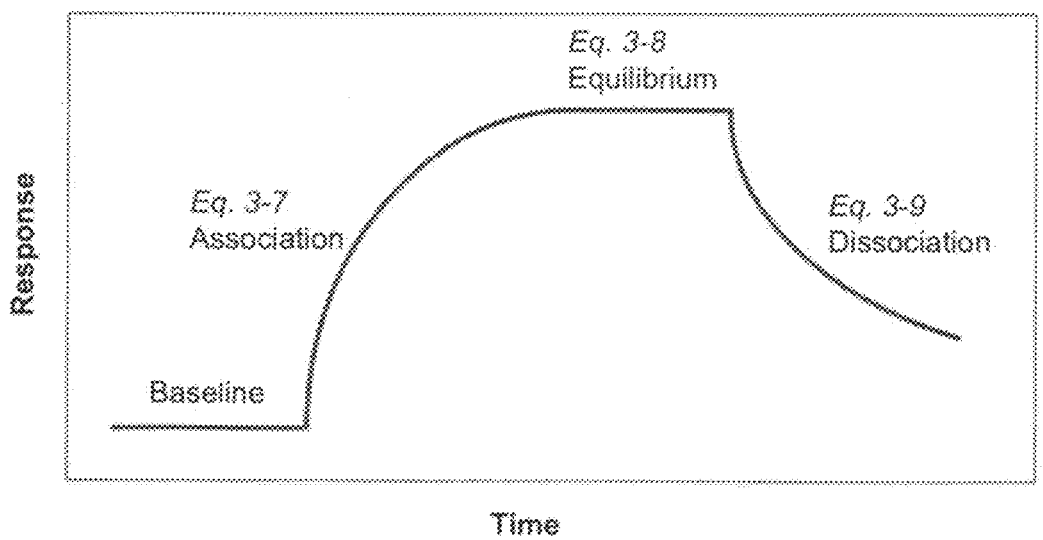
FIG. 20 illustrates a typical sensorgram displaying the association, equilibrium, and dissociation phases, according to an embodiment of the disclosed invention.
Figure 24A:
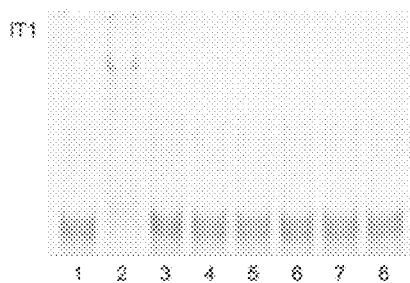
FIGS. 24A through 24G illustrate Gel electrophoresis of each tau aptamer and its binding complex with tau protein, according to an embodiment of the disclosed invention.
Figure 24B:
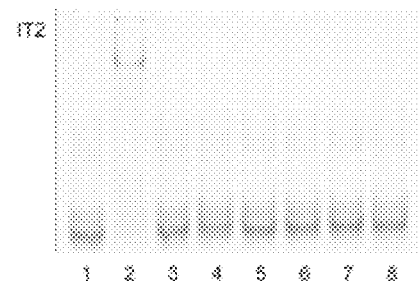
Figure 24C:
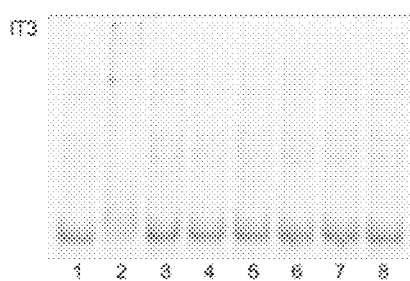
Figure 24D:
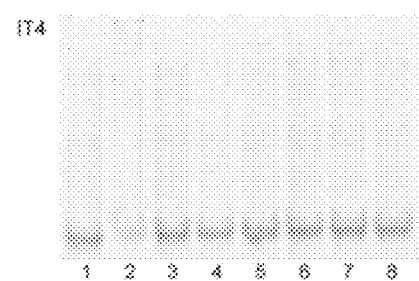
Figure 24E:
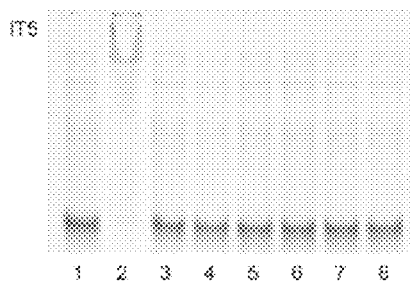
Figure 24F:
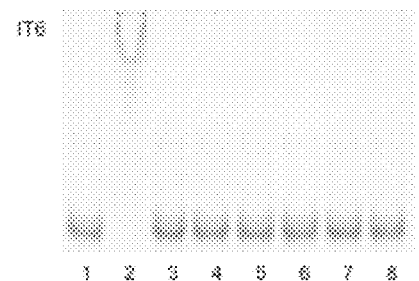
Figure 24G:
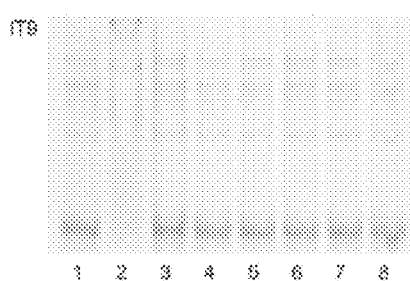

A typical sensorgram displays the association, equilibrium, and dissociation phases as shown in FIG. 20. At the early stage of the association phase, there is an increase in response units over time as the complex forms on the biosensor. Analysis of the sensorgram curve in the association phase using Equation 3-7 determines the rate of complex formation. The derivation of Equation 3-7 is shown in Figure FIG. 21. Equation 3-8 describes the response obtained at the steady state of the interaction. To determine the Kd using steady state analysis, the response at equilibrium, $R_{eq}$, is measured with a range of aptamer concentrations. At lower concentrations, the value of $R_{eq}$ increases as the concentration of aptamer rises, but eventually it reaches a plateau, the theoretical maximum response denoted by $R_{max}$. The derivation of Equation 3-8 is shown in FIG. 22. In the dissociation phase, the concentration of aptamer is brought to zero and the complex starts to fall apart in an exponential manner as shown in Equation 3-9, where $R_0$ is the signal level at the beginning of dissociation phase. The derivation of Equation 3-9 is shown in FIG. 23.

The equation for analyzing the association phase in sensorgrams.

The equation for analyzing the association phase in sensorgrams.

$$R_t = \frac{R_{max}[\text{Aptamer}]}{K_d + [\text{Aptamer}]}\left[1 - e^{-(k_{on}[\text{Aptamer}] + k_{off})t}\right] \quad (3\text{-}7)$$

The equation for analyzing the equilibrium phase in sensorgrams.

$$R_{eq} = \frac{R_{max}[\text{Aptamer}]}{K_d + [\text{Aptamer}]} \quad (3\text{-}8)$$

The equation for analyzing the dissociation phase in sensorgrams.

$$R_t = R_0 e^{-k_{off} t} \quad (3\text{-}9)$$

The kinetic on-rates (kon), off-rates (koff), as well as the equilibrium dissociation constants (Kd) measured for all aptamer-target pairs were summarized in Table 6. All of the aptamers reported here displayed high binding affinities toward Tau441 with the Kd values ranging from 5.5 nM to 68 nM. Except for IT4, all other aptamers have the equilibrium dissociation constants lower than 30 nM. The observed on-rates ranged between 104 M-1s-1 to nearly 106 M-1s-1. Aptamer IT1 presented the fastest on-rate ((9.3±1.9)×105 M-1s-1) toward Tau441 protein than any other aptamers or aptamer-target pairs, while the slowest on-rate ((1.067±0.018)×104 M-1s-1) was detected from IT2 against Tau441. However, IT2 also demonstrated an extremely slow off-rate ((5.9±1.2)×10-5 s-1) from Tau441, rendering the lowest Kd (5.5±1.1 nM) against Tau441 protein among all the aptamers. The lowest Kd toward peptides, on the other hand, was found between IT5 and T231 (5.0±0.3 nM). In the meanwhile, IT5 also exhibited the second lowest Kd (7.6±0.6 nM) against Tau441 protein among all the aptamers, indicating the high binding affinities of IT5 toward both T231 peptide and Tau441 protein. Although aptamer IT9 is only one base different from IT5 (as shown in Table 5), IT9 displayed appreciable slower on-rates and therefore higher equilibrium dissociation constants than IT5.

While IT1 showed similar binding kinetics toward T231 and Tau441, the shorter version of the aptamer IT1c exhibited a much slower off-rate from Tau441 protein than from T231 peptide even though IT1c in general showed slower on-rates and slower off-rates than IT1. On the other hand, truncation of IT2 did not affect the association of the aptamers with T231 peptide, but the shorter aptamer IT2a displayed a faster dissociation rate with T231 than IT2. In fact, the dissociation rates with any of the targets got increased with IT2a compared to the off-rates with IT2. In addition, with either IT2 or IT2a, a faster on-rate with T231P peptide was found in comparison to that of T231. With IT2a, especially, the on-rate toward T231P is almost 5 times faster than its on-rate toward T231 and this on-rate is also 2.5-fold faster than the association of IT2 toward T231P. However, the association of IT2a to S202 peptide showed an opposite tendency. The on-rate between IT2a and S202 was found more than 6 times slower than the on-rate between IT2 and S202. The above effects indicated that the truncation of IT2 was more beneficial to the recognition of T231P but deteriorated the binding affinity toward S202 site. Besides, though the association of IT2a against Tau441 was almost 50 times faster than IT2, its off-rate was also 60 times faster than IT2. Overall, the binding affinity of IT2a got weaken by the truncation. Unlike IT1c and IT2a, the shorter version of

TABLE 6

The kinetic on-rates ($k_{on}$), off-rates ($k_{off}$), and the equilibrium dissociation constants ($K_d$) for all aptamer-target pairs.

| Aptamer | Target | $k_{on}$ (M$^{-1}$s$^{-1}$) | $k_{off}$ (s$^{-1}$) | $K_d$ (nM) | R$^2$ |
|---|---|---|---|---|---|
| IT1 | T231 peptide | (6.5 ± 0.7) × 10$^5$ | (9.27 ± 0.17) × 10$^{-3}$ | 14 ± 2 | 0.98 |
| IT1 | Tau441 | (9.3 ± 1.9) × 10$^5$ | (8.8 ± 0.2) × 10$^{-3}$ | 9 ± 2 | 0.94 |
| IT1c | T231 peptide | (5.4 ± 0.5) × 10$^4$ | (2.48 ± 0.07) × 10$^{-3}$ | 46 ± 3 | 0.99 |
| IT1c | Tau441 | (5.7 ± 0.6) × 10$^4$ | (7.38 ± 0.13) × 10$^{-4}$ | 13.0 ± 1.4 | 0.96 |
| IT2 | T231 peptide | (1.05 ± 0.04) × 10$^5$ | (1.704 ± 0.013) × 10$^{-3}$ | 16.2 ± 0.6 | 0.93 |
| IT2 | T231P peptide | (1.68 ± 0.16) × 10$^5$ | (5.81 ± 0.09) × 10$^{-3}$ | 34 ± 3 | 0.88 |
| IT2 | S202 peptide | (2.22 ± 0.18) × 10$^5$ | (2.72 ± 0.03) × 10$^{-3}$ | 12.3 ± 1.0 | 0.86 |
| IT2 | Tau441 | (1.067 ± 0.018) × 10$^4$ | (5.9 ± 1.2) × 10$^{-5}$ | 5.5 ± 1.1 | 0.98 |
| IT2a | T231 peptide | (9.5 ± 0.5) × 10$^4$ | (7.52 ± 0.09) × 10$^{-3}$ | 79 ± 4 | 0.93 |
| IT2a | T231P peptide | (4.3 ± 0.9) × 10$^5$ | (3.00 ± 0.14) × 10$^{-2}$ | 70 ± 15 | 0.88 |
| IT2a | S202 peptide | (3.37 ± 0.10) × 10$^4$ | (9.15 ± 0.08) × 10$^{-3}$ | 272 ± 8 | 0.97 |
| IT2a | Tau441 | (5.0 ± 0.4) × 10$^5$ | (9.86 ± 0.16) × 10$^{-3}$ | 19.5 ± 1.7 | 0.97 |
| IT3 | T231 peptide | (4.82 ± 0.10) × 10$^4$ | (8.85 ± 0.06) × 10$^{-4}$ | 18.4 ± 0.4 | 0.89 |
| IT3 | T231P peptide | (5.17 ± 0.17) × 10$^4$ | (1.624 ± 0.015) × 10$^{-3}$ | 31.4 ± 1.1 | 0.95 |
| IT3 | Tau441 | (6.39 ± 0.17) × 10$^4$ | (1.09 ± 0.02) × 10$^{-3}$ | 17.0 ± 0.6 | 0.99 |
| IT4 | T231 peptide | (6.04 ± 0.16) × 10$^4$ | (1.974 ± 0.012) × 10$^{-3}$ | 32.7 ± 0.9 | 0.94 |
| IT4 | Tau441 | (2.95 ± 0.08) × 10$^4$ | (1.99 ± 0.04) × 10$^{-3}$ | 68 ± 2 | 0.99 |
| IT5 | T231 peptide | (3.14 ± 0.18) × 10$^5$ | (1.57 ± 0.04) × 10$^{-3}$ | 5.0 ± 0.3 | 0.96 |
| IT5 | Tau441 | (1.43 ± 0.08) × 10$^5$ | (1.09 ± 0.06) × 10$^{-3}$ | 7.6 ± 0.6 | 0.97 |
| IT6 | T231 peptide | (7.0 ± 0.9) × 10$^5$ | (1.120 ± 0.019) × 10$^{-2}$ | 16 ± 2 | 0.98 |
| IT6 | Tau441 | (4.95 ± 0.16) × 10$^4$ | (1.33 ± 0.03) × 10$^{-3}$ | 26.8 ± 1.1 | 0.99 |
| IT6a | T231 peptide | (5.3 ± 0.5) × 10$^5$ | (8.40 ± 0.12) × 10$^{-3}$ | 15.7 ± 1.4 | 0.99 |
| IT6a | Tau441 | (3.58 ± 0.07) × 10$^4$ | (1.009 ± 0.014) × 10$^{-3}$ | 28.2 ± 0.7 | 0.99 |
| IT9 | T231 peptide | (3.76 ± 0.06) × 10$^4$ | (6.88 ± 0.17) × 10$^{-4}$ | 18.3 ± 0.5 | 0.99 |
| IT9 | Tau441 | (4.78 ± 0.12) × 10$^4$ | (1.09 ± 0.03) × 10$^{-3}$ | 22.8 ± 0.9 | 0.99 |

IT6 did not affect the binding kinetics and affinity. IT6a still behaved quite the same as IT6.

Finally, as shown in Panel B of FIG. 15, aptamer IT3 recognized both T231 and T231P. The on-rates of IT3 to both peptides were found quite similar, but the off-rate with T231P was almost 2-fold faster than with T231. The difference on the dissociation rates corresponded to the distinct peak shifts seen in Panel B of FIG. 15.

Conclusion

Four phosphorylatable regions from tau protein and the corresponded phosphorylated peptide fragments from pathologic tau were used as targets to carry out the selection for site-specific tau aptamers. One of the aptamers (IT3) identified overlooked phosphorylation on T231 and recognized both T231 and T231P. Another one (IT2) could bind to T231, T231P, and S202, but not S202P. The rest of the aptamers discovered were highly specific to T231 site only. We were able to truncate three of the identified aptamers into shorter versions without appreciable compromise on their binding abilities to targets. All of the tau aptamers reported here showed high affinity to tau protein. The dissociation constants of these aptamers against Tau441 protein ranged from 5.5 nM to 68 nM.

Multiplex SELEX for More Phosphorylatable-Site-Specific Tau Aptamers

Here we demonstrated the selection of site-specific aptamers using peptide fragments as targets in the evolution process. These aptamers selected from peptides still recognize full-length tau protein and exhibit inhibitory effects on oligomerization and phosphorylation of tau. Since there are more than 40 phosphorylatable sites on tau protein, a more comprehensive SELEX involving more phosphorylatable sites should be imposed to fully exploit the performance of aptamers in fighting tauopathy.

Example 2

Inhibitory Effects of Tau Aptamers on Aggregation and Phosphorylation of Tau

This example demonstrates the specificity of these tau aptamers and their inhibitory effects on pathological features of tau with these selected tau aptamers.

Significance and Background

Neurofibrillary tangles (NFTs) are aggregates of hyperphosphorylated tau protein that are known as a hallmark of Alzheimer's disease as well as several other neurodegenerative diseases. The abnormally phosphorylated tau lesion causes death of neuron cells, resulting in irreversible and progressive neurodegeneration. Such phenomenon is termed tauopathy and is as yet incurable. Understanding the origin and mechanism of tauopathy is a key step to develop means to delay or even to fight against the progressive neurodegeneration.

Nucleic acid aptamers are a class of powerful ligands that interact with their targets through structural recognition. Development of aptamer-based molecular recognition tools has become a very promising aspect in terms of target detection and analysis. Besides target recognitions, some aptamers could also alter the original functions or behaviors of their targets after forming the binding complex. For example, several aptamers were found to up-regulate or down-regulate the biological pathways associated with the binding targets,141-145 thus expending the possibility of utilizing aptamers for mechanistic studies between biological elements and even for discovering means to delay or remedy a malfunction.

Consequently, here we studied the inhibitory effects of the site-specific tau aptamers on phosphorylation and oligomerization of tau.

Materials and Methods

Specificity of the Selected Tau Aptamers Against Tau441 Protein

Gel electrophoresis was carried out to confirm the binding specificity between the selected aptamers against full-length Tau441 protein. S100B, UCH-L1, α casein, β casein, BSA, IgG were used as non-target proteins for reference. A 10-μL mixture containing FITC-labeled aptamer at 200 nM and designated protein at 0.05 mg/mL was incubated at 4° C. for 30 min before it was loaded onto a 8% non-denaturing polyacrylamide gel. Electrophoresis was initially carried out at 70 V for 10 min after introduction of the samples and then the voltage was increased to 150 V for 45 min in 1×TBE buffer. Finally, gels were scanned using a Typhoon Imaging System (Amersham Biosciences).

Induced Aggregation of Tau441 and the Inhibitory Effect of Tau Aptamer on Tau441 Oligomerization Full-length Tau441 protein was purchased from rPeptide (Bogart, Ga.). To examine the inhibitory effect of tau aptamers on aggregation of tau, the oligomerization reaction was performed in the presence of either IT3 aptamer or random sequence. IT3 aptamer (5, 10, or 20 μM) or random sequence (20 μM) was pre-incubated with Tau441 (10 μM) for 1 h before the treatment with the aggregation inducer heparin (Santa Cruz Biotechnology, Dallas, Tex.) (2 mg/mL) for 8 h at 37° C. in the oligomerization buffer (20 mM Tris-HCl, pH 7.4, 1 mM EDTA, 100 mM NaCl, 1 mM DTT). The negative control contained only Tau441. The positive control for observing Tau oligomers was prepared with Tau441 and heparin without pre-treatment with aptamers. The reaction products were analyzed by reducing SDS-PAGE followed by immunoblotting with anti-tau antibody, DA9.

Delay of Tau Phosphorylation/Oligomerization by Tau Aptamer in Cellular Models

The cell model used to demonstrate the induced hyperphosphorylation/tau oligomerization and the upstream inhibition of phosphorylation was a human neuroblastoma cell line, SH-SY5Y. A phosphatase inhibitor, okadaic acid, was used to induce the hyperphosphorylation. In brief, cells were plated at a density of 2×105 cells per well onto a 24-well plate and incubated for 24 h before co-incubation with aptamers or random sequence (20 μM, 300 μL) in serum free DMEM at 37° C. for 4 h. Each of the well was then supplemented with okadaic acid (final concentration 250 nM) and left at 37° C. for 16 hours. Afterwards, the cells in each well were collected and lysed by 100 μL lysis buffer (1% Triton X-100, lx protease inhibitor, 1% phosphatase inhibitor, 1 mM DTT) at 4° C. for 1 h. Finally, the reaction solution was centrifuged at 15,000 rpm for 15 min to remove the cell debris. The lysate was then submitted to protein assay. The samples were diluted with assay buffer to normalize the protein concentration and heated at 95° C. for 3 min before loading onto gel for electrophoresis analysis. The electrophoresis was carried out at 200 V for 45 min. Proteins were then transferred from gel to PVDF membrane and stained with immunoblotting.

Results and Discussion

Specificity of the Selected Tau Aptamers Against Tau441 Protein

The binding specificity of the selected tau aptamers to full length Tau441 protein was confirmed by non-denaturing gel electrophoresis after incubating each FITC-labeled aptamer with target tau protein and the non-target proteins separately. FIGS. 24A through 24G illustrate Gel electrophoresis of each tau aptamer and its binding complex with tau protein, according to an embodiment of the disclosed invention.

S100B, UCH-L1, α casein, β casein, BSA, and IgG were used as non-target reference proteins to show the specificity of tau aptamers. As shown in FIGS. 24A through 24G, each of the tau aptamer reported here showed specific binding to Tau441 protein. The aptamers alone displayed one main band at the lower part of the gel (lane 1). Some of the sequences also presented subtle upper bands due to the dimeric or multimeric forms of the oligonucleotides. The band representing aptamers disappeared in the presence of the target Tau441 because the aptamers were bound to Tau441 and the binding complex migrated much slower than aptamers alone (lane2). No cross-reactivity was observed between the aptamers and the non-target proteins, including S100B (~11 kDa), UCH-L1 (~25 kDa), α casein (~23 kDa), β casein (~24 kDa), BSA (~66 kDa), and IgG (~150 kDa) (lane 3-8). In particular, S100B and UCH-L1 are important references because they are also brain-associated proteins. S100B (S100 calcium-binding protein B) is a protein of the S-100 protein family, a group of proteins that are involved in the regulation of cellular processes such as cell cycle progression and differentiation. S100 proteins are present in the cytoplasm and nucleus of a wide range of cells, but S100B is glial-specific and is mainly expressed by astrocytes. S100B is found to be a neurite extension factor as well as a growth factor in the brain.146-149 UCH-L1 (Ubiquitin carboxy-terminal hydrolase L1) is a deubiquitinating enzyme that is required for the maintenance of axonal integrity. It is extremely abundant in the brain, making up 1-5% of total neuronal protein.150 The binding specificity of the aptamers among different proteins was therefore demonstrated.

Induced Aggregation of Tau441 and the Inhibitory Effect of Tau Aptamers on Tau441 Oligomerization To examine the inhibitory effect of tau aptamer on formation of tau oligomers, heparin was used to induce tau oligomerization and aptamer IT3 was used to counteract the aggregation effect. In brief, tau protein was incubated with aptamer or random sequence for 1 h followed by treatment with heparin for 8 h to form tau oligomers. The reaction products were then analyzed by reducing SDS-PAGE and immunoblotting.

Figure 25:
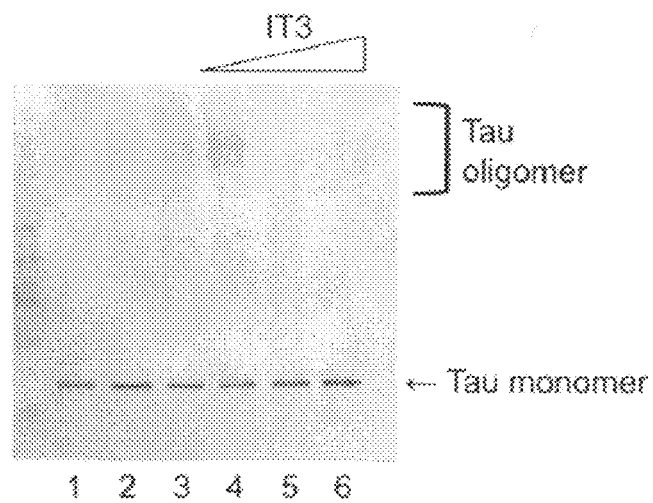
FIG. 25 illustrates immunoblotting image for examining formation of tau oligomers and the inhibition of tau aggregation by treatment with aptamers, according to an embodiment of the disclosed invention.

FIG. 25 illustrates immunoblotting image for examining formation of tau oligomers and the inhibition of tau aggregation by treatment with aptamers, according to an embodiment of the disclosed invention. As shown in FIG. 25 (lane 1), tau protein alone without any treatment showed a clear single band for monomers of tau. The heparin-mediated tau oligomerization products were seen as the smear in lane 2. When random sequence was preincubated with tau, the oligomeric assembly of tau induced by heparin was virtually unaffected even when the concentration of random sequence was 20 μM high (lane 3). In contrast, IT3 aptamer gradually reduced the amount of multimeric tau (lane 4-6), showing the inhibitory effect of the aptamer on formation of tau oligomer.

Figure 26:
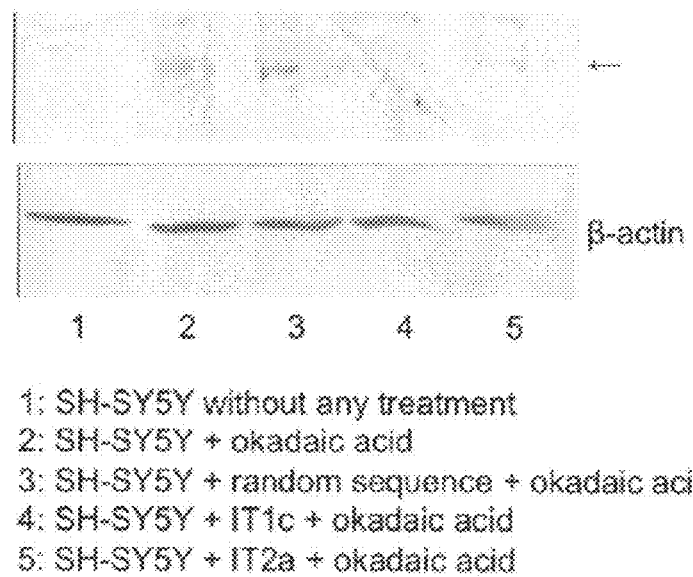
FIG. 26 illustrates immumoblotting image of tau oligomer and the housekeeping protein β-actin from SH-SY5Y cell lysate, according to an embodiment of the disclosed invention.

Inhibitory Effect of Tau Aptamers on Phosphorylation/Oligomerization in Living Cells To examine the function of tau aptamers in vitro, the phosphatase inhibitor (okadaic acid) was used to undermine the regulation between kinases and phosphatases and thus induce hyperphosphorylation of tau in living cells. FIG. 26 illustrates immunoblotting image of tau oligomer and the housekeeping protein β-actin from SH-SY5Y cell lysate, according to an embodiment of the disclosed invention. The arrow in FIG. 26 indicated the position of tau oligomers formed by phosphorylated tau. As shown in lane 1, no appreciable phosphor-tau oligomer was observed when there was no treatment. The treatment with okadaic acid indeed resulted in the oligomerization of tau, and the pre-treatment with random sequence contributed no apparent effect on oligomerization of tau. However, when the cells were pre-incubated with aptamer IT1c or aptamer IT2a, the reduction in oligomeric tau species was observed, proving that these two aptamer could function in living cells and bind with tau protein to prevent it from phosphorylation by kinases. β-actin was used as a protein loading control.

Conclusion

The tau aptamers tested in this example not only showed high affinity and specificity toward tau protein but also demonstrated effective inhibition on heparin-induced tau oligomerization and formation of phosphor-tau oligomers inside living cells. These results demonstrate the feasibility of using phosphorylatable sites specific tau aptamers to delay and confine the progression of tauopathy.

Having described the many embodiments of the disclosed invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

It is intended that the invention not be limited to the particular embodiment disclosed herein contemplated for carrying out this invention, but that the invention will include all embodiments falling within the scope of the claims.

REFERENCES

The following references are referred to above and are incorporated herein by reference:
1. Ellington, A. D.; Szostak, J. W., In vitro selection of RNA molecules that bind specific ligands. Nature 1990, 346 (6287), 818-22.
2. Tuerk, C.; Gold, L., Systematic evolution of ligands by exponential enrichment: RNA ligands to bacteriophage T4 DNA polymerase. Science 1990, 249 (4968), 505-10.
3. Wrzesinski, J.; Ciesiolka, J., Characterization of Structure and metal ions specificity of co2+-binding RNA aptamers. Biochemistry 2005, 44 (16), 6257-6268.
4. Catherine, A. T.; Shishido, S. N.; Robbins-Welty, G. A.; Diegelman-Parente, A., Rational design of a structure-switching DNA aptamer for potassium ions. FEBS Open Bio 2014, 4, 788-795.
5. Qu, H.; Csordas, A. T.; Wang, J.; Oh, S. S.; Eisenstein, M. S.; Soh, H. T., Rapid and label-free strategy to isolate aptamers for metal ions. ACS Nano 2016, 10 (8), 7558-7565.
6. Wilson, C.; Szostak, J. W., Isolation of a fluorophore-specific DNA aptamer with weak redox activity. Chemistry & Biology 1998, 5 (11), 609-617.
7. Famulok, M., Molecular Recognition of Amino Acids by RNA-Aptamers: An L-citrulline binding ma motif and its evolution into an L-Arginine binder. Journal of the American Chemical Society 1994, 116 (5), 1698-1706.
8. Majerfeld, I.; Yarus, M., Isoleucine:RNA sites with associated coding sequences. RNA 1998, 4 (4), 471-478.
9. Mannironi, C.; Scerch, C.; Fruscoloni, P.; Tocchini-Valentini, G. P., Molecular recognition of amino acids by RNA aptamers: the evolution into an L-tyrosine binder of a dopamine-binding RNA motif. RNA 2000, 6 (4), 520-527.

10. Lauhon, C. T.; Szostak, J. W., RNA aptamers that bind flavin and nicotinamide redox cofactors. Journal of the American Chemical Society 1995, 117 (4), 1246-1257.
11. Schürer, H.; Stembera, K.; Knoll, D.; Mayer, G.; Blind, M.; Förster, H.-H.; Famulok, M.; Welzel, P.; Hahn, U., Aptamers that bind to the antibiotic moenomycin A. Bioorganic & Medicinal Chemistry 2001, 9 (10), 2557-2563.
12. Niazi, J. H.; Lee, S. J.; Gu, M. B., Single-stranded DNA aptamers specific for antibiotics tetracyclines. Bioorganic & Medicinal Chemistry 2008, 16 (15), 7245-7253.
13. Stoltenburg, R.; Nikolaus, N.; Strehlitz, B., Capture-SELEX: selection of dna aptamers for aminoglycoside antibiotics. Journal of Analytical Methods in Chemistry 2012, 2012, 14.
14. Nikolaus, N.; Strehlitz, B., DNA-aptamers binding aminoglycoside antibiotics. sensors (Basel, Switzerland) 2014, 14 (2), 3737-3755.
15. Paige, J. S.; Duc, T. N.; Song, W.; Jaffrey, S. R., Fluorescence imaging of cellular metabolites with RNA. Science (New York, N.Y.) 2012, 335 (6073), 1194-1194.
16. Long, Y.; Pfeiffer, F.; Mayer, G.; Schroder, T. D.; Özalp, V. C.; Olsen, L. F., Selection of aptamers for metabolite sensing and construction of optical nanosensors. In Nucleic Acid Aptamers: Selection, Characterization, and Application, Mayer, G., Ed. Springer New York: New York, N.Y., 2016; pp 3-19.
17. Mendonsa, S. D.; Bowser, M. T., In vitro selection of aptamers with affinity for neuropeptide y using capillary electrophoresis. Journal of the American Chemical Society 2005, 127 (26), 9382-9383.
18. Ferreira, C. S. M.; Matthews, C. S.; Missailidis, S., DNA Aptamers That Bind to MUC1 Tumour Marker: Design and characterization of MUC1-binding single-stranded DNA aptamers. Tumor Biology 2006, 27 (6), 289-301.
19. Bock, L. C.; Griffin, L. C.; Latham, J. A.; Vermaas, E. H.; Toole, J. J., Selection of single-stranded DNA molecules that bind and inhibit human thrombin. Nature 1992, 355 (6360), 564-566.
20. Potty, A. S. R.; Kourentzi, K.; Fang, H.; Jackson, G. W.; Zhang, X.; Legge, G. B.; Willson, R. C., Biophysical characterization of DNA aptamer interactions with vascular endothelial growth factor. Biopolymers 2009, 91 (2), 145-156.
21. Kaur, H.; Yung, L.-Y. L., Probing high affinity sequences of DNA aptamer against VEGF165. PLOS ONE 2012, 7 (2), e31196.
22. Orava, E. W.; Jarvik, N.; Shek, Y. L.; Sidhu, S. S.; Gariépy, J., A short dna aptamer that recognizes TNFα and blocks its activity in vitro. ACS Chemical Biology 2013, 8 (1), 170-178.
23. Balogh, Z.; Lautner, G.; Bardóczy, V.; Komorowska, B.; Gyurcsányi, R. E.; Mészáros, T., Selection and versatile application of virus-specific aptamers. The FASEB Journal 2010, 24 (11), 4187-4195.
24. Wongphatcharachai, M.; Wang, P.; Enomoto, S.; Webby, R. J.; Gramer, M. R.; Amonsin, A.; Sreevatsan, S., Neutralizing DNA aptamers against swine influenza H3N2 viruses. Journal of Clinical Microbiology 2013, 51 (1), 46-54.
25. Tawaraya, Y.; Hyodo, M.; Ara, M. N.; Yamada, Y.; Harashima, H., RNA aptamers for targeting mitochondria using a mitochondria-based selex method. Biological and Pharmaceutical Bulletin 2014, 37 (8), 1411-1415.
26. Shangguan, D.; Li, Y.; Tang, Z.; Cao, Z. C.; Chen, H. W.; Mallikaratchy, P.; Sefah, K.; Yang, C. J.; Tan, W., Aptamers evolved from live cells as effective molecular probes for cancer study. Proceedings of the National Academy of Sciences 2006, 103 (32), 11838-11843.
27. Tang, Z.; Shangguan, D.; Wang, K.; Shi, H.; Sefah, K.; Mallikratchy, P.; Chen, H. W.; Li, Y.; Tan, W., Selection of aptamers for molecular recognition and characterization of cancer cells. Analytical Chemistry 2007, 79 (13), 4900-4907.
28. Conrad, R.; Keranen, L. M.; Ellington, A. D.; Newton, A. C., Isozyme-specific inhibition of protein kinase C by RNA aptamers. J Biol Chem 1994, 269 (51), 32051-4.
29. Chen, L.; Rashid, F.; Shah, A.; Awan, H. M.; Wu, M.; Liu, A.; Wang, J.; Zhu, T.; Luo, Z.; Shan, G., The isolation of an RNA aptamer targeting to p53 protein with single amino acid mutation. Proceedings of the National Academy of Sciences 2015, 112 (32), 10002-10007.
30. Geiger, A.; Burgstaller, P.; von der Eltz, H.; Roeder, A.; Famulok, M., RNA aptamers that bind L-arginine with sub-micromolar dissociation constants and high enantioselectivity. Nucleic Acids Research 1996, 24 (6), 1029-1036.
31. Shoji, A.; Kuwahara, M.; Ozaki, H.; Sawai, H., Modified DNA aptamer that binds the (R)-isomer of a thalidomide derivative with high enantioselectivity. J Am Chem Soc 2007, 129 (5), 1456-64.
32. Hu, K.; Liu, J.; Chen, J.; Huang, Y.; Zhao, S.; Tian, J.; Zhang, G., An amplified graphene oxide-based fluorescence aptasensor based on target-triggered aptamer hairpin switch and strand-displacement polymerization recycling for bioassays. Biosens Bioelectron 2013, 42, 598-602.
33. Xiao, S. J.; Hu, P. P.; Chen, L. Q.; Zhen, S. J.; Peng, L.; Li, Y. F.; Huang, C. Z., A visual dual-aptamer logic gate for sensitive discrimination of prion diseases-associated isoform with reusable magnetic microparticles and fluorescence quantum dots. PLOS ONE 2013, 8 (2), e53935.
34. Mairal, T.; Nadal, P.; Svobodova, M.; O'Sullivan, C. K., FRET-based dimeric aptamer probe for selective and sensitive Lup an 1 allergen detection. Biosens Bioelectron 2014, 54, 207-10.
35. Cho, S.; Lee, S. H.; Chung, W. J.; Kim, Y. K.; Lee, Y. S.; Kim, B. G., Microbead-based affinity chromatography chip using RNA aptamer modified with photocleavable linker. Electrophoresis 2004, 25 (21-22), 3730-9.
36. Balamurugan, S.; Obubuafo, A.; McCarley, R. L.; Soper, S. A.; Spivak, D. A., Effect of linker structure on surface density of aptamer monolayers and their corresponding protein binding efficiency. Anal Chem 2008, 80 (24), 9630-4.
37. Huang, Y. F.; Shangguan, D.; Liu, H.; Phillips, J. A.; Zhang, X.; Chen, Y.; Tan, W., Molecular assembly of an aptamer-drug conjugate for targeted drug delivery to tumor cells. Chembiochem 2009, 10 (5), 862-8.
38. Donovan, M. J.; Meng, L.; Chen, T.; Zhang, Y.; Sefah, K.; Tan, W., Aptamer-drug conjugation for targeted tumor cell therapy. Methods Mol Biol 2011, 764, 141-52.
39. Li, X.; Zhao, Q.; Qiu, L., Smart ligand: aptamer-mediated targeted delivery of chemotherapeutic drugs and siRNA for cancer therapy. J Control Release 2013, 171 (2), 152-62.
40. Medley, C. D.; Bamrungsap, S.; Tan, W.; Smith, J. E., Aptamer-conjugated nanoparticles for cancer cell detection. Anal Chem 2011, 83 (3), 727-34.
41. Wang, R. E.; Wu, H.; Niu, Y.; Cai, J., Improving the stability of aptamers by chemical modification. Curr Med Chem 2011, 18 (27), 4126-38.
42. Shigdar, S.; Macdonald, J.; O'Connor, M.; Wang, T.; Xiang, D.; Al Shamaileh, H.; Qiao, L.; Wei, M.; Zhou, S.

F.; Zhu, Y.; Kong, L.; Bhattacharya, S.; Li, C.; Duan, W., Aptamers as theranostic agents: modifications, serum stability and functionalisation. Sensors (Basel) 2013, 13 (10), 13624-37.

43. Hudson, W. H.; Ortlund, E. A., The structure, function and evolution of proteins that bind DNA and RNA. Nature reviews. Molecular cell biology 2014, 15 (11), 749-760.

44. Gelinas, A. D.; Davies, D. R.; Janjic, N., Embracing proteins: structural themes in aptamer-protein complexes. Current Opinion in Structural Biology 2016, 36, 122-132.

45. Griffin, L. C.; Tidmarsh, G. F.; Bock, L. C.; Toole, J. J.; Leung, L. L., In vivo anticoagulant properties of a novel nucleotide-based thrombin inhibitor and demonstration of regional anticoagulation in extracorporeal circuits. Blood 1993, 81 (12), 3271.

46. Macaya, R. F.; Schultze, P.; Smith, F. W.; Roe, J. A.; Feigon, J., Thrombin-binding DNA aptamer forms a unimolecular quadruplex structure in solution. Proceedings of the National Academy of Sciences 1993, 90 (8), 3745-3749.

47. Padmanabhan, K.; Padmanabhan, K. P.; Ferrara, J. D.; Sadler, J. E.; Tulinsky, A., The structure of alpha-thrombin inhibited by a 15-mer single-stranded DNA aptamer. Journal of Biological Chemistry 1993, 268 (24), 17651-17654.

48. Anand, P.; Kunnumakara, A. B.; Sundaram, C.; Harikumar, K. B.; Tharakan, S. T.; Lai, O. S.; Sung, B.; Aggarwal, B. B., Cancer is a preventable disease that requires major lifestyle changes. Pharmaceutical Research 2008, 25 (9), 2097-2116.

49. Cancer facts & figures 2017. American Cancer Society: 2017.

50. Torre, L. A.; Bray, F.; Siegel, R. L.; Ferlay, J.; Lortet-Tieulent, J.; Jemal, A., Global cancer statistics, 2012. CA: A Cancer Journal for Clinicians 2015, 65 (2), 87-108.

51. Siegel, R.; Naishadham, D.; Jemal, A., Cancer statistics, 2013. CA: A Cancer Journal for Clinicians 2013, 63 (1), 11-30.

52. Siegel, R. L.; Miller, K. D.; Jemal, A., Cancer statistics, 2017. CA: A Cancer Journal for Clinicians 2017, 67 (1), 7-30.

53. Sobin, L. H., TNM: Evolution and relation to other prognostic factors. Seminars in Surgical Oncology 2003, 21 (1), 3-7.

54. Blows, F. M.; Driver, K. E.; Schmidt, M. K.; Broeks, A.; van Leeuwen, F. E.; Wesseling, J.; Cheang, M. C.; Gelmon, K.; Nielsen, T. O.; Blomqvist, C.; Heikkilä, P.; Heikkinen, T.; Nevanlinna, H.; Akslen, L. A.; Bégin, L. R.; Foulkes, W. D.; Couch, F. J.; Wang, X.; Cafourek, V.; Olson, J. E.; Baglietto, L.; Giles, G. G.; Severi, G.; McLean, C. A.; Southey, M. C.; Rakha, E.; Green, A. R.; Ellis, I. O.; Sherman, M. E.; Lissowska, J.; Anderson, W. F.; Cox, A.; Cross, S. S.; Reed, M. W. R.; Provenzano, E.; Dawson, S.-J.; Dunning, A. M.; Humphreys, M.; Easton, D. F.; García-Closas, M.; Caldas, C.; Pharoah, P. D.; Huntsman, D., Subtyping of breast cancer by immunohistochemistry to investigate a relationship between subtype and short and long term survival: a collaborative analysis of data for 10,159 cases from 12 studies. PLOS Medicine 2010, 7 (5), e1000279.

55. Comprehensive molecular portraits of human breast tumours. Nature 2012, 490 (7418), 61-70.

56. Reimand, J.; Wagih, O.; Bader, G. D., The mutational landscape of phosphorylation signaling in cancer. Scientific Reports 2013, 3, 2651.

57. Narayan, S.; Bader, G. D.; Reimand, J., Frequent mutations in acetylation and ubiquitination sites suggest novel driver mechanisms of cancer. Genome Medicine 2016, 8 (1), 55.

58. Sager, R., Expression genetics in cancer: Shifting the focus from DNA to RNA. Proceedings of the National Academy of Sciences of the United States of America 1997, 94 (3), 952-955.

59. Hammarstrom, S., The carcinoembryonic antigen (CEA) family: structures, suggested functions and expression in normal and malignant tissues. Seminars in Cancer Biology 1999, 9 (2), 67-81.

60. Christensson, A.; Björk, T.; Nilsson, O.; Dahlén, U.; Matikainen, M. T.; Cockett, A. T.; Abrahamsson, P. A.; Lilja, H., Serum prostate specific antigen complexed to alpha 1-antichymotrypsin as an indicator of prostate cancer. The Journal of urology 1993, 150 (1), 100-105.

61. Normanno, N.; De Luca, A.; Bianco, C.; Strizzi, L.; Mancino, M.; Maiello, M. R.; Carotenuto, A.; De Feo, G.; Caponigro, F.; Salomon, D. S., Epidermal growth factor receptor (EGFR) signaling in cancer. Gene 2006, 366 (1), 2-16.

62. Itakura, J.; Ishiwata, T.; Friess, H.; Fujii, H.; Matsumoto, Y.; Büchler, M. W.; Korc, M., Enhanced expression of vascular endothelial growth factor in human pancreatic cancer correlates with local disease progression. Clinical Cancer Research 1997, 3 (8), 1309.

63. Heldin, C.-H., Targeting the PDGF signaling pathway in tumor treatment. Cell Communication and Signaling 2013, 11 (1), 97.

64. Chan, J. M.; Stampfer, M. J.; Giovannucci, E.; Gann, P. H.; Ma, J.; Wilkinson, P.; Hennekens, C. H.; Pollak, M., Plasma insulin-like growth factor-I and prostate cancer risk: a prospective study. Science 1998, 279 (5350), 563.

65. Ludwig, J. A.; Weinstein, J. N., Biomarkers in cancer staging, prognosis and treatment selection. Nat Rev Cancer 2005, 5 (11), 845-856.

66. Weingarten, M. D.; Lockwood, A. H.; Hwo, S. Y.; Kirschner, M. W., A protein factor essential for microtubule assembly. Proceedings of the National Academy of Sciences of the United States of America 1975, 72 (5), 1858-1862.

67. Mandelkow, E. M.; Biernat, J.; Drewes, G.; Gustke, N.; Trinczek, B.; Mandelkow, E., Tau domains, phosphorylation, and interactions with microtubules. Neurobiology of Aging 1995, 16 (3), 355-362.

68. Avila, J.; Lucas, J. J.; PÉRez, M. A. R.; HernÁNdez, F., Role of Tau Protein in Both Physiological and Pathological Conditions. Physiological Reviews 2004, 84 (2), 361.

69. Sergeant, N.; Delacourte, A.; Buée, L., Tau protein as a differential biomarker of tauopathies. Biochimica et Biophysica Acta (BBA)—Molecular Basis of Disease 2005, 1739 (2-3), 179-197.

70. Hernández, F.; Avila, J., Tauopathies. Cellular and Molecular Life Sciences 2007, 64 (17), 2219-2233.

71. Mandelkow, E., Alzheimer's disease: The tangled tale of tau. Nature 1999, 402 (6762), 588-589.

72. Hatakeyama, S.; Matsumoto, M.; Kamura, T.; Murayama, M.; Chui, D.-H.; Planel, E.; Takahashi, R.; Nakayama, K. I.; Takashima, A., U-box protein carboxyl terminus of Hsc70-interacting protein (CHIP) mediates poly-ubiquitylation preferentially on four-repeat Tau and is involved in neurodegeneration of tauopathy. Journal of Neurochemistry 2004, 91 (2), 299-307.

73. Richter-Landsberg, C.; Bauer, N. G., Tau-inclusion body formation in oligodendroglia: the role of stress proteins and proteasome inhibition. International Journal of Developmental Neuroscience 2004, 22 (7), 443-451.
74. Schraen-Maschke, S.; Sergeant, N.; Dhaenens, C.-M.; Bombois, S.; Deramecourt, V.; Caillet-Boudin, M.-L.; Pasquier, F.; Maurage, C.-A.; Sablonniere, B.; Vanmechelen, E.; Buee, L., Tau as a biomarker of neurodegenerative diseases. Biomarkers in Medicine 2008, 2 (4), 363-384.
75. McKee, A. C.; Stein, T. D.; Nowinski, C. J.; Stern, R. A.; Daneshvar, D. H.; Alvarez, V. E.; Lee, H.-S.; Hall, G.; Wojtowicz, S. M.; Baugh, C. M.; Riley, D. O.; Kubilus, C. A.; Cormier, K. A.; Jacobs, M. A.; Martin, B. R.; Abraham, C. R.; Ikezu, T.; Reichard, R. R.; Wolozin, B. L.; Budson, A. E.; Goldstein, L. E.; Kowall, N. W.; Cantu, R. C., The spectrum of disease in chronic traumatic encephalopathy. Brain 2013, 136 (1), 43-64.
76. Cleveland, D. W.; Hwo, S.-Y.; Kirschner, M. W., Purification of tau, a microtubule-associated protein that induces assembly of microtubules from purified tubulin. Journal of Molecular Biology 1977, 116 (2), 207-225.
77. Goedert, M.; Wischik, C. M.; Crowther, R. A.; Walker, J. E.; Klug, A., Cloning and sequencing of the cDNA encoding a core protein of the paired helical filament of Alzheimer disease: identification as the microtubule-associated protein tau. Proceedings of the National Academy of Sciences of the United States of America 1988, 85 (11), 4051-4055.
78. Goedert, M.; Spillantini, M. G.; Jakes, R.; Rutherford, D.; Crowther, R. A., Multiple isoforms of human microtubule-associated protein tau: sequences and localization in neurofibrillary tangles of Alzheimer's disease. Neuron 1989, 3 (4), 519-526.
79. Goedert, M.; Jakes, R., Expression of separate isoforms of human tau protein: correlation with the tau pattern in brain and effects on tubulin polymerization. The EMBO Journal 1990, 9 (13), 4225-4230.
80. Hutton, M.; Lendon, C. L.; Rizzu, P.; Baker, M.; Froelich, S.; Houlden, H.; Pickering-Brown, S.; Chakraverty, S.; Isaacs, A.; Grover, A.; Hackett, J.; Adamson, J.; Lincoln, S.; Dickson, D.; Davies, P.; Petersen, R. C.; Stevens, M.; de Graaff, E.; Wauters, E.; van Baren, J.; Hillebrand, M.; Joosse, M.; Kwon, J. M.; Nowotny, P.; Che, L. K.; Norton, J.; Morris, J. C.; Reed, L. A.; Trojanowski, J.; Basun, H.; Lannfelt, L.; Neystat, M.; Fahn, S.; Dark, F.; Tannenberg, T.; Dodd, P. R.; Hayward, N.; Kwok, J. B. J.; Schofield, P. R.; Andreadis, A.; Snowden, J.; Craufurd, D.; Neary, D.; Owen, F.; Oostra, B. A.; Hardy, J.; Goate, A.; van Swieten, J.; Mann, D.; Lynch, T.; Heutink, P., Association of missense and 5[prime]-splice-site mutations in tau with the inherited dementia FTDP-17. Nature 1998, 393 (6686), 702-705.
81. Schraen-Maschke, S.; Dhaenens, C.-M.; Delacourte, A.; Sablonniére, B., Microtubule-associated protein tau gene: a risk factor in human neurodegenerative diseases. Neurobiology of Disease 2004, 15 (3), 449-460.
82. D'Souza, I.; Schellenberg, G. D., Regulation of tau isoform expression and dementia. Biochimica et Biophysica Acta (BBA)—Molecular Basis of Disease 2005, 1739 (2-3), 104-115.
83. Goedert, M., Tau gene mutations and their effects. Movement Disorders 2005, 20 (S12), S45-S52.
84. Wang, Y.; Mandelkow, E., Tau in physiology and pathology. Nat Rev Neurosci 2016, 17 (1), 22-35.
85. Kim, S.; Wark, A. W.; Lee, H. J., Femtomolar detection of tau proteins in undiluted plasma using surface plasmon resonance. Analytical Chemistry 2016, 88 (15), 7793-7799.
86. Anderton, B. H., Expression and processing of pathologic proteins in alzheimer's disease. Hippocampus 1993, 3 (S1), 227-237.
87. Selkoe, D. J., Alzheimer's disease: genes, proteins, and therapy. Physiological Reviews 2001, 81 (2), 741.
88. Vinters, H. V., Cerebral amyloid angiopathy. A critical review. Stroke 1987, 18 (2), 311.
89. Ellis, R. J.; Olichney, J. M.; Thal, L. J.; Mirra, S. S.; Morris, J. C.; Beekly, D.; Heyman, A., Cerebral amyloid angiopathy in the brains of patients with Alzheimer's disease: The CERAD experience, part XV. Neurology 1996, 46 (6), 1592-1596.
90. Biffi, A.; Greenberg, S. M., Cerebral amyloid angiopathy: a systematic review. Journal of Clinical Neurology (Seoul, Korea) 2011, 7 (1), 1-9.
91. Brunden, K. R.; Trojanowski, J. Q.; Lee, V. M. Y., Advances in tau-focused drug discovery for Alzheimer's disease and related tauopathies. Nat Rev Drug Discov 2009, 8 (10), 783-793.
92. Sigurdsson, E. M., Tau-focused immunotherapy for Alzheimer's disease and related tauopathies. Current Alzheimer research 2009, 6 (5), 446-450.
93. Pedersen, J. T.; Sigurdsson, E. M., Tau immunotherapy for Alzheimer's disease. Trends in Molecular Medicine 2015, 21 (6), 394-402.
94. Stein, T. D.; Alvarez, V. E.; McKee, A. C., Chronic traumatic encephalopathy: a spectrum of neuropathological changes following repetitive brain trauma in athletes and military personnel. Alzheimer's Research & Therapy 2014, 6 (1), 4.
95. Hanger, D. P.; Anderton, B. H.; Noble, W., Tau phosphorylation: the therapeutic challenge for neurodegenerative disease. Trends in Molecular Medicine 2009, 15 (3), 112-119. Vulliet, R.; Halloran, S. M.; Braun, R. K.; Smith, A. J.; Lee, G., Proline-directed phosphorylation of human Tau protein. Journal of Biological Chemistry 1992, 267 (31), 22570-22574.
96. Biernat, J.; Gustke, N.; Drewes, G.; Mandelkow, E., Phosphorylation of Ser262 strongly reduces binding of tau to microtubules: Distinction between PHF-like immunoreactivity and microtubule binding. Neuron 1993, 11 (1), 153-163.
97. Cho, J.-H.; Johnson, G. V. W., Primed phosphorylation of tau at Thr231 by glycogen synthase kinase 3β(GSK3β) plays a critical role in regulating tau's ability to bind and stabilize microtubules. Journal of Neurochemistry 2004, 88 (2), 349-358.
98. Verslype, C.; Rosmorduc, O.; Rougier, P.; Group, E. G. W., Hepatocellular carcinoma: ESMO-ESDO clinical practice guidelines for diagnosis, treatment and follow-up. Ann Oncol 2012, 23 Suppl 7, vii41-8.
99. Shangguan, D.; Cao, Z.; Meng, L.; Mallikaratchy, P.; Sefah, K.; Wang, H.; Li, Y.; Tan, W., Cell-specific aptamer probes for membrane protein elucidation in cancer cells. J Proteome Res 2008, 7 (5), 2133-9.
100. Chang, Y. M.; Donovan, M. J.; Tan, W., Using aptamers for cancer biomarker discovery. J Nucleic Acids 2013, 2013, 817350.
101. Morris, K. N.; Jensen, K. B.; Julin, C. M.; Weil, M.; Gold, L., High affinity ligands from in vitro selection: complex targets. Proc Natl Acad Sci USA 1998, 95 (6), 2902-7.
102. Sefah, K.; Tang, Z. W.; Shangguan, D. H.; Chen, H.; Lopez-Colon, D.; Li, Y.; Parekh, P.; Martin, J.; Meng, L.; Phillips, J. A.; Kim, Y. M.; Tan, W. H., Molecular recognition of acute myeloid leukemia using aptamers. Leukemia 2009, 23 (2), 235-44.

103. Sefah, K.; Meng, L.; Lopez-Colon, D.; Jimenez, E.; Liu, C.; Tan, W., DNA aptamers as molecular probes for colorectal cancer study. PLoS One 2010, 5 (12), e14269.
104. Zhang, K.; Sefah, K.; Tang, L.; Zhao, Z.; Zhu, G.; Ye, M.; Sun, W.; Goodison, S.; Tan, W., A novel aptamer developed for breast cancer cell internalization. ChemMedChem 2012, 7 (1), 79-84.
105. Van Simaeys, D.; López-Colón, D.; Sefah, K.; Sutphen, R.; Jimenez, E.; Tan, W., Study of the molecular recognition of aptamers selected through ovarian cancer cell-SELEX. PLoS One 2010, 5 (11), e13770.
106. Chen, H. W.; Medley, C. D.; Sefah, K.; Shangguan, D.; Tang, Z.; Meng, L.; Smith, J. E.; Tan, W., Molecular recognition of small-cell lung cancer cells using aptamers. ChemMedChem 2008, 3 (6), 991-1001.
107. Zhao, Z.; Xu, L.; Shi, X.; Tan, W.; Fang, X.; Shangguan, D., Recognition of subtype non-small cell lung cancer by DNA aptamers selected from living cells. Analyst 2009, 134 (9), 1808-14.
108. Jiménez, E.; Sefah, K.; López-Colón, D.; Van Simaeys, D.; Chen, H. W.; Tockman, M. S.; Tan, W., Generation of lung adenocarcinoma DNA aptamers for cancer studies. PLoS One 2012, 7 (10), e46222.
109. Dua, P.; Kang, H. S.; Hong, S.-M.; Tsao, M.-S.; Kim, S.; Lee, D.-k., Alkaline phosphatase ALPPL-2 is a novel pancreatic carcinoma-associated protein. Cancer Research 2013, 73 (6), 1934.
110. Shigdar, S.; Qiao, L.; Zhou, S.-F.; Xiang, D.; Wang, T.; Li, Y.; Lim, L. Y.; Kong, L.; Li, L.; Duan, W., RNA aptamers targeting cancer stem cell marker CD133. Cancer Letters 2013, 330 (1), 84-95.
111. Li, N.; Nguyen, H. H.; Byrom, M.; Ellington, A. D., Inhibition of cell proliferation by an Anti-EGFR aptamer. PLOS ONE 2011, 6 (6), e20299.
112. Dastjerdi, K.; Tabar, G. H.; Dehghani, H.; Haghparast, A., Generation of an enriched pool of DNA aptamers for an HER2-overexpressing cell line selected by Cell SELEX. Biotechnology and Applied Biochemistry 2011, 58 (4), 226-230.
113. Liu, Z.; Duan, J.-H.; Song, Y.-M.; Ma, J.; Wang, F.-D.; Lu, X.; Yang, X.-D., Novel HER2 aptamer selectively delivers cytotoxic drug to HER2-positive breast cancer cells in vitro. Journal of Translational Medicine 2012, 10 (1), 148.
114. Mallikaratchy, P.; Tang, Z.; Kwame, S.; Meng, L.; Shangguan, D.; Tan, W., Aptamer directly evolved from live cells recognizes membrane bound immunoglobin heavy mu chain in Burkitt's lymphoma cells. Mol Cell Proteomics 2007, 6 (12), 2230-8.
115. Xing, H.; Wong, N. Y.; Xiang, Y.; Lu, Y., DNA aptamer functionalized nanomaterials for intracellular analysis, cancer cell imaging and drug delivery. Curr Opin Chem Biol 2012, 16 (3-4), 429-35.
116. Shi, H.; Cui, W.; He, X.; Guo, Q.; Wang, K.; Ye, X.; Tang, J., Whole Cell-SELEX aptamers for highly specific fluorescence molecular imaging of carcinomas in vivo. PLOS ONE 2013, 8 (8), e70476.
117. Ng, E. W.; Shima, D. T.; Calias, P.; Cunningham, E. T.; Guyer, D. R.; Adamis, A. P., Pegaptanib, a targeted anti-VEGF aptamer for ocular vascular disease. Nat Rev Drug Discov 2006, 5 (2), 123-32.
118. Fang, X.; Tan, W., Aptamers generated from cell-SELEX for molecular medicine: a chemical biology approach. Acc Chem Res 2010, 43 (1), 48-57.
119. Keefe, A. D.; Pai, S.; Ellington, A., Aptamers as therapeutics. Nat Rev Drug Discov 2010, 9 (7), 537-50.
120. Liu, H.; Xiang, Y.; Lu, Y.; Crooks, R. M., Aptamer-based origami paper analytical device for electrochemical detection of adenosine. Angew Chem Int Ed Engl 2012, 51 (28), 6925-8.
121. Banerjee, J.; Nilsen-Hamilton, M., Aptamers: multifunctional molecules for biomedical research. J Mol Med (Berl) 2013, 91 (12), 1333-42.
122. Kong, H. Y.; Byun, J., Nucleic Acid aptamers: new methods for selection, stabilization, and application in biomedical science. Biomol Ther (Seoul) 2013, 21 (6), 423-34.
123. Schoukroun-Barnes, L. R.; Wagan, S.; White, R. J., Enhancing the analytical performance of electrochemical RNA aptamer-based sensors for sensitive detection of aminoglycoside antibiotics. Anal Chem 2014, 86 (2), 1131-7.
124. Zhou, W.; Huang, P. J.; Ding, J.; Liu, J., Aptamer-based biosensors for biomedical diagnostics. Analyst 2014, 139 (11), 2627-40.
125. Sun, H.; Zhu, X.; Lu, P. Y.; Rosato, R. R.; Tan, W.; Zu, Y., Oligonucleotide aptamers: new tools for targeted cancer therapy. Mol Ther Nucleic Acids 2014, 3, e182.
126. Jelic, S.; Sotiropoulos, G. C.; Group, E. G. W., Hepatocellular carcinoma: ESMO clinical practice guidelines for diagnosis, treatment and follow-up. Ann Oncol 2010, 21 Suppl 5, v59-64.
127. Sefah, K.; Shangguan, D.; Xiong, X.; O'Donoghue, M. B.; Tan, W., Development of DNA aptamers using Cell-SELEX. Nat Protoc 2010, 5 (6), 1169-85.
128. Li, H.; He, Y.; Ding, G.; Wang, C.; Xie, L.; Li, Y., dbDEPC: a database of differentially expressed proteins in human cancers. Nucleic Acids Res 2010, 38 (Database issue), D658-64.
129. Zhao, J.; Lee, S. H.; Huss, M.; Holme, P., The network organization of cancer-associated protein complexes in human tissues. Sci Rep 2013, 3, 1583.
130. Lee, Y.-T. M.; Geer, D. A., Primary liver cancer: pattern of metastasis. Journal of Surgical Oncology 1987, 36 (1), 26-31.
131. Subik, K.; Lee, J. F.; Baxter, L.; Strzepek, T.; Costello, D.; Crowley, P.; Xing, L.; Hung, M. C.; Bonfiglio, T.; Hicks, D. G.; Tang, P., The expression patterns of ER, PR, HER2, CK5/6, EGFR, Ki-67 and AR by immunohistochemical analysis in breast cancer cell lines. Breast Cancer (Auckl) 2010, 4, 35-41.
132. Xu, J.; Teng, I. T.; Zhang, L.; Delgado, S.; Champanhac, C.; Cansiz, S.; Wu, C.; Shan, H.; Tan, W., Molecular recognition of human liver cancer cells using DNA aptamers generated via Cell-SELEX. PLOS ONE 2015, 10 (5), e0125863.
133. Krylova, S. M.; Musheev, M.; Nutiu, R.; Li, Y.; Lee, G.; Krylov, S. N., Tau protein binds single-stranded DNA sequence specifically—the proof obtained in vitro with non-equilibrium capillary electrophoresis of equilibrium mixtures. FEBS Letters 2005, 579 (6), 1371-1375.
134. Bing, T.; Yang, X.; Mei, H.; Cao, Z.; Shangguan, D., Conservative secondary structure motif of streptavidin-binding aptamers generated by different laboratories. Bioorganic & Medicinal Chemistry 2010, 18 (5), 1798-1805.
135. Yang, X.; Bing, T.; Mei, H.; Fang, C.; Cao, Z.; Shangguan, D., Characterization and application of a DNA aptamer binding to 1-tryptophan. Analyst 2011, 136 (3), 577-585.
136. Bing, T.; Chang, T.; Yang, X.; Mei, H.; Liu, X.; Shangguan, D., G-quadruplex DNA aptamers generated for systemin. Bioorganic & Medicinal Chemistry 2011, 19 (14), 4211-4219.

137. Mei, H.; Bing, T.; Yang, X.; Qi, C.; Chang, T.; Liu, X.; Cao, Z.; Shangguan, D., Functional-group specific aptamers indirectly recognizing compounds with alkyl amino group. Analytical Chemistry 2012, 84 (17), 7323-7329.

138. Qi, C.; Bing, T.; Mei, H.; Yang, X.; Liu, X.; Shangguan, D., G-quadruplex DNA aptamers for zeatin recognizing. Biosensors and Bioelectronics 2013, 41, 157-162.

139. Behlke, M. A.; Huang, L.; Bogh, L.; Rose, S.; Devor, E. J., Fluorescence quenching by proximal G-bases. Integrated DNA Technologies 2005.

140. Grate, D.; Wilson, C., Inducible regulation of the S. cerevisiae cell cycle mediated by an RNA aptamer-ligand complex. Bioorganic & Medicinal Chemistry 2001, 9 (10), 2565-2570.

141. Weigand, J. E.; Suess, B., Tetracycline aptamer-controlled regulation of pre-mRNA splicing in yeast. Nucleic Acids Research 2007, 35 (12), 4179-4185.

142. Reyes-Reyes, E. M.; Šalipur, F. R.; Shams, M.; Forsthoefel, M. K.; Bates, P. J., Mechanistic studies of anticancer aptamer AS1411 reveal a novel role for nucleolin in regulating Rac1 activation. Molecular Oncology 2015, 9 (7), 1392-1405.

143. Cheng, Y.; Zhao, G.; Zhang, S.; Nigim, F.; Zhou, G.; Yu, Z.; Song, Y.; Chen, Y.; Li, Y., AS1411-induced growth inhibition of glioma cells by up-regulation of p53 and down-regulation of Bcl-2 and Akt1 via nucleolin. PLOS ONE 2016, 11 (12), e0167094.

144. Yoon, S.; Armstrong, B.; Habib, N.; Rossi, J. J., Blind SELEX approach identifies RNA aptamer that regulate EMT and inhibit metastasis. Molecular Cancer Research 2017.

145. Kligman, D.; Marshak, D. R., Purification and characterization of a neurite extension factor from bovine brain. Proceedings of the National Academy of Sciences 1985, 82 (20), 7136-7139.

146. Selinfreund, R. H.; Barger, S. W.; Pledger, W. J.; Van Eldik, L. J., Neurotrophic protein S100 beta stimulates glial cell proliferation. Proceedings of the National Academy of Sciences of the United States of America 1991, 88 (9), 3554-3558.

147. Reeves, R. H.; Yao, J.; Crowley, M. R.; Buck, S.; Zhang, X.; Yarowsky, P.; Gearhart, J. D.; Hilt, D. C., Astrocytosis and axonal proliferation in the hippocampus of S100b transgenic mice. Proceedings of the National Academy of Sciences of the United States of America 1994, 91 (12), 5359-5363.

148. Villarreal, A.; Aviles Reyes, R. X.; Angelo, M. F.; Reines, A. G.; Ramos, A. J., S100B alters neuronal survival and dendrite extension via RAGE-mediated NF-κB signaling. Journal of Neurochemistry 2011, 117 (2), 321-332.

149. Bishop, P.; Rocca, D.; Henley, Jeremy M., Ubiquitin C-terminal hydrolase L1 (UCH-L1): structure, distribution and roles in brain function and dysfunction. Biochemical Journal 2016, 473 (16), 2453-2462.

150. Moroz, L. L., Aplysia. Current Biology 2011, 21 (2), R60-R61.

151. Rayport, S. G.; Ambron, R. T.; Babiarz, J., Identified cholinergic neurons R2 and LP11 control mucus release in Aplysia. Journal of Neurophysiology 1983, 49 (4), 864.

152. Andreasen, N.; Sjögren, M.; Blennow, K., CSF markers for Alzheimer's disease: Total tau, phospho-tau and Aβ42. The World Journal of Biological Psychiatry 2003, 4 (4), 147-155.

153. Shaw, L. M.; Vanderstichele, H.; Knapik-Czajka, M.; Clark, C. M.; Aisen, P. S.; Petersen, R. C.; Blennow, K.; Soares, H.; Simon, A.; Lewczuk, P.; Dean, R.; Siemers, E.; Potter, W.; Lee, V. M. Y.; Trojanowski, J. Q., Cerebrospinal fluid biomarker signature in Alzheimer's disease neuroimaging initiative subjects. Annals of Neurology 2009, 65 (4), 403-413.

154. Kandimalla, R. J. L.; Prabhakar, S.; Wani, W. Y.; Kaushal, A.; Gupta, N.; Sharma, D. R.; Grover, V. K.; Bhardwaj, N.; Jain, K.; Gill, K. D., CSF p-Tau levels in the prediction of Alzheimer's disease. Biology Open 2013, 2 (11), 1119-1124.

155. Brier, M. R.; Gordon, B.; Friedrichsen, K.; McCarthy, J.; Stern, A.; Christensen, J.; Owen, C.; Aldea, P.; Su, Y.; Hassenstab, J.; Cairns, N. J.; Holtzman, D. M.; Fagan, A. M.; Morris, J. C.; Benzinger, T. L. S.; Ances, B. M., Tau and Aβ imaging, CSF measures, and cognition in Alzheimer's disease. Science Translational Medicine 2016, 8 (338), 338ra66.

156. Meredith Jr, J. E.; Sankaranarayanan, S.; Guss, V.; Lanzetti, A. J.; Berisha, F.; Neely, R. J.; Slemmon, J. R.; Portelius, E.; Zetterberg, H.; Blennow, K.; Soares, H.; Ahlijanian, M.; Albright, C. F., Characterization of novel CSF tau and ptau biomarkers for Alzheimer's disease. PLOS ONE 2013, 8 (10), e76523.

157. Li, J. J.; Fang, X.; Schuster, S. M.; Tan, W., Molecular beacons: a novel approach to detect protein—DNA Interactions. Angewandte Chemie International Edition 2000, 39 (6), 1049-1052.

158. Leung, C.-H.; Chan, D. S.-H.; He, H.-Z.; Cheng, Z.; Yang, H.; Ma, D.-L., Luminescent detection of DNA-binding proteins. Nucleic Acids Research 2012, 40 (3), 941-955.

159. Kim J H, Kim E, Choi W H, Lee J, Lee J H, Lee H, Kim D E, Suh Y H, Lee M J Inhibitory RNA Aptamers of Tau Oligomerization and Their Neuroprotective Roles against Proteotoxic Stress. Mol Pharm. 2016 Jun. 6; 13(6):2039-48.

160. Germany patent application DE 102010038842 A1: New aptamer that specifically binds to human tau protein or its fragment, useful e.g. in vitro for isolating, purifying and/or detecting tau protein, and to treat cerebral infarction, pick disease and/or progressive supranuclear palsy, filed on Aug. 3, 2010.

All documents, patents, patent applications, journal articles and other materials cited in the present application are incorporated herein by reference.

While the disclosed invention has been disclosed with references to certain embodiments, numerous modification, alterations, and changes to the described embodiments are possible without departing from the sphere and scope of the disclosed invention, as defined in the appended claims. Accordingly, it is intended that the disclosed invention not be limited to the described embodiments, but that it has the full scope defined by the language of the following claims, and equivalents thereof.

What is claimed is:

1. A DNA aptamer comprising a nucleic acid sequence that is capable of specifically binding to a tau protein at a phosphorylatable site of the tau protein; wherein the nucleic acid sequence comprises 66 nucleotides and is selected from the group consisting of SEQ ID NO: 1, SEQ ID NO: 2, SEQ ID NO: 3, SEQ ID NO: 4, SEQ ID NO: 5, SEQ ID NO: 6, and SEQ ID NO: 7.

2. A DNA aptamer comprising a nucleic acid sequence that is capable of specifically binding to a tau protein at a phosphorylatable site of the tau protein; wherein the nucleic acid sequence is selected from the group consisting of SEQ ID NO: 8, SEQ ID NO: 9, SEQ ID NO: 10, and SEQ ID NO: 11; and wherein the nucleic acid sequence is a truncated fragment of a nucleic acid sequence set forth in SEQ ID NO: 1, and wherein the DNA aptamer is comprised of 100 nucleotides or less.

3. A DNA aptamer comprising a nucleic acid sequence that is capable of specifically binding to a tau protein at a phosphorylatable site of the tau protein; wherein the nucleic acid sequence is selected from the group consisting of SEQ ID NO: 17, SEQ ID NO: 18, and SEQ ID NO: 19; and wherein the nucleic acid sequence is a truncated fragment of a nucleic acid sequence set forth in SEQ ID NO: 3, and wherein the DNA aptamer is comprised of 100 nucleotides or less.

4. A DNA aptamer comprising a nucleic acid sequence that is capable of specifically binding to a tau protein at a phosphorylatable site of the tau protein; wherein the nucleic acid sequence is selected from the group consisting of SEQ ID NO: 20, SEQ ID NO: 21, and SEQ ID NO: 22; and wherein the nucleic acid sequence is a truncated fragment of a nucleic acid sequence set forth in SEQ ID NO: 4, and wherein the DNA aptamer is comprised of 100 nucleotides or less.

5. A DNA aptamer comprising a nucleic acid sequence that is capable of specifically binding to a tau protein at a phosphorylatable site of the tau protein; wherein the nucleic acid sequence is selected from the group consisting of SEQ ID NO: 23, SEQ ID NO: 24, and SEQ ID NO: 25; and wherein the nucleic acid sequence is a truncated fragment of a nucleic acid sequence set forth in SEQ ID NO: 5, and wherein the DNA aptamer is comprised of 100 nucleotides or less.

6. A DNA aptamer comprising a nucleic acid sequence that is capable of specifically binding to a tau protein at a phosphorylatable site of the tau protein; wherein the nucleic acid sequence is selected from the group consisting of SEQ ID NO: 26 and SEQ ID NO: 27; and wherein the nucleic acid sequence is a truncated fragment of a nucleic acid sequence set forth in SEQ ID NO: 6, and wherein the DNA aptamer is comprised of 100 nucleotides or less.

7. A composition comprising a DNA aptamer that is capable of specifically binding to a tau protein at a phosphorylatable site of the tau protein, wherein the DNA aptamer comprises a nucleic acid sequence comprising 66 nucleotides and is selected from the group consisting of SEQ ID NO: 1, SEQ ID NO: 2, SEQ ID NO: 3, SEQ ID NO: 4, SEQ ID NO:5, SEQ ID NO: 6, and SEQ ID NO: 7, and wherein the DNA aptamer is comprised of 100 nucleotides or less.

8. The composition of claim 7, further comprising a pharmaceutically acceptable carrier or salt.

9. A composition comprising a DNA aptamer that is capable of specifically binding to a tau protein at a phosphorylatable site of the tau protein, wherein the DNA aptamer comprises a nucleic acid sequence selected from the group consisting of SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and SEQ ID NO: 27, and wherein the DNA aptamer is comprised of 100 nucleotides or less.

10. The composition of claim 7, further comprising a pharmaceutically acceptable excipient.

* * * * *

SEQUENCE LISTING

<160> NUMBER OF SEQ ID NOS: 52

<210> SEQ ID NO 1
<211> LENGTH: 66
<212> TYPE: DNA
<213> ORGANISM: Artificial Sequence
<220> FEATURE:
<223> OTHER INFORMATION: synthetic oligonucleotide

<400> SEQUENCE: 1
cagcaccgtc aactgaattg cttggtcctc ccggggttct ggaaaagcgt gatgcgatgg    60
agatgt                                                              66

<210> SEQ ID NO 2
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 2
cagcaccgtc aactgaataa ggactgctta ggattgcgat gattcagggt gatgcgatgg    60
agatgt                                                              66

<210> SEQ ID NO 3
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 3
cagcaccgtc aactgaatgg ggagagtggt ggggcggggg ccggatccgt gatgcgatgg    60
agatgt                                                              66

<210> SEQ ID NO 4
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 4
cagcaccgtc aactgaatgg gttggccggg cagcggggggg taggcttggt gatgcgatgg    60
agatgt                                                              66

<210> SEQ ID NO 5
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 5
cagcaccgtc aactgaatgg cgggggtca ggtcgggta aggtgagcgt gatgcgatgg      60
agatgt                                                              66

<210> SEQ ID NO 6
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 6
cagcaccgtc aactgaatgt tgtcgtcaga ggttataacc tgaactcggt gatgcgatgg    60
agatgt                                                              66

<210> SEQ ID NO 7
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 7
cagcaccgtc aactgaattg cgggggggtca ggtcgggggta aggtgagcgt gatgcgatgg   60
agatgt                                                              66

<210> SEQ ID NO 8
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 8
ccgtcaactg aattgcttgg tcctcccggg gttctggaaa agcgtgatgc gatgg         55

<210> SEQ ID NO 9
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 9
ccgtcaactg aattgcttgg tcctcccggg gttctggaaa agc                     43

<210> SEQ ID NO 10
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 10
gcttggtcct cccggggttc tggaaaagc                                     29

<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 11
ttggtcctcc cggggttctg gaaaa                                         25

<210> SEQ ID NO 12
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 12
ctgaataagg actgcttagg attgcgatga ttcag                                    35

<210> SEQ ID NO 13
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 13
aaggactgct taggattgc                                                      19

<210> SEQ ID NO 14
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 14
tgaataagga ctgcttagga ttgcgatgat tca                                      33

<210> SEQ ID NO 15
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 15
gaataaggac tgcttaggat tgcgatgatt c                                        31

<210> SEQ ID NO 16
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 16
aataaggact gcttaggatt gcgatgatt                                           29

<210> SEQ ID NO 17
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 17
cagcaccgtc aactgaatgg ggagagtggt ggggcgg                                  37

<210> SEQ ID NO 18
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 18
cagcaccgtc aactgaatgg ggagagtggt ggggcggggg ccggatccgt gatgcg             56

<210> SEQ ID NO 19
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 19
cagcaccgtc aactgaatgg ggagagtggt ggggcggggg ccggatccgt gatgcgatgg    60
a    61

<210> SEQ ID NO 20
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 20
caccgtcaac tgaatgggtt ggccgggcag cgggggtag gcttggtg    48

<210> SEQ ID NO 21
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 21
caccgtcaac tgaatgggtt ggccgggcag cgggggtag gcttggtgat gcgatg    56

<210> SEQ ID NO 22
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 22
cagcaccgtc aactgaatgg gttggccggg cagcgggggg taggcttggt gatgcgatg    59

<210> SEQ ID NO 23
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 23
ccgtcaactg aatggcgggg ggtcaggtcg g    31

<210> SEQ ID NO 24
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 24
caccgtcaac tgaatggcgg ggggtcaggt cggggtaagg tg    42

<210> SEQ ID NO 25
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 25

```
caccgtcaac tgaatggcgg ggggtcaggt cggggtaagg tgagcgtgat gcg          53
```

<210> SEQ ID NO 26
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 26

```
caccgtcaac tgaatgttgt cgtcagaggt tataacctga actcggtg               48
```

<210> SEQ ID NO 27
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 27

```
cgtcaactga atgttgtcgt cagaggttat aacctgaac                         39
```

<210> SEQ ID NO 28
<211> LENGTH: 13
<212> TYPE: PRT
<213> ORGANISM: Artificial Sequence
<220> FEATURE:
<223> OTHER INFORMATION: synthetic peptide

<400> SEQUENCE: 28

Thr Pro Pro Ala Pro Lys Thr Pro Pro Ser Ser Gly Glu
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Synthetic peptide

<400> SEQUENCE: 29

Gly Tyr Ser Ser Pro Gly Ser Pro Gly Thr Pro Gly Ser Arg
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Synthetic peptide

<400> SEQUENCE: 30

Lys Val Ala Val Val Arg Thr Pro Pro Lys Ser Pro Ser
1               5                   10

<210> SEQ ID NO 31
<211> LENGTH: 17
<212> TYPE: PRT
<213> ORGANISM: Artificial Sequence
<220> FEATURE:
<223> OTHER INFORMATION: Synthetic peptide

<400> SEQUENCE: 31

Glu Ile Val Tyr Lys Ser Pro Val Val Ser Gly Asp Thr Ser Pro Arg
1               5                   10                  15

His

<210> SEQ ID NO 32
<211> LENGTH: 6
<212> TYPE: PRT
<213> ORGANISM: Artificial Sequence
<220> FEATURE:
<223> OTHER INFORMATION: Synthetic peptide

<400> SEQUENCE: 32

His His His His His His
1               5

<210> SEQ ID NO 33
<211> LENGTH: 18
<212> TYPE: DNA
<213> ORGANISM: Artificial Sequence
<220> FEATURE:
<223> OTHER INFORMATION: Synthetic primer

<400> SEQUENCE: 33
cagcaccgtc aactgaat                                                   18

<210> SEQ ID NO 34
<211> LENGTH: 18
<212> TYPE: DNA
<213> ORGANISM: Artificial Sequence
<220> FEATURE:
<223> OTHER INFORMATION: Synthetic primer

<400> SEQUENCE: 34
acatctccat cgcatcac                                                   18

<210> SEQ ID NO 35
<211> LENGTH: 66
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (19)..(48)
<223> OTHER INFORMATION: n is a, c, g, or t

<400> SEQUENCE: 35
cagcaccgtc aactgaatnn nnnnnnnnnn nnnnnnnnnn nnnnnnnngt gatgcgatgg     60
agatgt                                                                66

<210> SEQ ID NO 36
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 36
gcggagcgtg gcagg                                                      15

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
aacgagaagc gcgatcacat                                                 20

<210> SEQ ID NO 38
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 38
cttctgcccg cctccttcc                                         19

<210> SEQ ID NO 39
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 39
atccagagtg acgcagcacc aataaatcta gccggggtat cggtggacac ggtggcttag    60
t                                                            61

<210> SEQ ID NO 40
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 40
tgcttggtcc tcccggggtt ctggaaaagc                             30

<210> SEQ ID NO 41
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 41
aaggactgct taggattgcg atgattcagg                             30

<210> SEQ ID NO 42
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 42
ggggagagtg gtggggcggg ggccggatcc                             30

<210> SEQ ID NO 43
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 43
gggttggccg ggcagcgggg ggtaggcttg                             30

<210> SEQ ID NO 44
<211> LENGTH: 30
<212> TYPE: DNA

```
<213> ORGANISM: Artificial Sequence
<220> FEATURE:
<223> OTHER INFORMATION: Synthetic oligonucleotide

<400> SEQUENCE: 44 ggcgggggt caggtcgggg taaggtgagc                                    30

<210> SEQ ID NO 45
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 45
gttgtcgtca gaggttataa cctgaactcg                                   30

<210> SEQ ID NO 46
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 46
gggggctgct taggattgcg gttgtttgtg                                   30

<210> SEQ ID NO 47
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 47
tgggagagtg gtggggcggg ggccggatcc                                   30

<210> SEQ ID NO 48
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 48
tgcggggggt caggtcgggg taaggtgagc                                   30

<210> SEQ ID NO 49
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 49
gaggactgct taggattgcg atgattcagg                                   30

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
taaggactgc ttaggattgc                                              20
```

```
<210> SEQ ID NO 51
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 51
caactgaatg gcgggggtc aggtcgg                                          27

<210> SEQ ID NO 52
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 52
gcaccgtcaa ctgaatggcg gggggtcagg tcggggtaag gtgagcgtga tgcga          55
```